US012644125B2

(12) United States Patent
Hausmann et al.

(10) Patent No.: US 12,644,125 B2
(45) Date of Patent: Jun. 2, 2026

(54) COMPOSITIONS AND METHODS FOR INDUCING AN ENHANCED IMMUNE RESPONSE USING POXVIRUS VECTORS

(71) Applicant: Bavarian Nordic A/S, Hellerup (DK)

(72) Inventors: Jürgen Hausmann, Gundelfingen (DE); Michael Wolferstätter, Munich (DE)

(73) Assignee: Bavarian Nordic A/S, Hellerup (DK)

( * ) Notice: Subject to any disclaimer, the term of this patent is extended or adjusted under 35 U.S.C. 154(b) by 707 days.

(21) Appl. No.: 16/846,325

(22) Filed: Apr. 11, 2020

(65) Prior Publication Data

US 2020/0325477 A1     Oct. 15, 2020

Related U.S. Application Data

(63) Continuation of application No. 15/039,777, filed as application No. PCT/EP2014/075522 on Nov. 25, 2014, now abandoned.

(30) Foreign Application Priority Data

Nov. 28, 2013     (EP) ..................................... 13005541

(51) Int. Cl.
| | |
|---|---|
| C12N 15/117 | (2010.01) |
| A61K 39/275 | (2006.01) |
| A61K 39/39 | (2006.01) |
| C12N 7/00 | (2006.01) |
| C12N 15/86 | (2006.01) |
| A61K 39/00 | (2006.01) |

(52) U.S. Cl.
CPC ............ *C12N 15/117* (2013.01); *A61K 39/39* (2013.01); *C12N 7/00* (2013.01); *C12N 15/86* (2013.01); *A61K 2039/55561* (2013.01); *C12N 2310/17* (2013.01); *C12N 2310/53* (2013.01); *C12N 2330/51* (2013.01); *C12N 2710/24021* (2013.01); *C12N 2710/24043* (2013.01); *C12N 2710/24063* (2013.01)

(58) Field of Classification Search
CPC .................................................. A61K 39/275
See application file for complete search history.

(56) References Cited

U.S. PATENT DOCUMENTS

| | | | | |
|---|---|---|---|---|
| 5,494,807 | A | 2/1996 | Paoletti | |
| 7,538,095 | B2 | 5/2009 | Fire | |
| 7,744,900 | B2 * | 6/2010 | Dubensky, Jr. | ......... A61P 37/00 |
| | | | | 435/69.51 |
| 2005/0281782 | A1 | 12/2005 | Kaufman et al. | |
| 2006/0073594 | A1 | 4/2006 | Yao et al. | |

FOREIGN PATENT DOCUMENTS

| | | | | |
|---|---|---|---|---|
| EP | 2042604 A1 * | 4/2009 | .............. | A61P 37/04 |
| GB | 2 027 033 A | 2/1980 | | |

| | | | |
|---|---|---|---|
| WO | 2000034494 A1 | 6/2000 | |
| WO | 2000063364 A2 | 10/2000 | |
| WO | 2004009763 A2 | 1/2004 | |

OTHER PUBLICATIONS

Lynch et al. (2009) Modified vaccinia virus Ankara can activate NF-κB transcription factors through a double-stranded RNA-activated protein kinase (PKR)-dependent pathway during the early phase of virus replication. Virology, 391:177-186 (Year: 2009).*
Ludwig et al. (2006) Double-stranded RNA-binding protein E3 controls translation of viral intermediate RNA, marking an essential step in the life cycle of modified vaccinia virus Ankara. Journal of General Virology, 87:1145-1155 (Year: 2006).*
Jentarra et al. (2008) Vaccinia viruses with mutations in the E3L gene as potential replication-competent, attenuated vaccines: Scarification vaccination. Vaccine, 26:2860-2872 (Year: 2008).*
Marshall, J, et al. Phase I study of sequential vaccinations with fowlpox-CEA (6D)-TRICOM alone and sequentially with vaccinia-CEA (6D)-TRICOM, with and without granulocyte-macrophage colony-stimulating factor, in patients with carcinoembryonic antigen-expressing carcinomas. J.Clin Ocol. 23.4:720-731. (Year: 2005).*
Ambrosini et al., "Gene Transfer in Astrocytes: Comparison Between Different Delivering Methods and Expression of the HIV-1 Protein Nef," J. Neurosci. Res., 1999, pp. 569-577, vol. 55.
Written Opinion and Search Report of the International Search Authority for PCT/EP2014/075522, dated Mar. 4, 2015.
Dmitriev et al., "Immunization with recombinant vaccinia virus expressing structural and part of the nonstructural region of tick-borne encephalitis virus cDNA protect mice against lethal encephalitis," Journal of Biotechnology, 1996, pp. 97-103, vol. 44.
Garnett et al., "TRICOM Vector Based Cancer Vaccines," Current Pharmaceutical Design, 2006, pp. 351-361, vol. 12.
Assarsson et al., "Kinetic analysis of a complete poxvirus transcriptome reveals an immediate-early class of genes," Proc. Nat'l. Acad. Sci. USA, 2008, pp. 2140-2145, vol. 105.
Wolferstätter et al., Recombinant Modified Vaccinia Virus Ankara Generating Excess Early Double-Stranded RNA Transiently Activates Protein Kinase R and Triggers Enhanced Innate Immune Responses, Journal of Virology, 2014, pp. 14396-14411, vol. 88.

(Continued)

*Primary Examiner* — Neil P Hammell
*Assistant Examiner* — Khaleda B Hasan

(57)     ABSTRACT

Provided herein are recombinant poxviruses comprising heterologous or native nucleic acids specifying excess double-stranded RNA (dsRNA) early in infection, which may further comprise heterologous nucleic acids encoding one or more costimulatory molecules, and/or heterologous nucleic acids encoding one or more infectious disease-associated antigens or tumor-associated antigens, as well as pharmaceutical compositions comprising such recombinant poxviruses and methods and uses thereof. The recombinant poxviruses provided herein enhance innate and adaptive immune activation in subjects compared to identical recombinant poxviruses lacking heterologous or native transcription units specifying excess early dsRNA.

20 Claims, 28 Drawing Sheets

Specification includes a Sequence Listing.

(56)                References Cited

OTHER PUBLICATIONS

Antoine et al., "The Complete Genomic Sequence of the Modified Vaccinia Ankara Strain: Comparison with Other Orthopoxviruses," Virology, 1998, pp. 365-396, vol. 244.

Barry et al., "PKR acts early in infection to suppress Semliki Forest virus production and strongly enhances the type I interferon response," J. Gen. Virol., 2009, pp. 1382-1391, vol. 90.

Beattie et al., "Distinct Patterns of IFN Sensitivity Observed in Cells Infected with Vaccinia K3L and E3L Mutant Viruses," Virology, 1995, pp. 254-263, vol. 210.

Blanchard et al., "Modified vaccinia virus Ankara undergoes limited replication in human cells and lacks several immunomodulatory proteins: implications for use as a human vaccine," Journal of General Virology,1998, pp. 1159-1167, vol. 79.

Boone et al., "Intermolecular Duplexes Formed from Polyadenylylated Vaccinia Virus RNA," Journal of Virology, 1979, pp. 365-374, vol. 30.

Boukamp et al., "Normal Keratinization in a Spontaneously Immortalized Aneuploid Human Keratinocyte Cell Line," Journal of Cell Biology, 1988, pp. 761-771, vol. 106.

Carroll et al., "Host Range and Cytopathogenicity of the Highly Attenuated MVA Strain of Vaccinia Virus: Propagation and Generation of Recombinant Viruses in a Nonhuman Mammalian Cell Line," Virology, 1997, pp. 198-211, vol. 238.

Chen et al., Inhibition of IjB Kinase by Vaccinia Virus Virulence Factor B14, PLoS Pathogens, 2008, pp. 1-9, vol. 4.

Colby et al., "Double Stranded RNA in Vaccinia Virus Infected Cells," Nature, 1969, pp. 940-944, vol. 222.

Cooper et al., "Extension of the Transcriptional and Translational Map of the Left End of the Vaccinia Virus Genome to 21 Kilobase Pairs," J. Virol., 1981, pp. 733-745, vol. 39.

Corpet, "Multiple sequence alignment with hierarchical clustering," Nucl. Acids Res., 1988, pp. 10881-10890, vol. 16.

Cosma et al., "Therapeutic vaccination with MVA-HIV-1 nef elicits Nef-specific T-helper cell responses in chronically HIV-1 infected individuals," Vaccine, 2003, pp. 21-29, vol. 22.

Desmet and Ishii, "Nucleic acid sensing at the interface between innate and adaptive immunity in vaccination," Nat. Rev. Immunol., 2012, pp. 479-491, vol. 12.

Di Nicola et al., "Immunization of Patients with Malignant Melanoma with Autologous CD341 Cell-Derived Dendritic Cells Transduced Ex Vivo with a Recombinant Replication-Deficient Vaccinia Vector Encoding the Human Tyrosinase Gene: A Phase I Trial," Human Gene Therapy, 2003, pp. 1347-1360, vol. 14.

Di Nicola et al., "Boosting T Cell-Mediated Immunity to Tyrosinase by Vaccinia Virus-Transduced, CD34-Derived Dendritic Cell Vaccination: A Phase I Trial in Metastatic Melanoma," Clin. Cancer Res., 2004, pp. 5381-5390, vol. 10.

Duesberg and Colby, "On the Biosynthesis and Structure of Double-Stranded RNA in Vaccinia Virus-Infected Cells," Biochemistry, 1969, pp. 396-403, vol. 64.

Garcia et al., "Impact of Protein Kinase PKR in Cell Biology: from Antiviral to Antiproliferative Action," Microbiol. Mol. Biol. Rev., 2006, pp. 1032-1060, vol. 70.

Garnett et al., "TRICOM Vector Based Cancer Vaccines," Curr. Pharm. Design, 2006, pp. 351-361, vol. 12.

Gilfoy et al., "West Nile Virus-Induced Interferon Production Is Mediated by the Double-Stranded RNA-Dependent Protein Kinase PKR," J. Virol., 2007, pp. 11148-11158, vol. 81.

Harrer et al., "Therapeutic vaccination of HIV-1-infected patients on HAART with a recombinant HIV-1 nef-expressing MVA: safety, immunogenicity and influence on viral load during treatment interruption," Antiviral Therapy, 2005, pp. 285-300, vol. 10.

Hochrein and O'Keeffe, "Dendritic Cell Subsets and Toll-Like Receptors," Handbook of Experimental Pharmacology, 2008, pp. 153-179.

Hochrein et al., "Herpes simplex virus type-1 induces IFN-α production via Toll-like receptor 9-dependent and -independent pathways," Proc. Nat'l. Acad. Sci., 2004, pp. 11416-11421, vol. 101.

Hodge et al., "A Triad of Costimulatory Molecules Synergize to Amplify T-Cell Activation," Cancer Res., 1999, pp. 5800-5807, vol. 59.

Hornemann et al., "Replication of Modified Vaccinia Virus Ankara in Primary Chicken Embryo Fibroblasts Requires Expression of the Interferon Resistance Gene E3L," J. Virol., 2003, pp. 8394-8407, vol. 77.

Iwasaki et al., "A Virological View of Innate Immune Recognition," Annu. Rev. Microbiol., 2012, pp. 177-196, vol. 66.

Iwasaki et al., "Regulation of Adaptive Immunity by the Innate Immune System," Science, 2010, pp. 291-295, vol. 327.

Kibler et al., "Double-Stranded RNA Is a Trigger for Apoptosis in Vaccinia Virus-Infected Cells," J. Virol., 1997, pp. 1992-2003, vol. 71.

Lauterbach et al., "Mouse CD8a+ DCs and human BDCA3+ DCs are major producers of IFN in response to poly IC," J. Exp. Med., 2010, pp. 2703-2717, vol. 207.

Lynch et al., "Modified vaccinia virus Ankara can activate NF-κB transcription factors through a double-stranded RNA-activated protein kinase (PKR)-dependent pathway during the early phase of virus replication," Virology, 2009, pp. 177-186, vol. 391.

McCoy et al., "Mutations in modified virus Ankara protein 183 render it a non-functional counterpart of B14, an inhibitor of nuclear factor kB activation," J. Gen. Virol., 2010, pp. 2216-2220, vol. 91.

Meisinger-Henschel et al., "Genomic sequence of chorioallantois vaccinia virus Ankara, the ancestor of modified vaccinia virus Ankara," J. Gen. Virol., 2007, pp. 3249-3259, vol. 88.

Meisinger-Henschel et al., "Introduction of the Six Major Genomic Deletions of Modified Vaccinia Virus Ankara (MVA) into the Parental Vaccinia Virus Is Not Sufficient To Reproduce an MVA-Like Phenotype in Cell Culture and in Mice," J. Virol., 2010, pp. 9907-9919, vol. 84.

Melchjorsen, "Learning from the Messengers: Innate Sensing of Viruses and Cytokine Regulation of Immunity-Clues for Treatments and Vaccines," Viruses, 2013, pp. 470-527, vol. 5. HEREHEREHERE.

Samuelsson et al., "Survival of lethal poxvirus infection in mice depends on TLR9, and therapeutic vaccination provides protection," J. Clin. Invest., 2008, pp. 1776-1784, vol. 118.

Smith et al., "Poxviruses: Interfering with Interferon," Seminars in Virology, 1998, pp. 409-418, vol. 8.

Vijaysri et al., "Vaccinia viruses with mutations in the E3L gene as potential replication-competent, attenuated vaccines: intranasal vaccination," Vaccine, 2008, pp. 664-676, vol. 26.

Williams, "PKR; a sentinel kinase for cellular stress," Oncogene, 1999, pp. 6112-6120, vol. 18.

Willis et al., "The effect of the vaccinia K1 protein on the PKR-eIF2a pathway in RK13 and HeLa cells," Virology, 2009, pp. 73-81, vol. 394.

Willis et al., Viral Double-stranded RNAs from Vaccinia Virus Early or Intermediate Gene Transcripts Possess PKR Activating Function, Resulting in NF-B Activation, When the K1 Protein Is Absent or Mutated*, J. Biol. Chem., 2011, pp. 7765-7778, vol. 286.

Wyatt et al., "Development of a replication-deficient recombinant vaccinia virus vaccine effective against parainfluenza virus 3 infection in an animal model," Vaccine, 1996, pp. 1451-1458, vol. 14.

Xiang et al., "The Vaccinia Virus A18R DNA Helicase Is a Postreplicative Negative Transcription Elongation Factor," J. Virol., 1998, pp. 7012-7023, vol. 72.

Yuen and Moss, "Oligonucleotide sequence signaling transcriptional termination of vaccinia virus early genes," Proc. Nat'l. Acad. Sci., 1987, pp. 6417-6421, vol. 84.

Broyles, "Vaccinia virus transcription," J. Gen. Virol., 2003, pp. 2293-2303, vol. 84.

Broyles et al., "Poxvirus transcription," Future Virol., 2010, pp. 639-650, vol. 5.

Dewitte-Orr, "Long double-stranded RNA induces an antiviral response independent of IFN regulatory factor 3, IFN-[beta] promoter stimulator 1, and IFN," J. Immunol., 2009, pp. 6545-6553, vol. 183.

Harcourt and Offerman, "Interferon-[alpha] synergistically enhances induction of interleukin-6 by double stranded RNA in HeLa cells," Eur. J. Biochem., 2000, pp. 2768-2777, vol. 267.

(56)    References Cited

OTHER PUBLICATIONS

Ink and Pickup, "Transcription of a poxvirus early gene is regulated both by a short promoter element and by a transcriptional termination signal controlling transcriptional interference," J. Virol., 1989, pp. 4632-4644, vol. 63.

Kanneganti et al., "Critical Role for Cryopyrin/Nalp3 in Activation of Caspase-1 in Response to Viral Infection and Double-stranded RNA," J. Biol. Chem., 2006, pp. 36560-36568, vol. 281.

Karpala et al., "Activation of the TLR3 pathway regulates IFN[beta] production in chickens," Devt. Comp. Immunol., 2008, pp. 435-444, vol. 32.

Liu et al., "Poxvirus decapping enzymes enhance virulence by preventing the accumulation of dsRNA and the induction of innate antiviral responses," Cell Host & Microbe, 2015, pp. 320-331, vol. 17.

Londhe et al., "CXCR2/CXCR2 ligand biological axis impairs alveologenesis during dsRNA-induced lung inflammation in mice," Ped. Res., 2005, pp. 919-926, vol. 58.

Orubu et al., "Expression and cellular immunogenicity of a transgenic antigen driven by endogenous poxviral early promoters at their authentic loci in MVA," PLoS One, 2012, pp. 1-11, vol. 7.

Walther and Stein, "Viral vectors for gene transfer," Drugs, 2000, pp. 249-271, vol. 60.

Woernle et al., "Novel role of toll-like receptor 3, RIG-I and MDA5 in poly (I:C) RNA-induced mesothelial inflammation," Mol. Cell. Biochem., 2009, pp. 193-206, vol. 322.

Xiang et al., "The vaccinia virus A18R DNA helicase is a postreplicative negative transcription elongation factor," J. Virol., 1998, pp. 7102-7123, vol. 72.

Baroudy et al., GenBank Accession No. NC006998, Nov. 22, 2012, Vaccinia virus complete genome.

UniProtKB P20983, A4L protein of Vaccinia virus, priority to 1991.

Bayliss and Condit, "Temperature-Sensitive Mutants in the Vaccinia Virus A18R Gene Increase Double-Stranded RNA Synthesis as a Result of Aberrant Viral Transcription," 1993, Virology, pp. 254-262, vol. 194.

Lantermann et al., "Vaccinia virus double-stranded RNA-binding protein E3 does not interfere with siRNA-mediated gene silencing in mammalian cells," 2007, Virus Research, pp. 1-8, vol. 126.

Munir and Berg, "The multiple faces of proteinkinase R in antiviral defense," 2013, Virulence, pp. 85-89, vol. 4.

Ostertag et al., "Overproduction of Double-Stranded RNA in Vesicular Stomatitis Virus-Infected Cells Activates a Constitutive Cell-Type-Specific Antiviral Response," 2007, J. Virol., pp. 503-513, vol. 81.

* cited by examiner

FIG. 6B

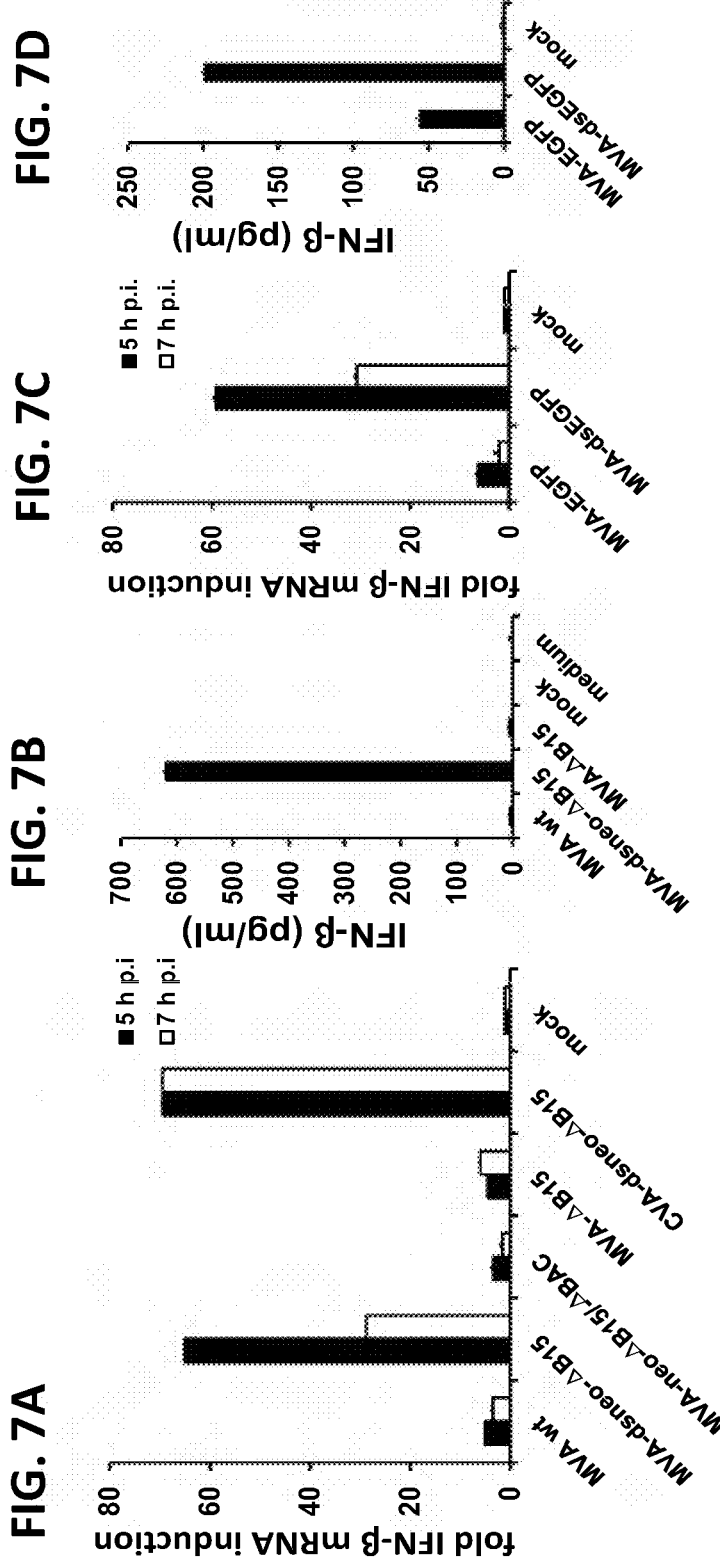

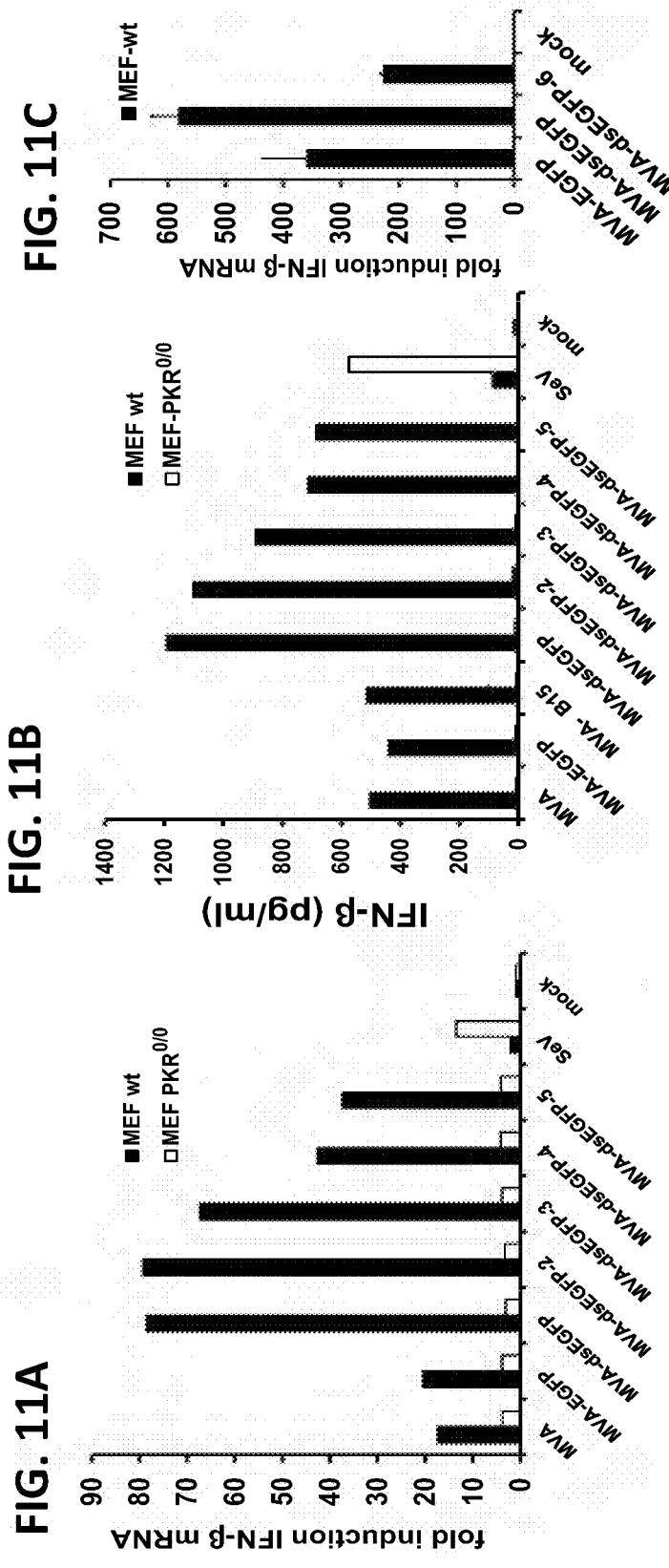

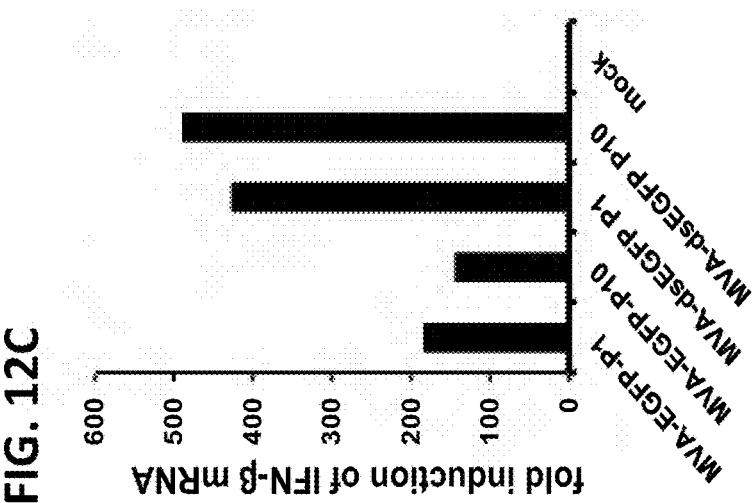
FIG. 12C
fold induction of IFN-β mRNA
FIG. 12B
Ratio viral output/input
■ MVA-EGFP
▨ MVA-dsEGFP
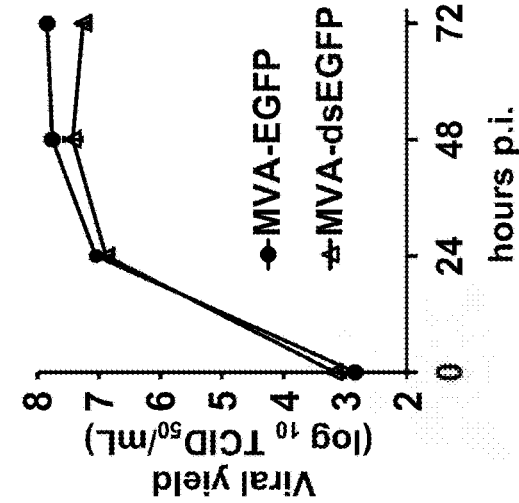
FIG. 12A
Viral yield (log₁₀ TCID₅₀/mL)
hours p.i.
◆ MVA-EGFP
▲ MVA-dsEGFP

FIG. 15

```
Monkeypox            --MMKMKMMVRIYFVSL------SLLLFHSYAI----DIENEITEFFN-----KMRDTLPAKDSK
Vaccinia-WR          ---MTMKMMVHIYFVSL------LLLLFHSYAI----DIENEITEFFN-----KMRDTLPAKDSK
Vaccinia-Copenhagen  ---MTMKMMVHIYFVSL------LLLLFHSYAI----DIENEITEFFN-----KMRDTLPAKDSK
CVA                  -MKMTMKMMVHIYFVSL------LLLLFHSYAI----DIENEITEFFN-----KMRDTLPAKDSK
Ectromelia           MMKMTMKMMVRIYFVSLSLSLSLLLFHSYAI----DIENEITEFFN-----KMRDTLPAKDSK
Cowpox               -MKMTMKMMVHIYFVSLSLSLSLLLFHSYAI----DIENEITEFFN-----KMKDTLPAKDSK
Camelpox             -MKMTMKMMVHIYFVFVSLS--LSLLLFHSYAI----DIENEITDFFN-----KMKDILPTKDSK
Swinepox             ---MISIK----KYN--------ILLFIISFIYCSADND--IDSLYE----GYKEFLDPKLKQ
Tanapox              ------MK----ITY--------IILLICKEIICDNSGDDMDYDYIANGNIDYLKTIDNDIIN
                         :*                   :  *:*  .         .          .    ..

Monkeypox            WLNPVCMFGGTMNDMAALGEPFSAKCPPIEDSLLSHRYK----DYVVKWERLEKNRRRQVS
Vaccinia-WR          WLNPACMFGGTMNDIAALGEPFSAKCPPIEDSLLSHRYK----DYVVKWERLEKNRRRQVS
Vaccinia-Copenhagen  WLNPACMFGGTMNDIAALGEPFSAKCPPIEDSLLSHRYK----DYVVKWERLEKNRRRQVS
CVA                  WLNPACMFGGTMNDIAALGEPFSAKCPPIEDSLLSHRYK----DYVVKWERLEKNRRRQVS
Ectromelia           WLNPSCMFGGTMNDMAALGEPFSAKCPPIEDSLLSHRYNDK-DNVVNWEKIGKTRR--PL
Cowpox               WLNPACMFGGTMNDMAAIGEPFSAKCPPIEDSLLSHRYKDK-DNVVNWEKIGKTRR--PL
Camelpox             WLNPACMFGGTTNDMAAIGEPFSAKCPPIEDSLLSHRYKNK-DNVVNWEKIGKTKR--PL
Swinepox             FLNDNCTYRGYRDFFLYNEEPANIKCPLLNDILLRQKYH---NYTILWKKLGERSSR---L
Tanapox              LVNKNCSFREIKTTLAKENEVLMLKCPQLDNYILPWKYMNRSEYTVTWKNISNSTEY---N
                     :.* . *         .    .  *** .   :* .:  : .   :   *  :::   :
```

FIG. 17A

```
Monkeypox            NKRVKHGDLWIANYTSKFSNRRYLCTVTTKNGDCVQGVVR-SHVWKPSSCIPKTYELGTY
Vaccinia-WR          NKRVKHGDLWIANYTSKFSNRRYLCTVTTKNGDCVQGIVR-SHIRKPPSCIPKTYELGTH
Vaccinia-Copenhagen  NKRVKHGDLWIANYTSKFSNRRYLCTVTTKNGDCVQGIVR-SHIKKPPSCIPKTYELGTH
CVA                  NKRVKHGDLWIANYTSKFSNRRYLCTVTTKNGDCVQGIVR-SHIKKPPSCIPKTYELGTH
Ectromelia           NRRVKNGDLWIANYTSNDSHRRYLCTVTTKNGDCVQGIVR-SHIRKPPSCIPETYELGTH
Cowpox               NRRVKNGDLWIANYTSNDSRRRYLCTVITKNGDCIQGIVR-SHVRKPSSCIPEIYELGTH
Camelpox             NRRVKNGDLWIANYTSNDSRRRYLCTAITKNGDCIQGIIR-SHVRKPSSCIPEIYELGTH
Swinepox             LNTHGSIFLDFFPYKSELRGSVYECMIILNN-TCDQFILKLNDIRSNPVCYHNDYK-----
Tanapox              NTRIENNMLMFFPFYNLQAGSKYLCTVSTNK-SCDQSVVIVKKSFYSNNCMLSEAK-----
                          *     ::         *        *              *        ..

Monkeypox            DKYGIDLYCGILYAKHYNNITWYKDNKEINIDDFKYSQAGK--ELIIHNPELEDSGRYDC
Vaccinia-WR          DKYGIDLYCGILYAKHYNNITWYKDNKEINIDDIKYSQTGK--ELIIHNPELEDSGRYDC
Vaccinia-Copenhagen  DKYGIDLYCGILYAKHYNNITWYKDNKEINIDDIKYSQTGK--ELIIHNPELEDSGRYDC
CVA                  DKYGIDLYCGILYAKHYNNITWYKDNKEINIDDIKYSQTGK--KLIIHNPELEDSGRYNC
Ectromelia           DKYGIDLYCGILYAKHYNNITWYKDNKEINIDDIKYSQTGK--KLIIHNPELEDSGRYNC
Cowpox               DKYGIDLYCGILYAKHYNNITWYKNNQELIIDGTKYSQSGQ--NLIIHNPELEDSGRYDC
Camelpox             DKYGIDLYCGIIYAKHYNNITWYKDNKEINIDDIKYSQTGK--ELIIHNPALEDSGRYDC
Swinepox             VHTNIEIFCNVINL-QYDYITWYKNNSEIIIDGYKYSNQSR--RLLVYNTTYNDSGIYYC
Tanapox              ENDNFEIYCGILHA-KYNTIKWFKEEKEITN-NYKYYTKLGGYVKGINNVTYSDSGKYVC
                     .    :.: ::   *  *.*:.:*    **               .  *   :***:  *
```

FIG. 17B

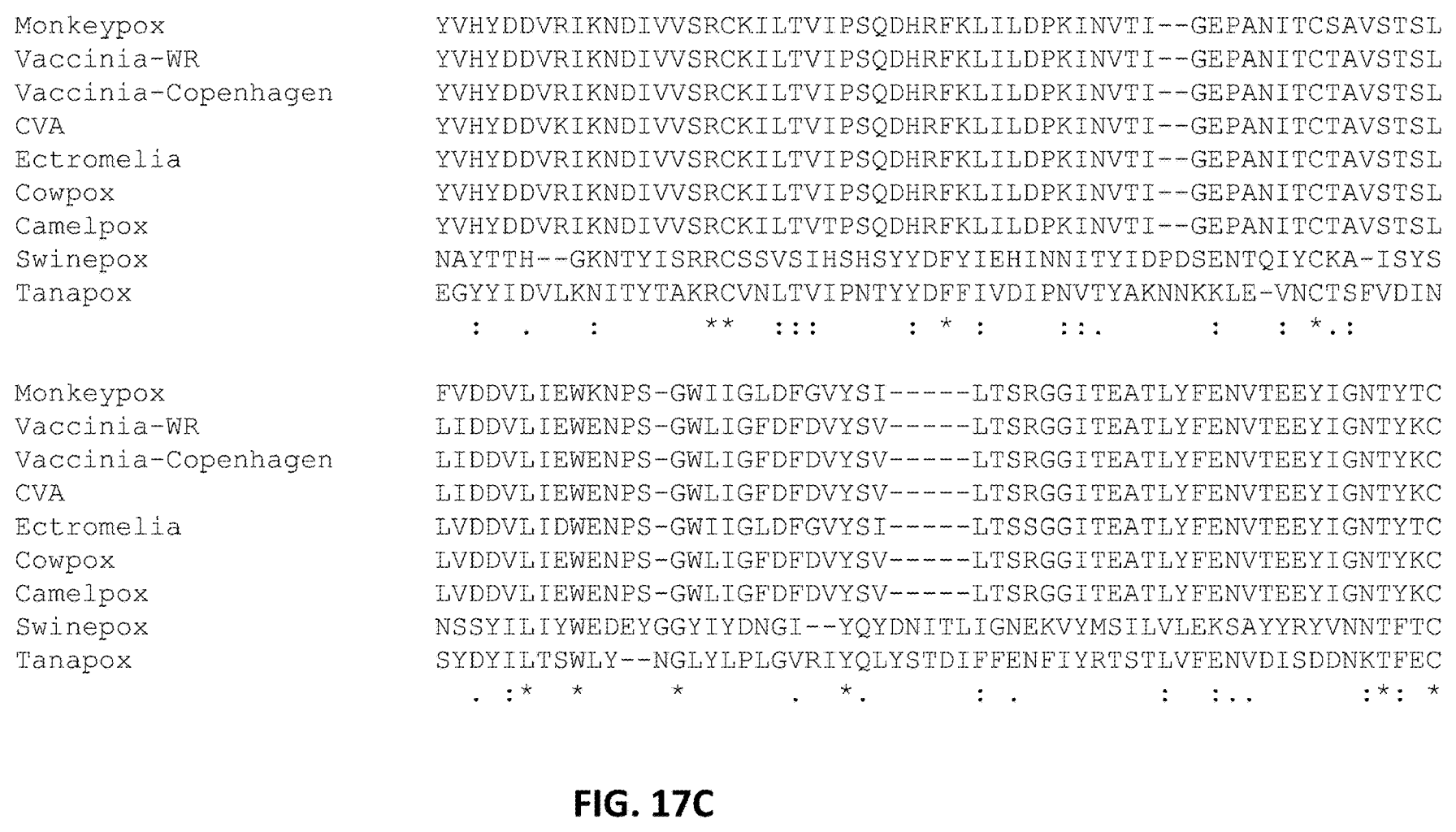

```
Monkeypox            YVHYDDVRIKNDIVVSRCKILTVIPSQDHRFKLILDPKINVTI--GEPANITCSAVSTSL
Vaccinia-WR          YVHYDDVRIKNDIVVSRCKILTVIPSQDHRFKLILDPKINVTI--GEPANITCTAVSTSL
Vaccinia-Copenhagen  YVHYDDVRIKNDIVVSRCKILTVIPSQDHRFKLILDPKINVTI--GEPANITCTAVSTSL
CVA                  YVHYDDVKIKNDIVVSRCKILTVIPSQDHRFKLILDPKINVTI--GEPANITCTAVSTSL
Ectromelia           YVHYDDVRIKNDIVVSRCKILTVIPSQDHRFKLILDPKINVTI--GEPANITCTAVSTSL
Cowpox               YVHYDDVRIKNDIVVSRCKILTVIPSQDHRFKLILDPKINVTI--GEPANITCTAVSTSL
Camelpox             YVHYDDVRIKNDIVVSRCKILTVTPSQDHRFKLILDPKINVTI--GEPANITCTAVSTSL
Swinepox             NAYTTH--GKNTYISRRCSSVSIHSHSYYDFYIEHINNITYIDPDSENTQIYCKA-ISYS
Tanapox              EGYYIDVLKNITYTAKRCVNLTVIPNTYDFFIVDIPNVTYAKNNKKLE-VNCTSFVDIN
                       ..      .         *  **     *      .    :  ::     :  * :   :: :.

Monkeypox            FVDDVLIEWKNPS-GWIIGLDFGVYSI-----LTSRGGITEATLYFENVTEEYIGNTYTC
Vaccinia-WR          LIDDVLIEWENPS-GWLIGFDFDVYSV-----LTSRGGITEATLYFENVTEEYIGNTYKC
Vaccinia-Copenhagen  LIDDVLIEWENPS-GWLIGFDFDVYSV-----LTSRGGITEATLYFENVTEEYIGNTYKC
CVA                  LIDDVLIEWENPS-GWLIGFDFDVYSV-----LTSRGGITEATLYFENVTEEYIGNTYKC
Ectromelia           LVDDVLIDWENPS-GWIIGLDFGVYSI-----LTSSGGITEATLYFENVTEEYIGNTYTC
Cowpox               LVDDVLIEWENPS-GWLIGFDFDVYSV-----LTSRGGITEATLYFENVTEEYIGNTYKC
Camelpox             LVDDVLIEWENPS-GWLIGFDFDVYSV-----LTSRGGITEATLYFENVTEEYIGNTYKC
Swinepox             NSSYILIYWEDEYGGYIYDNGI--YQYDNITLIGNEKVYMSILVLEKSAYYRYVNNTFTC
Tanapox              SYDYILTSWLY--NGLYLPLGVRIYQLYSTDIFFENFYRTSTLVFENVDISDDNKTFFEC
                       .  :*.  * .            *   .       .       ::   . . .:**:  ::
```

FIG. 17C

| | |
|---|---|
| Monkeypox | RGHNYYFDKTLTTTVVLE-- |
| Vaccinia-WR | RGHNYYFEKTLTTTVVLE-- |
| Vaccinia-Copenhagen | RGHNYYFEKTLTTTVVLE-- |
| CVA | RGHNYYFEKTLTTTVVLE-- |
| Ectromelia | RGHNYYFDKTLTTTVVLE-- |
| Cowpox | RGHNYYFEKTLTTTVVLE-- |
| Camelpox | RGHNYYFEKTLTTTVVLE-- |
| Swinepox | LATSVYVEKKTTTTLVIKKT |
| Tanapox | EALSVTLKKIKYTTIKVEK- |
| | .  .  . :  * .  *: :: |

FIG. 17D

|  | Ancestral WT | Vaccine WT | Vaccine Candidate | B.1 | Epsilon | Beta | Gamma | Delta | Omicron |
|---|---|---|---|---|---|---|---|---|---|
| Ancestral WT | 100.00 | 93.73 | 93.16 | 92.61 | 89.43 | 88.86 | 86.57 | 26.36 | 26.97 |
| Vaccine WT | 93.73 | 100.00 | 99.15 | 98.86 | 89.40 | 92.55 | 90.26 | 27.36 | 26.67 |
| Vaccine Candidate | 93.16 | 99.15 | 100.00 | 99.72 | 88.83 | 91.69 | 89.40 | 27.05 | 26.67 |
| B.1 | 92.61 | 98.86 | 99.72 | 100.00 | 88.60 | 91.45 | 89.17 | 26.97 | 26.67 |
| Epsilon | 89.43 | 89.40 | 88.83 | 88.60 | 100.00 | 91.60 | 89.01 | 28.27 | 26.59 |
| Beta | 88.86 | 92.55 | 91.69 | 91.45 | 91.60 | 100.00 | 97.46 | 27.66 | 26.59 |
| Gamma | 86.57 | 90.26 | 89.40 | 89.17 | 89.01 | 97.46 | 100.00 | 27.66 | 25.68 |
| Delta | 26.36 | 27.36 | 27.05 | 26.97 | 28.27 | 27.66 | 27.66 | 100.00 | 28.57 |
| Omicron | 26.97 | 26.67 | 26.67 | 26.67 | 26.59 | 26.59 | 25.68 | 28.57 | 100.00 |

FIG. 17E

COMPOSITIONS AND METHODS FOR INDUCING AN ENHANCED IMMUNE RESPONSE USING POXVIRUS VECTORS

FIELD

The invention provided herein relates to recombinant poxviruses comprising heterologous nucleic acids encoding complementary RNA forming double-stranded RNA (dsRNA) early in infection. Early dsRNA may also be generated by transcribing both strands of native genes of recombinant poxviruses. The recombinant poxviruses provided herein may further comprise heterologous nucleic acids encoding one or more costimulatory molecules, and/or heterologous nucleic acids encoding one or more infectious disease-associated antigens or tumor-associated antigens. These recombinant poxviruses enhance innate and adaptive immune activation in a subject compared to identical recombinant poxviruses lacking heterologous nucleic acids expressing early dsRNA. Also provided herein are pharmaceutical compositions comprising any of the recombinant poxviruses provided herein, as well as methods and uses of such recombinant poxviruses.

BACKGROUND

The immune system recognizes a variety of pathogens, including viruses, by means of pattern recognition receptors (PRRs), which detect pathogen-associated molecular patterns (PAMPs). PRRs encompass the family of Toll-like receptors (TLRs), RIG-like helicases (RLHs), NOD-like receptors (NLRs) and other hitherto less well defined PRRs (Iwasaki (2012), *Annu. Rev. Microbiol.* 66:177-196; Desmet & Ishii (2012), *Nat. Rev. Immunol.* 12:479-491; Melchjorsen (2013), *Viruses.* 5:470-527). Activation of PRRs leads to the activation of various immune cells, including dendritic cells (DCs), and the eventual induction of innate and adaptive immune responses. PRR activation also leads to the induction of an antiviral state in non-immune cells via the induction and action of type I interferons (IFNs), which include IFN-alpha (IFN-α) and IFN-beta (IFN-β), as well as the induction and action of other cytokines and chemokines, which alert as yet uninfected host cells and coordinate the immune response. Type I IFNs regulate many aspects of the immune response, including innate pathogen resistance mechanisms as well as antibody production and T-cell activation, e.g. by upregulating MHC class I and II expression, cross-presentation and activation of DCs (Iwasaki & Medzhitov (2010), *Science* 327:291-295; Desmet & Ishii (2012), *Nat. Rev. Immunol.* 12:479-491).

An important way for the organism to detect the presence of viruses is the recognition of viral RNA or DNA by both normal and immune cells. TLR3, TLR7/8, TLR9 and TLR13 have been identified as receptors for double-stranded RNA (dsRNA), single-stranded RNA (ssRNA), DNA, and ribosomal RNA (rRNA), respectively. Viruses with double-stranded DNA (dsDNA) genomes like herpesviruses, adenoviruses and poxviruses are recognized by TLR9-dependent and TLR9-independent pathways (Hochrein et al. (2004), *Proc. Natl. Acad. Sci. U.S.A* 101:11416-11421; Samuelsson et al. (2008), *J. Clin. Invest* 118:1776-1784). Previous work has shown that poxviruses potently inhibit both TLR9-dependent and TLR9-independent pathways of dsDNA recognition.

Detection of poxviral DNA by immune cells via TLR9 leads to production of type I interferons (i.e., IFN-α/β) and type-III interferons (i.e., IFN-λ), as well as of other cytokines and chemokines (Lauterbach et al. (2010), *J. Exp. Med.* 207:2703-2717; Samuelsson et al. (2008), *J. Clin. Invest* 118:1776-1784). Plasmacytoid DCs (pDCs) are selectively competent to produce large amounts of IFN-I and IFN-III in response to TLR7/8- or TLR9-dependent stimulation. In pDC, TLR9-dependent stimulation leads to IFN-I and IFN-III production. Both DNA and other viral nucleic acids are recognized in the cytoplasm of infected cells, thereby alerting those cells to produce IFN-I and IFN-III, among other cytokines. TLR9-independent pathways of poxvirus recognition are mainly employed by the various subsets of conventional dendritic cells (cDC) (Hochrein & O'Keeffe (2008) *Handbook Exp Pharmacol* 183:153-179).

Another important signature of viral infection is dsRNA, which is not only generated during infection of cells by RNA viruses, but also by poxviruses, which have a dsDNA genome. The dsRNA in poxvirus infection is generated by overlapping transcription from genes located on both the upper and lower strand of the dsDNA genome. In particular, the termination of transcription of intermediate and late genes is not tightly regulated, a phenomenon leading to viral mRNA with long 3' untranslated regions (3' UTRs) of heterogeneous lengths (Cooper, Wittek, and Moss (1981), *J. Virol.* 39:733-745; Xiang et al. (1998), *J. Virol.* 72:7012-7023). When such transcripts originate from two neighboring genes in opposite orientation (i.e., that are transcribed towards each other), transcription produces overlapping, complementary mRNA stretches that form dsRNA by annealing with each other or with early transcripts (Boone, Parr, and Moss (1979), *J Virol.* 30:365-374). Generation of viral dsRNA appears to be largely confined to the late phase of the poxviral replication cycle (Colby & Duesberg (1969), *Nature* 222:940-944; Duesberg & Colby (1969), *Proc. Natl. Acad. Sci U.S.A* 64:396-403; Moss (2007), 5:2905-2945). It has previously been reported that dsRNA from viral transcripts can be found early in infection (Boone, Parr, and Moss (1979), *J Virol.* 30:365-374; Lynch et al. (2009), *Virology* 391:177-186; Willis et al. (2009), *Virology* 394:73-81; Willis, Langland, and Shisler (2011), *J. Biol. Chem.* 286:7765-7778). However, there appears to exist a selective pressure that prevents the generation of sufficient amounts of early dsRNA to trigger the cell's recognition systems, e.g., by securing efficient transcription termination of adjacent early genes transcribed in opposite directions (Smith, Symons, and Alcami (1998), *Seminars in Virology* 8:409-418). Poxviruses have evolved a specific early termination signal with the sequence TTTTTNT on the coding strand that terminates early transcription 20 to 50 nucleotides downstream of this sequence (Yuen & Moss (1987), *Proc. Natl. Acad. Sci U.S.A* 84:6417-6421). Early genes transcribed towards each other typically contain multiple termination signals indicating that tight control of early transcription termination shortly of such genes to avoid production of complementary RNAs early in infection appears to be important for viral fitness.

Host cells and organisms have devised a variety of recognition receptors for dsRNA to detect viral infection. While TLR3 is mainly expressed in immune cells and can sense extracellular dsRNA, most other dsRNA sensors like RIG-I, MDA-5, DDX1/DDX21/DHX36, protein kinase R (PKR), and 2"-5"-oligoadenylate synthetase (2"-5"-OAS), are ubiquitously expressed in the organs and cell types of the host and are localized in the cell cytoplasm. With respect to IFN type I induction, RIG-I and MDA-5 are considered to represent the most important cytosolic dsRNA sensors to detect viral infection (Melchjorsen (2013), *Viruses.* 5:470-527). Another important ds RNA sensor, the dsRNA-activated protein kinase R (PKR) is thought to exert its antiviral role mainly via phosphorylation of the translation elongation factor eIF2α, which leads to a shutdown of cellular and viral translation, thereby restricting viral replication. (Garcia et al. (2006), *Microbiol. Mol. Biol. Rev.* 70:1032-1060; Williams (1999), *Oncogene* 18:6112-6120). There is also evidence that PKR has a role in the induction of type I IFN. (Barry et al. (2009), *J Gen. Virol.* 90:1382-1391; Gilfoy & Mason (2007), *J Virol.* 81:11148-11158).

To inhibit antiviral effects triggered by dsRNA, poxviruses have devoted at least two proteins, E3 and K3, to the inhibition of the important dsRNA sensor PKR. Both viral proteins have been studied extensively. Among them, E3 appears to be central. E3 binds and sequesters dsRNA and inhibits PKR activation. Vaccinia virus (VACV) mutants lacking the E3L gene (VACV-ΔE3L) have a restricted host range and induce apoptosis in many cell types (Hornemann et al. (2003), *J. Virol.* 77:8394-8407; Kibler et al. (1997), *J Virol.* 71:1992-2003), suggesting that PKR-mediated apoptosis is the major outcome of PKR activation in VACV-infected cells. However, higher sensitivity of VACV-ΔE3L to IFNI treatment (Beattie, Paoletti, and Tartaglia (1995), *Virology* 210:254-263) and higher IFN-α/β induction in pre-apoptotic cells infected with E3-deleted VACV mutants has also been reported (Hornemann et al. (2003), *J. Virol.* 77:8394-8407). Here, we describe a method to induce PKR activation in cells infected with modified vaccinia virus Ankara (MVA) and chorioallantois vaccinia virus Ankara (CVA) without inducing detectable cell death or apoptosis, but triggering the release of high amounts of IFN-α/β and other chemokines and cytokines. This was achieved by expressing dsRNA early in infection before the onset of DNA replication. Stable expression of dsRNA was achieved by transcription of two complementary mRNAs from two independent insertions of a recombinant gene. In the case of CVA, IFN type I induction led to an almost non-pathogenic infection in mice, and that result depended on the presence of a functional type I IFN system.

MVA was developed by >570 passages of the fully replication-competent smallpox vaccine strain chorioallatois vaccinia virus Ankara (CVA) (Meisinger-Henschel et al. (2007), *J. Gen. Virol.* 88:3249-3259) on chicken embryo fibroblasts. Replication-competent CVA was shown to be poorly IFN-I inducing whereas replication-restricted MVA rather efficiently induced IFN-I (Samuelsson et al. (2008), *J. Clin. Invest* 118:1776-1784). CVA inhibition of IFN-I production was mediated in part by the poxvirus IFN-I-binding protein (IFN-IR) encoded by the B19R gene. The B19 protein binds to IFN-α and thus inhibits its bioactivity. In addition, binding of B19 to type I interferons also prevents the detection of IFN-α/β by antibody-based analysis techniques, indicating that B19 protein also binds human IFN-β. In contrast to the human system, B19 does not bind mouse IFN-β. Homologues of the poxvirus IFN-I-binding protein encoded by B19R ORF are present in a number of poxviral species, suggesting that this mechanism for inhibiting IFN-I activity is conserved in poxviruses more generally. See, e.g., FIG. 17.

IFN type I binding activity of B19 is not the only inhibitory mechanism employed by poxviruses to suppress IFN-I effector functions or induction. Poxviruses encode a number of factors subverting the interferon type I system of their hosts. Interferons are pivotal in antiviral defense because they induce an antiviral state in IFN receptor-expressing cells and regulate the innate and adaptive immune response of the host. Among the known poxviral factors counteracting the interferon system are the secreted receptor-like proteins B19 and B8 that bind and neutralize type I and type II interferons, respectively. Other poxviral proteins such as VACV E3, K7, C6, N1, C7, K1, K3 and H1 inhibit the induction of type I interferon or block interferon signaling and effector pathways. The fact that poxviruses encode such a multitude of proteins to counteract the interferon system highlights the importance of this system of innate immune defense for the control and eventual clearance of poxviruses by the infected host organism. Apart from the interferon system, orthopoxviruses encode other immune-modulating proteins interfering with induction or function of cytokines like IL-1β, IL-18, and of chemokines including VACV B16R, WR013, C23L/vCCI. These cytokines are also important in restricting pathogen spread and protecting the host from severe pathogen-induced damage. Poxviral proteins subverting pattern recognition pathways are universally efficient in thwarting induction of IFNs as well as of other cytokines and chemokines.

Accordingly, it is a primary objective of the invention to enhance recognition of poxviruses by cellular dsRNA sensors, as well as to increase the innate immune activation induced by MVA. Disclosed herein are recombinant poxviruses engineered to produce dsRNA early in infection by inserting two partially identical DNAs at two separate locations in the genome. Those DNAs are operable linked to strong early promoters oriented such that one DNA produces a 'sense' transcript and the other produces a complementary 'antisense' transcript. The two partially or completely complementary transcripts subsequently anneal to produce dsRNA. Efficient induction of IFN-β, an important marker of innate immune activation, was observed with early dsRNAs over a wide size range, with decreasing efficiencies as the complementary transcripts were shortened down to 50 bp.

SUMMARY

The invention encompasses a recombinant poxvirus comprising heterologous nucleic acids expressing excess double-stranded RNA (dsRNA) early in infection. In one embodiment, the invention encompasses a method of enhancing innate immune activation comprising administering the recombinant poxvirus to a vertebrate subject, wherein said administration enhances production of type I interferons (type I IFNs), cytokines and chemokines in the subject.

In a further embodiment, the recombinant poxvirus transcribes sense and antisense RNAs from both strands of a native poxvirus sequence, preferably an early gene, more preferably an immediate-early gene.

In a further embodiment, the recombinant poxvirus transcribes heterologous nucleic acid as sense and antisense RNAs from both strands of the heterologous sequence.

In a further embodiment, the invention encompasses a method of attenuating standard replication-competent vaccinia virus strains and of other species derived from chordopoxvirinae by expression of excess early dsRNA.

In various embodiments, the poxvirus further comprises heterologous sequences encoding one or more costimulatory molecules.

In various embodiments, the poxvirus further comprises heterologous sequences encoding one or more bacterial, viral, fungal, parasite, or tumor antigens.

In various embodiments, the poxvirus is an orthopoxvirus, a parapoxvirus, a yatapoxvirus, an avipoxvirus, a leporipoxvirus, a suipoxvirus, a capripoxvirus, a cervidpoxvirus, or a molluscipoxvirus. The orthopoxvirus may be selected from the group consisting of vaccinia virus, cowpox virus, and monkeypox virus. The vaccinia virus may be a modified vaccinia virus Ankara (MVA), e.g. modified vaccinia virus Ankara Bavarian Nordic (MVA-BN).

In various embodiments, the heterologous or endogenous nucleic acids generating dsRNA comprise sequences encoding partially or completely complementary RNA transcripts, wherein the complementary portions of RNA transcripts anneal after transcription to form dsRNA.

In various embodiments, the heterologous nucleic acids encoding completely or partially complementary RNA transcripts are identical within the complementary region, or have a similarity of more than 99%, of more than 95%, of more than 90%, of more than 80%, or of more than 70% within the complementary region.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIG. 2A) and FIG. 2B) show the results of independent experiments employing different sets of CVA mutants. Animals were inspected daily and weighed at the indicated days. Body weight data are expressed as percentage of mean weights+/−SEM of the respective group from the initial mean weight at day 0. Daggers indicate number of dead animals at the respective days. FIG. 2C) Lungs of 6-8 week-old female BALB/c mice infected intranasally with 10$^7$ TCID$_{50}$ of purified stock of the indicated viruses were recovered at six days post-infection. Lungs were homogenized and viral titers were determined by a standard TCID$_{50}$ assay using CV-1 cells. Indicated are the averages of total viral titers in lungs of two independent experiments from a total of 8 mice per virus. ***=p<0.001 by Student's t test.

FIG. 3A) The indicated numbers of 9-18 week-old C57BL/6-IFNAR$^{0/0}$ mice of both sexes were infected intranasally with a 50 μl inoculum containing 2×10$^6$ TCID$_{50}$ of crude viral stocks or 10$^7$ TCID$_{50}$ of purified stock of CVA and CVA-dsneo-ΔB15. Animals were inspected daily and weighed at the indicated days. Body weight data are expressed as percentage of mean weights+/−SEM of the respective group from the initial mean weight at day 0. FIG. 3B) Survival of mice shown in FIG. 3A).

FIG. 5A) Murine BALB/3T3 A31 cells were mock-infected or infected with purified stocks of BAC-derived MVA or CVA wild-type and the CVA mutants CVA-dsneo-ΔB15 and CVA-ΔB15 at an MOI of 10 for the indicated times. Cells were lysed and RNA from cell lysates was prepared using the QIAGEN RNeasy kit. Contaminating genomic DNA was eliminated using DNA removal (gDNA) columns from QIAGEN followed by an additional DNAse treatment with Turbo-DNAse (Ambion) for 1 hour at 37° C. and subsequent heat inactivation of the DNAse at 65° C. for 10 minutes. IFN-β mRNA levels were determined using a commercial gene expression assay for murine IFN-β (Applied Biosystems, Darmstadt, Germany). Shown are the levels of IFN-β transcript in infected cells relative to the level of IFN-β mRNA in mock-infected cells expressed as fold increase in IFN-β mRNA. FIG. 5B) A31 cells were mock-infected or infected with crude stocks of CVA and the indicated CVA mutants (see FIG. 1 for overview) at an MOI of 10 for 6 hours. RNA preparation of quantification of IFN-β mRNA was conducted as described in FIG. 5A). Shown are the levels of IFN-β transcript in infected cells relative to the level of IFN-β mRNA in mock-infected cells expressed as fold increase in IFN-β mRNA. 1: CVA; 2: CVA-dsneo-ΔB15/B19; 3: CVA-dsneo-ΔB15; 4: CVA-ΔB15; 5: CVA-zeo-ΔB15; 6: CVA-Δp$_{B15}$-neo-ΔB15; 7: mock.

FIGS. 6A and 6B shows a schematic representation of EGFP and neo insertions of dsRNA-producing MVA mutants. The direction of transcription of the neo and EGFP coding sequences (black arrows) controlled by the pS, pHyb or pB15R promoters is indicated. ORFs and all other elements are not drawn to scale. FIG. 6A) The neo ORF is part of the neo-IRES-EGFP selection cassette within the BAC cassette (Meisinger 2010). The latter is inserted into the intergenic region (IGR) I3L/I4L (MVA064/065). The neo-IRES-EGFP cassette is transcribed under control of the pS promoter (indicated by an arrow), whereas the neo/rpsL cassette in the B15R locus is transcribed in reverse orientation under the control of the B15R promoter. Neo ORFs within one MVA construct overlap by 792 nt (indicated by a grey box) with one single mismatch. In MVA-dsneo-ΔB15/ΔBAC, the complete BAC cassette in IGR I3L/4L was deleted via Cre/lox recombination. FIG. 6B) All MVA-dsEGFP constructs in FIG. 6B) are based on an MVA recombinant from which the neo-IRES-EGFP cassette within the BAC cassette had been deleted. In MVA-EGFP, the neo-IRES-EGFP cassette was replaced by a neo gene. The EGFP ORF transcribed in sense orientation in MVA-EGFP is inserted in the IGR between ORFs A25L and A26L (MVA136/137), whereas the EGFP ORF transcribed in antisense is inserted in IGR J2R/J3R (MVA086/087). The potential dsRNA stretches formed by the overlapping complementary EGFP transcripts are indicated by grey bars. Neighboring ORFs are only indicated for MVA-EGFP and MVA-dsEGFP. The lacZα sequence at the 3"end of the antisense EGFP transcript is solely inserted in MVA-dsEGFP and served as a non-complementary 3'overhang to match the constellation of complementary neo transcripts in MVA-dsneo-ΔB15. MVA-EGFP contains an additional neo insert flanked by FRT sites under control of a bacterial promoter downstream of the EGFP ORF. This selection marker was removed in all MVA-dsEGFP constructs by FLP/FRT recombination.

FIGS. 7A, 7B, 7C, and 7D show the induction of IFN-β mRNA and protein expression in murine A31 cells by dsRNA-producing MVA mutants. Murine BALB/3T3 A31 cells were mock-infected or infected with crude virus preparations of MVA-wt or the indicated mutants of MVA expressing single or overlapping transcripts of neo (FIG. 7A, FIG. 7B) or EGFP (FIG. 7C, FIG. 7D). Cells in FIG. 7A and FIG. 7C were infected for 5 hours (black bars) and 7 hours (grey bars) before harvest for IFN-β transcript analysis. IFN-β gene induction by CVA-dsneo-ΔB15 infection is shown reference in FIG. 7A. RNA from cell lysates was prepared using the QIAGEN RNeasy kit. Contaminating DNA was eliminated using DNA removal (gDNA) columns from QIAGEN followed by an additional DNAse treatment with Turbo-DNAse (Ambion) for 1 hour at 37° C. and subsequent heat inactivation of the DNAse at 65° C. for 10 minutes. IFN-β mRNA levels were determined by RT-qPCR using a commercial gene expression assay for murine IFN-β (Applied Biosystems). Absence of contaminating DNA was demonstrated by negative RT-qPCR results when the RT enzyme was omitted in the RT reaction. Shown are the levels of IFN-β transcript in infected cells relative to the level of IFN-β mRNA in mock-infected cells. IFN-β Ct values were normalized using the Ct values for cellular 18S rRNA. IFN-β protein levels were determined in supernatants of cells infected for 18 hours (FIG. 7B) or 23 hours (FIG. 7D). Supernatants were harvested and assayed for murine IFN-β using a commercially available ELISA (PBL). Infections shown in FIG. 7A and FIG. 7C were from one experiment while experiments shown in FIG. 7B) and FIG. 7D) were independent. FIG. 7A) 1: MVA wt; 2: MVA-dsneo-ΔB15; 3: MVA-dsneo-ΔB15/-ΔBac; 4: MVA-ΔB15, 5: CVA-dsneo-ΔB15; 6: mock. FIG. 7B) 1: MVA wt; 2: MVA-dsneo-ΔB15; 3: MVA-ΔB15; 4: mock, 5: medium. FIG. 7C) 1: MVA-EGFP; 2: MVA-dsEGFP; 3: mock. FIG. 7D) 1: MVA-EGFP; 2: MVA-dsEGFP; 3: mock.

Figures 8A, 8B:
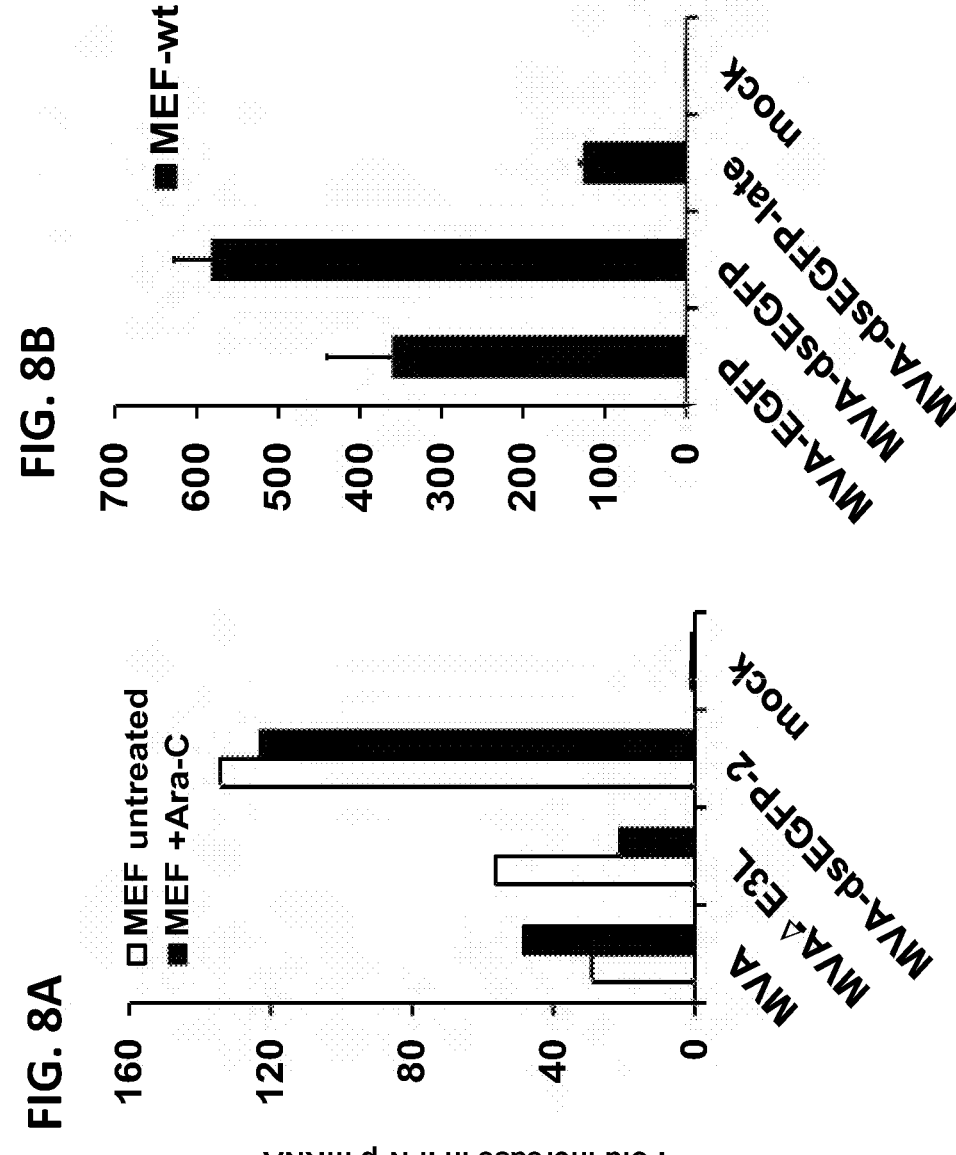

FIGS. 8A and 8B show the induction of IFN-β mRNA expression by MVA-dsEGFP depending on timing of dsRNA generation. Shown are the levels of IFN-β transcript in infected cells relative to the level of IFN-β mRNA in mock-infected cells expressed as "Fold increase in IFN-β mRNA." FIG. 8A) Wt-MEFs were mock-infected or infected with purified stocks of MVA-EGFP (reference virus, containing only one EGFP insert generating a sense transcript), MVA-dsEGFP-2 as positive control, or MVA-ΔE3L (lacking the gene encoding the viral dsRNA binding protein E3) at an MOI of 10 for 5 hours. Cells were either left untreated (black bars) or treated with 40 µg/ml final concentration of cytosine arabinoside (AraC, white bars), which blocks viral DNA replication and arrests infection in the early phase. RNA from cell lysates was prepared and analyzed by RT-qPCR for levels of IFN-β mRNA as described in the legend to FIG. 7. FIG. 8B) Wt-MEFs were mock-infected or infected with crude stocks of MVA-EGFP, MVA-dsEGFP, or MVA-dsEGFP-late, which expresses the antisense EGFP cassette under control of a strong and exclusively late promoter (SSL) developed by Bavarian Nordic, for 5 h. RNA from cell lysates was prepared and analyzed by RT-qPCR for levels of IFN-β mRNA as described in the legend to FIGS. 7A, 7B, 7C, and 7D.

Figure 9:
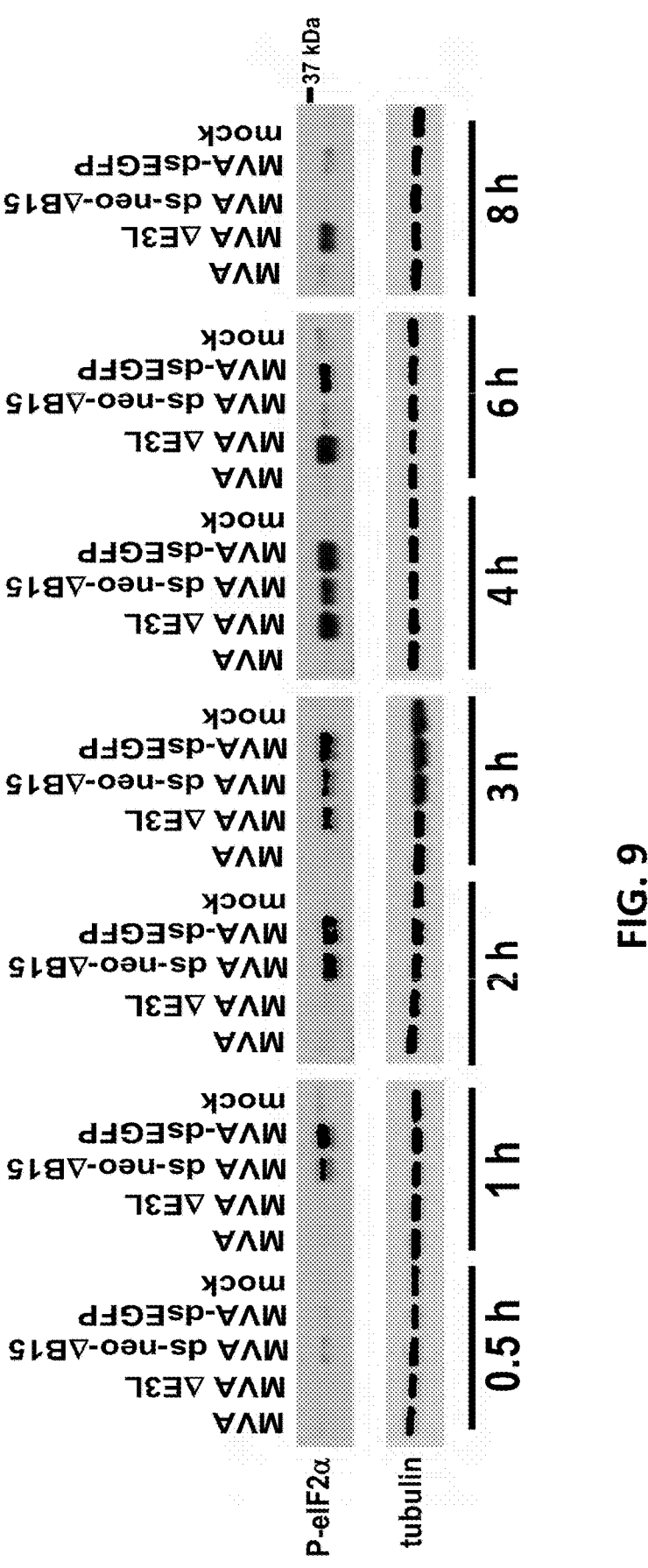

FIG. 9 shows the activation of PKR by MVA-dsneo-ΔB15 and MVA-dsEGFP in A31 cells. Murine A31 cells were infected at day 1 after seeding with crude stocks of the indicated viruses at an MOI of 10. Phosphorylation of eIF2α (P-eIF2α) in cell lysates prepared after the indicated times of infection was analyzed by immunoblot using an antibody against the phospho-epitope Ser51 of eIF2α (antibody #9721, Cell Signaling Technology Inc., Danvers, MA, USA) at a 1:1000 dilution. As loading control, a separate portion of the immunoblot membrane was developed with an antibody detecting mouse β-tubulin isotype I.

Figure 10B:
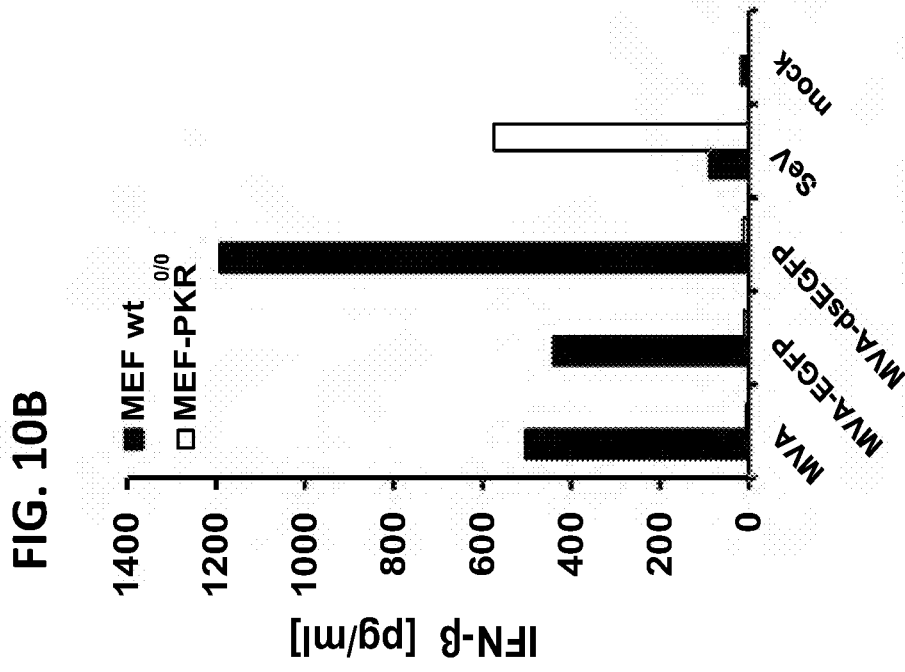
Figure 10A:
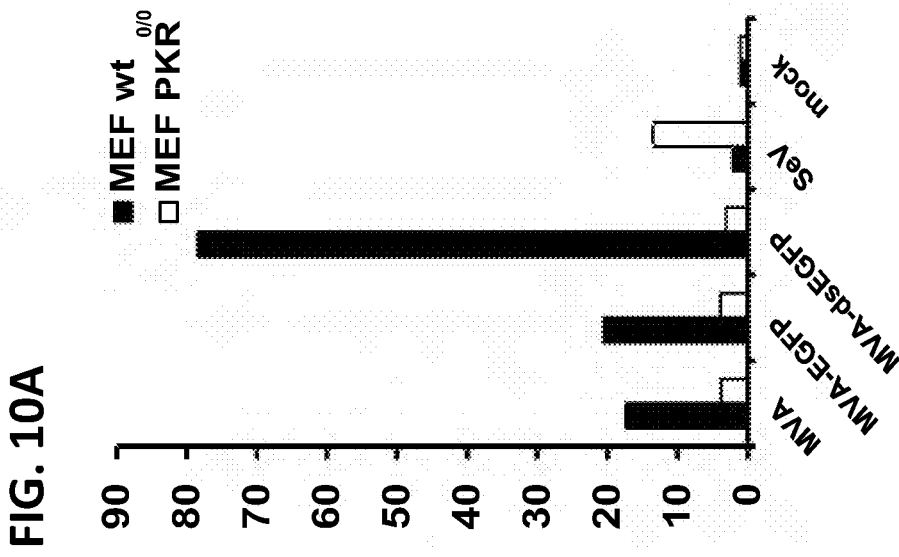

FIGS. 10A and 10B show that increased induction of IFN-β mRNA by MVA-dsEGFP in MEFs depends on PKR. Wt-MEFs and PKR-deficient (PKR$^{o/o}$) MEFs were mock-infected or infected with purified stocks of MVA-EGFP or MVA-dsEGFP at an MOI of 10 for 5 hours. One ml of a 1:100 dilution of a commercially available Sendai virus (SeV) preparation was used as positive control for PKR-independent but dsRNA-dependent IFN-β induction. FIG. 10A) RNA from cell lysates was prepared and analyzed by RT-qPCR for levels of IFN-β mRNA as described in the legend to FIG. 7. Shown are the levels of IFN-β transcript relative to the level of IFN-β mRNA in mock-infected cells expressed as "Fold increase in IFN-β mRNA". 1: MVA; 2: MVA-EGFP; 3: MVA-dsEGFP; 4: SeV; 5: mock. FIG. 10B) IFN-β protein levels were determined in supernatants of cells infected for 24 hours. Supernatants were harvested and assayed for murine IFN-β using a commercially available ELISA (PBL). 1: MVA; 2: MVA-EGFP; 3: MVA-dsEGFP; 4: SeV; 5: mock.

FIGS. 11A, 11B, and 11C show the length requirements of PKR-dependent induction of IFN-β by dsRNA-producing MVA recombinants. Wt-MEFs and PKR$^{o/o}$-MEFs were mock-infected or infected with crude stocks of MVA-EGFP or the indicated EGFP-dsRNA mutants having progressively shortened EGFP ORF overlaps (see FIG. 6B) at an MOI of 10 for 5 hours (FIG. 11A, FIG. 11C) or 24 hours (FIG. 11B) at 37° C. One ml of a 1:100 dilution of a commercially available Sendai virus (SeV) preparation was used as positive control for dsRNA-dependent but PKR-independent IFN-β induction. Fold induction of IFN-β mRNA over mock was determined by RT-qPCR using total RNA isolated from cells as described in the legend to FIG. 7. Ct values for IFN-β mRNA were corrected with Ct values for 18S rRNA, which served as endogenous control. FIG. 11B) IFN-β protein levels were determined in supernatants of wt MEFs and PKR$^{o/o}$-MEFs infected for 24 hours with the indicated MVA recombinants. Supernatants were harvested and assayed for murine IFN-β using a commercially available ELISA (PBL). MVA-ΔB15 was included as an additional reference. FIG. 11A) 1: MVA; 2: MVA-EGFP; 3: MVA-dsEGFP; 4: MVA-dsEGFP-2; 5: MVA-dsEGFP-3; 6: MVA-dsEGFP-4; 7: MVA-dsEGFP-5; 8: SeV; 9: mock. FIG. 11B) 1: MVA; 2: MVA-EGFP; 3: MVA-ΔB15; 4: MVA-dsEGFP; 5: MVA-dsEGFP-2; 6: MVA-dsEGFP-3; 7: MVA-dsEGFP-4; 8: MVA-dsEGFP-5; 9: SeV; 10: mock. FIG. 11C) 1: MVA-EGFP; MVA-dsEGFP; 3: MVA-dsEGFP-6; 4: mock.

FIGS. 12A, 12B, and 12C show replication and phenotypic stability of MVA-dsEGFP. FIG. 12A) For analysis of replication behavior of MVA-EGFP and MVA-dsEGFP, monolayers of $10^6$ secondary CEF cells were infected with these viruses in triplicate at a MOI of 0.025 (multi-cycle analysis). Viral output at the indicated times is plotted, each data point represents results from three independent wells. FIG. 12B) Monolayers of $10^6$ human HeLa and HaCaT cells, and monkey CV-1 cells were infected in triplicate at a MOI of 0.025 with MVA-EGFP or MVAds-EGFP. The ratio of the viral output at day three post-infection. versus the input of $5 \times 10^4$ TCID$_{50}$ per well is plotted. Each data point represents single titration results from three independent wells. FIG. 12C) Monolayers of secondary CEF cells were infected at an MOI of 10 for 5 hours with the indicated viruses passaged once (P1) or 10 times (P10) in DF-1 cells as described in the text. Fold induction of IFN-β mRNA in infected cells over mock was determined by RT-qPCR using total RNA isolated from cells as described in the legend to FIG. 7. 1: MVA-EGFP-P1; 2: MVA-EGFP-P10; 3: MVA-dsEGFP P1; 4: MVA-dsEGFP P10; 5: mock.

Figure 13A:
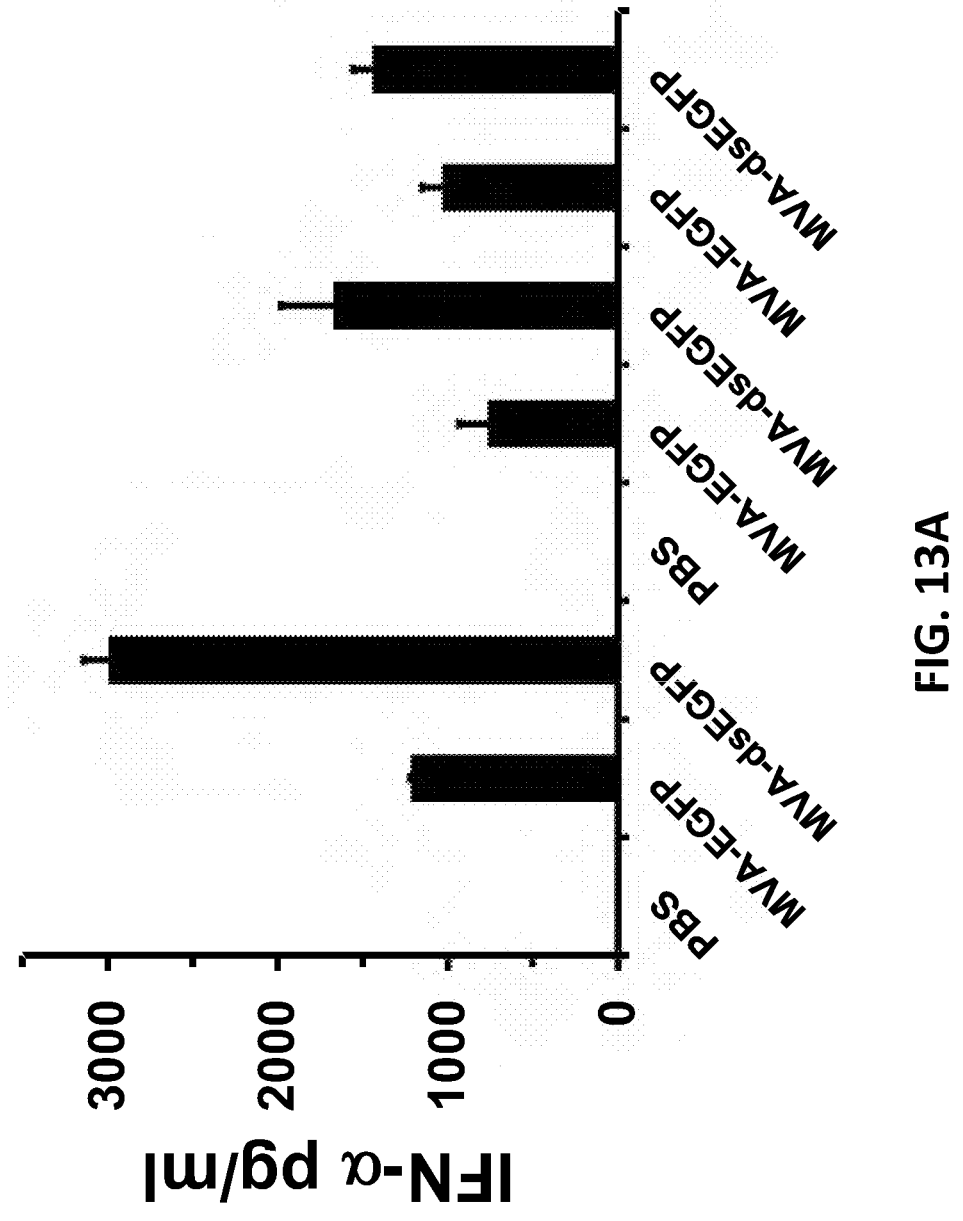
Figure 13B:
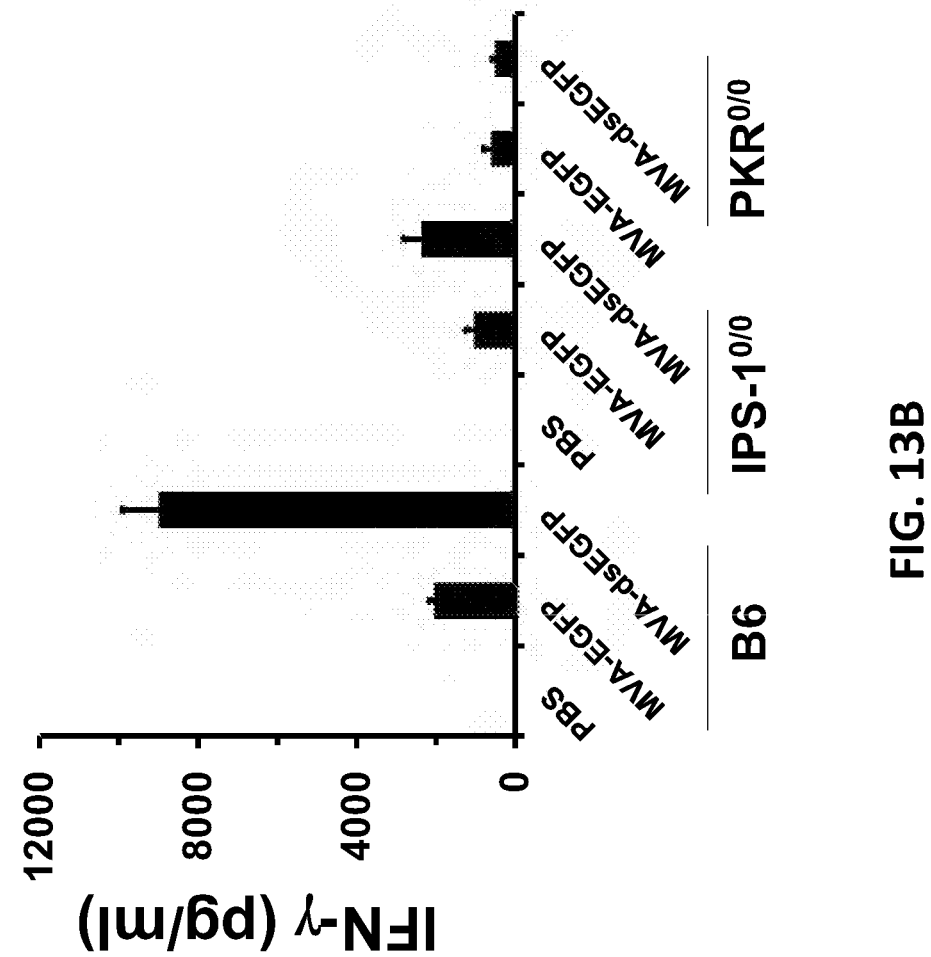
Figure 13C:
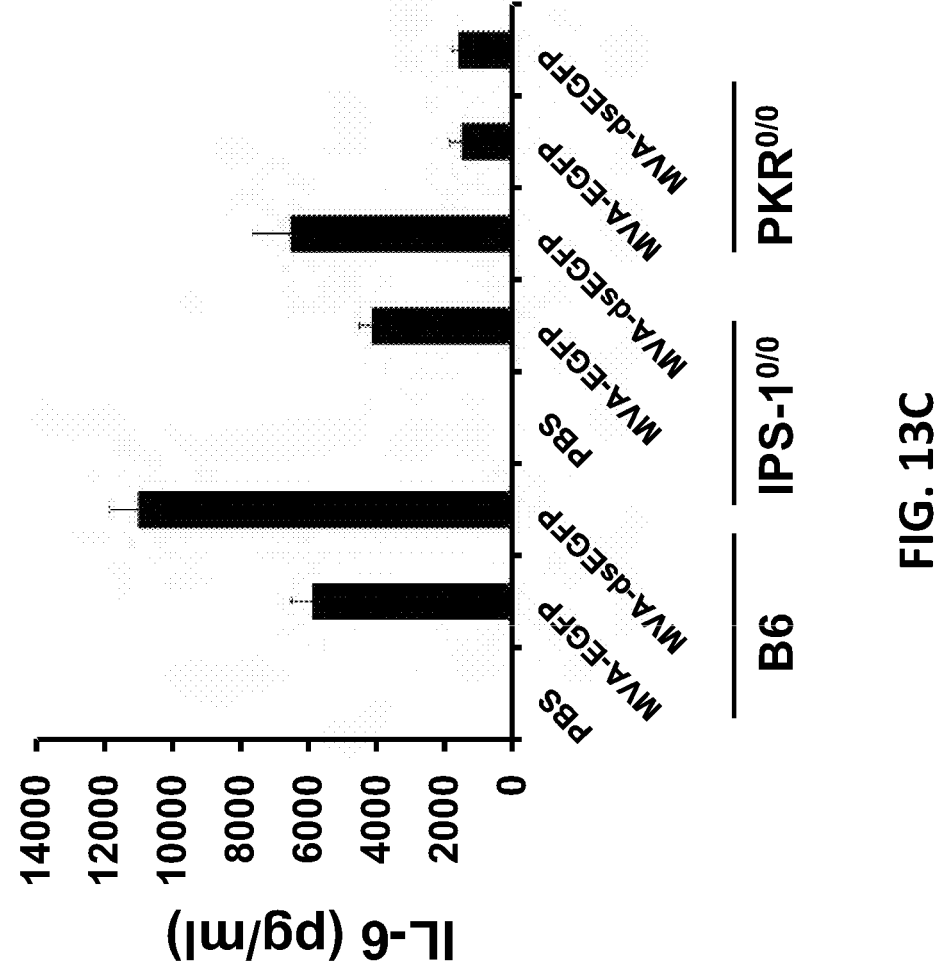
Figure 13D:
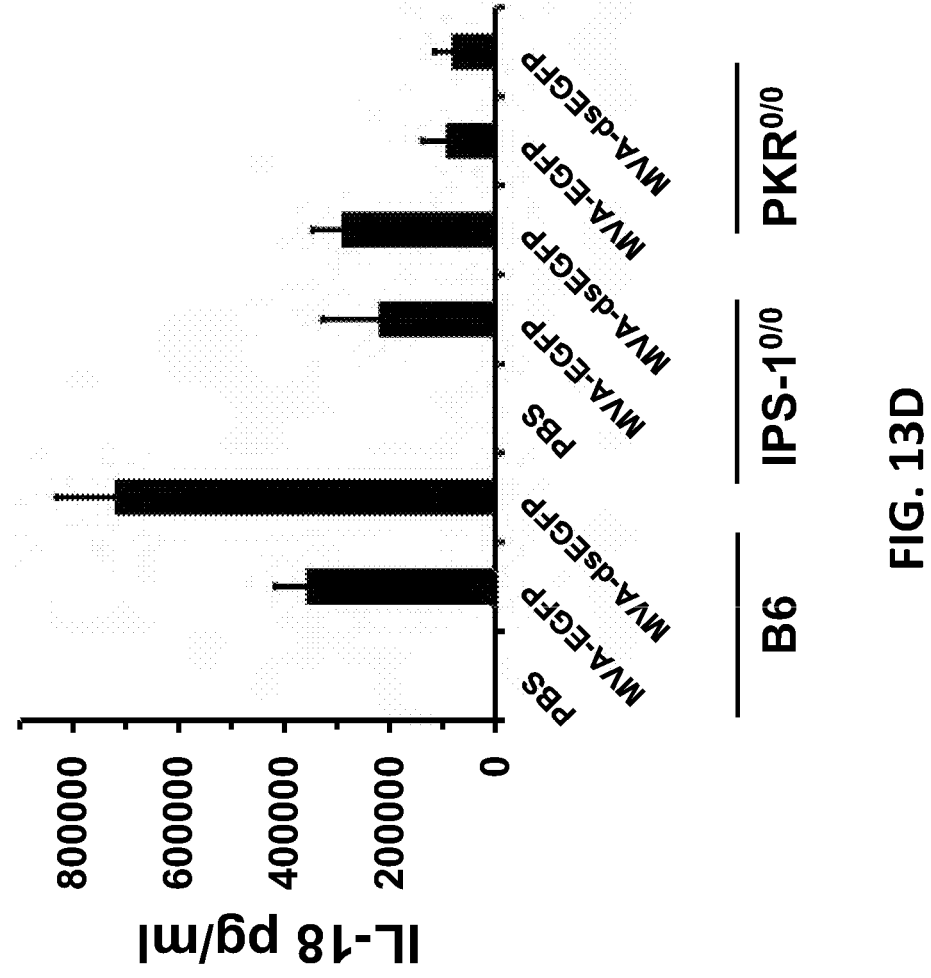
Figure 13E:
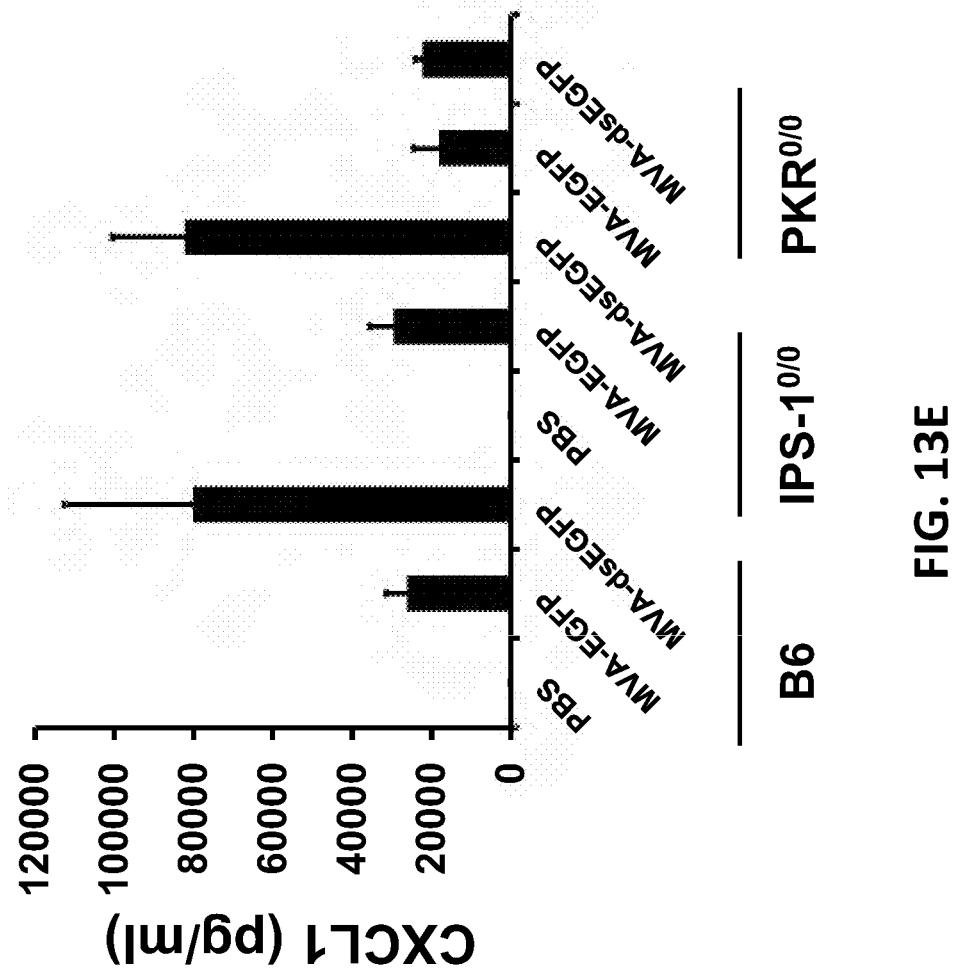
Figure 13F:
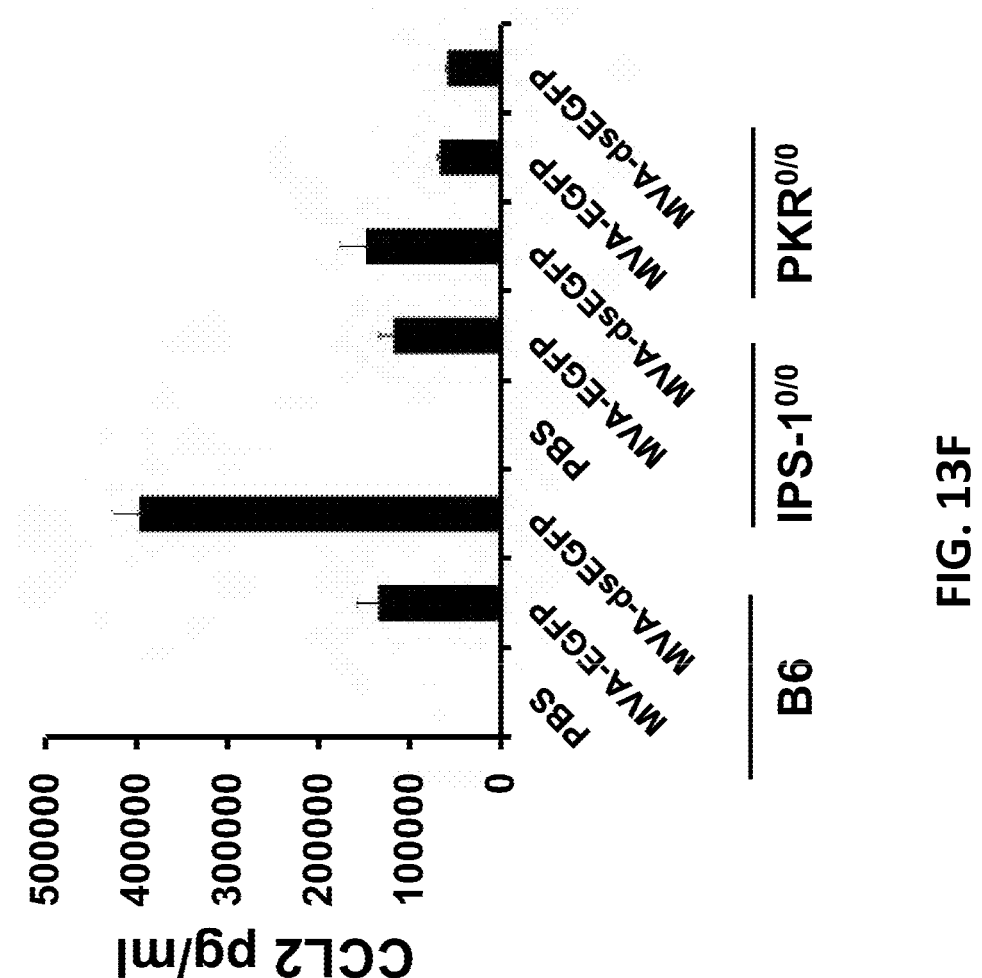
Figure 13G:
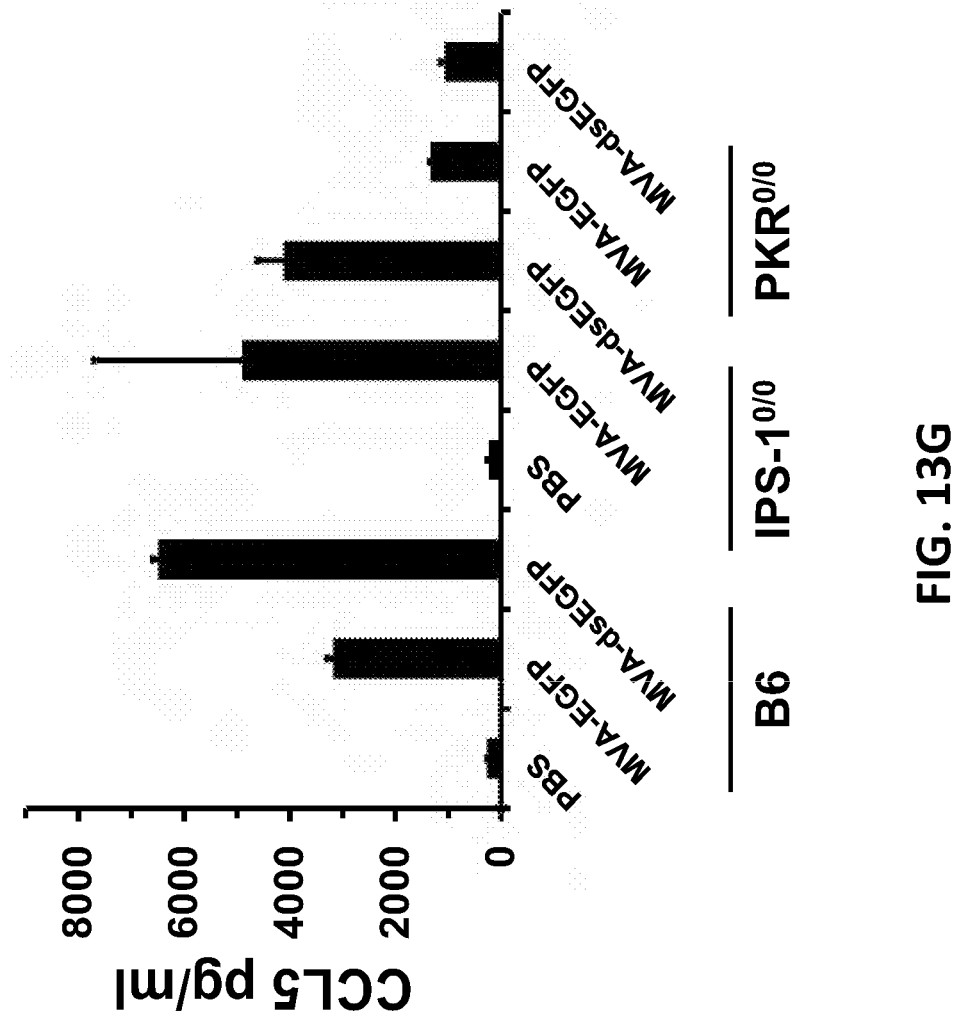

FIGS. 13A, 13B, 13C, 13D, 13E, 13F, and 13G show induction of cytokine expression by mutant MVA-dsEGFP in C57BL/6 wt, IPS-1$^{o/o}$ and PKR$^{o/o}$ mice. Groups of 5 mice of the indicated strains (B6=C57BL/6 wt) aged 8-12 weeks were infected intravenously with the indicated viruses at a dose of $10^8$ TCID$_{50}$ per mouse. Animals were bled 6 hours after infection and serum was analyzed for the concentrations of selected cytokines as indicated using a bead-based flow cytometric assay from Bender Medsystems. FIG. 13A) IFN-α. FIG. 13B) IFN-γ. FIG. 13C) IL-6. FIG. 13D) IL-18. FIG. 13E) CXCL1. FIG. 13F) CCL2. FIG. 13G) CCL5.

Figure 14:
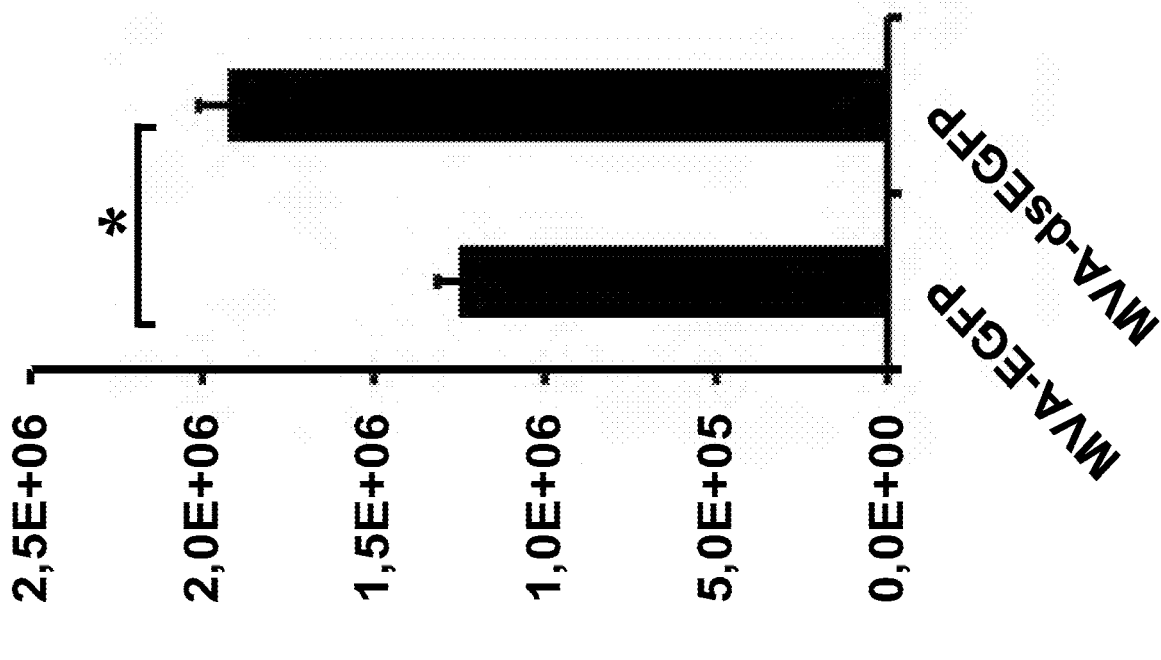

FIG. 14 shows induction of MVA-specific CD8 T cells by MVA-EGFP and mutant MVA-dsEGFP in mice. Groups of 3-5 C57BL/6 mice aged 8 weeks were infected once intravenously with the indicated viruses at a dose of $10^8$ TCID$_{50}$/mouse. Spleens were harvested 7 days p.i. and single cell splenocyte suspensions were used to quantify MVA-specific CD8 T cells by MHC class I dextramer staining using a B820-27 epitope-specific dextramer. Shown are combined results from two independent experiments. Asterisk indicates a p-value of <0.05 in a two-tailed, unpaired student's t test.

Figure 15:
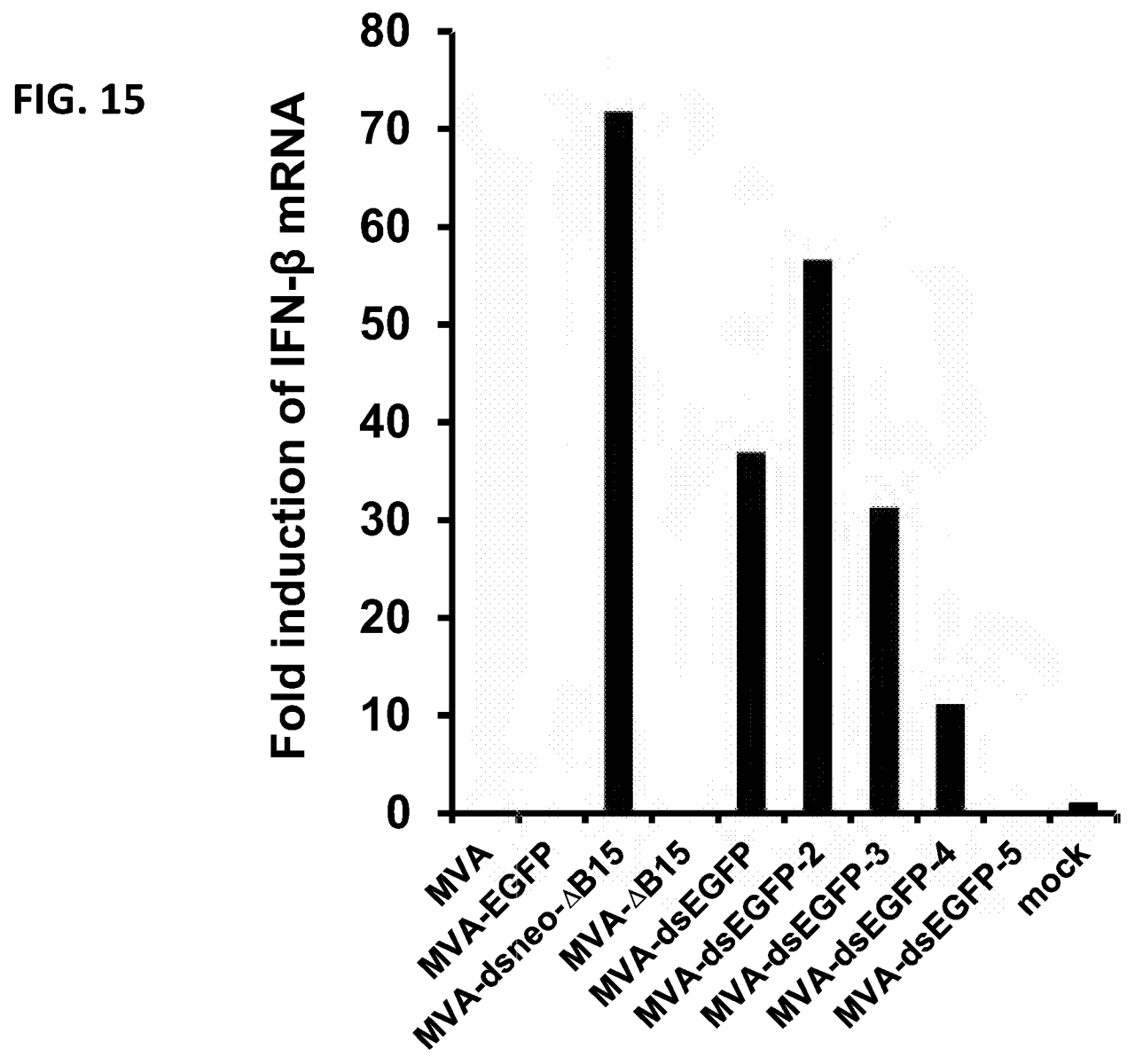

FIG. 15 shows induction of IFN-β mRNA expression in human MRC-5 cells by the MVA-dsEGFP mutants. MRC-5 cells (human diploid lung fibroblasts) in 6-well plates were mock-infected or infected with crude stocks of MVA-EGFP corresponding to MVA wt and the indicated MVA-dsEGFP recombinants with progressively shortened EGFP ORF overlaps. MVA-dsneo-ΔB15 and MVA-ΔB15 were used in addition and fold induction of IFN-β mRNA over mock was determined by RT-qPCR using total RNA isolated from cells at 5 hours post-infection as described in the legend to FIG. 7. IFN-β Ct values were normalized using the Ct values for cellular 18S rRNA, which served as endogenous control. Shown are the levels of IFN-β transcript in infected cells relative to the level of IFN-β mRNA in mock-infected cells expressed as "Fold induction of IFN-β mRNA". 1: MVA; 2: MVA-EGFP; 3: MVA-dsneo-ΔB15; 4: MVA-ΔB15; 5: MVA-dsEGFP; 6: MVA-dsEGFP-2; 7: MVA-dsEGFP-3; 8: MVA-dsEGFP-4; 9: MVA-dsEGFP-5; 10: mock.

Figures 16A, 16B:
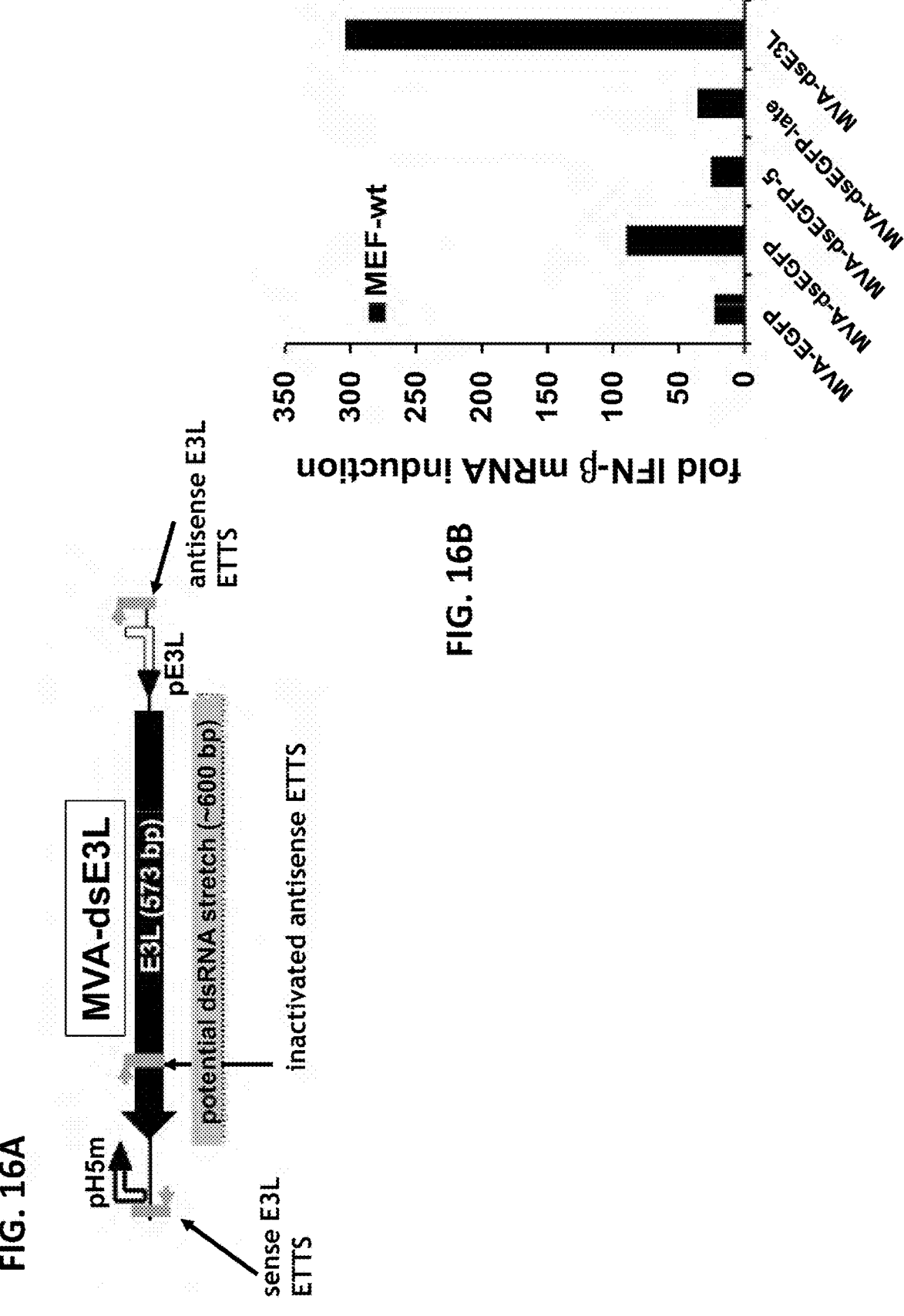

FIGS. 16A and 16B show a schematic representation of MVA-dsE3L and IFN-β gene induction by MVA-dsE3L. FIG. 16A) Schematic drawing of mutant MVA-dsE3L. The direction of transcription of the E3L coding sequence (black arrows) by the native pE3L and the inserted pH5m promoter is indicated. Early transcription termination signals (ETTS's) are indicated by perpendicular grey bars. The grey arrowheads indicate the transcription direction for which the ETTS is potentially active. The antisense ETTS in the E3L ORF was inactivated by site-directed mutagenesis of the wobble position within a codon without changing the E3 amino acid sequence. The potential dsRNA stretch formed by the two complementary E3L transcripts is indicated by a grey bar. FIG. 16B) MEFs in 6-well plates were mock-infected or infected with crude stocks of the indicated viruses at an MOI of 10. MVA-EGFP corresponds to MVA wt. Fold induction of IFN-β mRNA over mock was determined by RT-qPCR using total RNA isolated from cells at 5 h p.i. Ct values for IFN-β mRNA were corrected with Ct values for 18S rRNA, which served as endogenous control. 1: MVA-EGFP; MVA-dsEGFP; 3: MVA-dsEGFP-5; 4: MVA-dsEGFP-late; 5: MVA-dsE3L.

FIGS. 17A, 17B, 17C, 17D, and 17E show that the amino acid sequence of the B19R gene is conserved across a number of poxviruses. FIG. 17A), FIG. 17B), FIG. 17C) and FIG. 17D) show an amino acid sequence alignment of B19R genes and/or homologs thereof encoded by monkeypox virus (SEQ ID NO:1), vaccinia virus-Western Reserve ("Vaccinia-WR")(SEQ ID NO:2), vaccinia virus-Copenhagen (SEQ ID NO:3), chorioallantois vaccinia virus-Ankara ("CVA")(SEQ ID NO:4), ectromelia virus (SEQ ID NO:5), cowpox virus (SEQ ID NO:6), camelpox virus (SEQ ID NO:7), swinepox virus (SEQ ID NO:8), and tanapox virus (SEQ ID NO:9) generated by ClustalO, v. 1.2.0 with the default settings. FIG. 17E) provides a table showing the pairwise amino acid sequence identities for the B19R sequences and/or homologs thereof aligned in FIG. 17A), FIG. 17B), FIG. 17C) and FIG. 17D).

BRIEF DESCRIPTION OF THE SEQUENCES

[Accession No. Q5IXK2: IFN-alpha/beta-receptor-like secreted glycoprotein; Monkeypox virus]:

SEQ ID NO: 1

MMKMKMMVRIYFVSLSLLLFHSYAIDIENEITEFFNKMRDTLPAKDSKWLNPVCMFGGTMNDM

AALGEPFSAKCPPIEDSLLSHRYKDYVVKWERLEKNRRRQVSNKRVKHGDLWIANYTSKFSNR

RYLCTVTTKNGDCVQGVVRSHVWKPSSCIPKTYELGTYDKYGIDLYCGILYAKHYNNITWYKDN

KEINIDDFKYSQAGKELIIHNPELEDSGRYDCYVHYDDVRIKNDIVVSRCKILTVIPSQDHRFKLIL

DPKINVTIGEPANITCSAVSTSLFVDDVLIEWKNPSGWIIGLDFGVYSILTSRGGITEATLYFENVT

EEYIGNTYTCRGHNYYFDKTLTTTVVLE

-continued

[Accession No. P25213: Soluble interferon alpha/beta receptor
B19; Vaccinia virus, strain Western Reserve]:

SEQ ID NO: 2

MTMKMMVHIYFVSLLLLLFHSYAIDIENEITEFFNKMRDTLPAKDSKWLNPACMFGGTMNDIAAL

GEPFSAKCPPIEDSLLSHRYKDYVVKWERLEKNRRRQVSNKRVKHGDLWIANYTSKFSNRRYL

CTVTTKNGDCVQGIVRSHIRKPPSCIPKTYELGTHDKYGIDLYCGILYAKHYNNITWYKDNKEINI

DDIKYSQTGKELIIHNPELEDSGRYDCYVHYDDVRIKNDIVVSRCKILTVIPSQDHRFKLILDPKIN

VTIG EPANITCTAVSTSLLIDDVLIEWENPSGWLIGFDFDVYSVLTSRGGITEATLYFENVTEEYIG

NTYKCRGHNYYFEKTLTTTVVLE

[Accession No. Q5CAD5: IFN-alpha-beta-receptor-like secreted
glycoprotein; Vaccinia virus, strain Copenhagen]:

SEQ ID NO: 3

MTMKMMVHIYFVSLLLLLFHSYAIDIENEITEFFNKMRDTLPAKDSKWLNPACMFGGTMNDIAAL

GEPFSAKCPPIEDSLLSHRYKDYVVKWERLEKNRRRQVSNKRVKHGDLWIANYTSKFSNRRYL

CTVTTKNGDCVQGIVRSHIKKPPSCIPKTYELGTHDKYGIDLYCGILYAKHYNNITWYKDNKEINI

DDIKYSQTGKKLIIHNPELEDSGRYNCYVHYDDVRIKNDIVVSRCKILTVIPSQDHRFKLILDPKIN

VTIGEPANITCTAVSTSLLIDDVLIEWENPSGWLIGFDFDVYSVLTSRGGITEATLYFENVTEEYIG

NTYKCRGHNYYFEKTLTTTVVLE

[Accession No. A9J168: Soluble and cell surface interferon-
alpha/beta receptor; Vaccinia virus, strain Ankara (CVA)]:

SEQ ID NO: 4

MKMTMKMMVHIYFVSLLLLLFHSYAIDIENEITEFFNKMRDTLPAKDSKWLNPACMFGGTMNDI

AALGEPFSAKCPPIEDSLLSHRYKDYVVKWERLEKNRRRQVSNKRVKHGDLWIANYTSKFSNR

RYLCTVTTKNGDCVQGIVRSHIKKPPSCIPKTYELGTHDKYGIDLYCGILYAKHYNNITWYKDNK

EINIDDIKYSQTGKKLIIHNPELEDSGRYNCYVHYDDVKIKNDIVVSRCKILTVIPSQDHRFKLILDP

KINVTIGEPANITCTAVSTSLLIDDVLIEWENPSGWLIG FDFDVYSVLTSRGGITEATLYFENVTEE

YIGNTYKCRGHNYYFEKTLTTTVVLE

[Accession No. Q9JFS5: IFN-alpha/beta binding protein;
Ectromelia virus]:

SEQ ID NO: 5

MMKMTMKMMVRIYFVSLSLSLSLLLLFHSYAIDIENEITEFFNKMRDTLPAKDSKWLNPSCMFGG

TMNDMAALGEPFSAKCPPIEDSLLSHRYNDKDNVVNWEKIGKTRRPLNRRVKNGDLWIANYTS

NDSHRRYLCTVTTKNGDCVQGIVRSHIRKPPSCIPETYELGTHDKYGIDLYCGILYAKHYNNITW

YKNNQELIIDGTKYSQSGQNLIIHNPELEDSGRYDCYVHYDDVRIKNDIVVSRCKILTVIPSQDHR

FKLILDPKINVTIGEPANITCTAVSTSLLVDDVLIDWENPSGVVIIGLDFGVYSILTSSGGITEATL

YFENVTEEYIGNTYTCRGHNYYFDKTLTTTVVLE

[Accession No. Q5CAC3: Soluble interferon-alpha/beta receptor;
Cowpox virus]:

SEQ ID NO: 6

MKMTMKMMVHIYFVSLSLSLSLLLLFHSYAIDIENEITEFFNKMKDTLPAKDSKWLNPACMFGGT

MNDMAAIGEPFSAKCPPIEDSLLSHRYKDKDNVVNWEKIGKTRRPLNRRVKNGDLWIANYTSN

DSRRRYLCTVITKNGDCIQGIVRSHVRKPSSCIPEIYELGTHDKYGIDLYCGIIYAKHYNNITVVYK

DNKEINIDDIKYSQTGKELIIHNPALEDSGRYDCYVHYDDVRIKNDIVVSRCKILTVIPSQDHRFKLI

LDPKINVTIGEPANITCTAVSTSLLVDDVLIEWENPSGWLIGFDFDVYSVLTSRGGITEATLYFEN

VTEEYIGNTYKCRGHNYYFEKTLTTTVVLE

-continued

[Accession No. Q5CA87: Soluble interferon-alpha/beta receptor;
Camelpox virus]:

SEQ ID NO: 7

MKMTMKMMVHIYFVSLSLSLLLFHSYAIDIENEITDFFNKMKDILPTKDSKWLNPACMFGGTTND

MAAIGEPFSAKCPPIEDSLLSHRYKNKDNVVNWEKIGKTKRPLNRRVKNGDLWIANYTSNDSR

RRYLCTAITKNGDCIQGIIRSHVRKPSSCIPEIYELGTHDKYGIDLYCGIIYAKHYNNITWYKDNKEI

NIDDIKYSQTGKELIIHNPALEDSGRYDCYVHYDDVRIKNDIVVSRCKILTVTPSQDHRFKLILDPK

INVTIGEPANITCTAVSTSLLVDDVLIEWENPSGWLIGFDFDVYSVLTSRGGITEATLYFENVTEE

YIGNTYKCRGHNYYFEKTLTTTVVLE

[Accession No. Q8V3G4: IFN-alpha/beta-like binding protein;
Swinepox virus, strain Swine/Nebraska/17077-99/1999]:

SEQ ID NO: 8

MISIKKYNILLFIISFIYCSADNDIDSLYEGYKEFLDPKLKQFLNDNCTYRGYRDFFLYNEEPANIKC

PLLNDILLRQKYHNYTILWKKLGERSSRLLNTHGSIFLDFFPYKSELRGSVYECMIILNNTCDQFIL

KLNDIRSNPVCYHNDYKVHTNIEIFCNVINLQYDYITWYKNNSEIIIDGYKYSNQSRRLLVYNTTY

NDSGIYYCNAYTTHGKNTYISRRCSSVSIHSHSYYDFYIEHINNITYIDPDSENTQIYCKAISYSNS

SYILIYWEDEYGGYIYDNGIYQYDNITLIGNEKVYMSILVLEKSAYYRYVNNTFTCLATSVYVEKK

TTTTLVIKKT

[Accession No. A7XCS4: Type-I IFN receptor; Tanapox virus):

SEQ ID NO: 9

MKITYIILLICKEIICDNSGDDMYDYIANGNIDYLKTIDNDIINLVNKNCSFREIKTTLAKENEVLML

KCPQLDNYILPWKYMNRSEYTVTVVKNISNSTEYNNTRIENNMLMFFPFYNLQAGSKYLCTVSTN

KSCDQSVVIVKKSFYSNNCMLSEAKENDNFEIYCGILHAKYNTIKWFKEEKEITNNYKYYTKLGG

YVKGINNVTYSDSGKYVCEGYYIDVLKNITYTAKRCVNLTVIPNTYYDFFIVDIPNVTYAKNNKKL

EVNCTSFVDINSYDYILTSWLYNGLYLPLGVRIYQLYSTDIFFENFIYRTSTLVFENVDISDDNKTF

ECEALSVTLKKIKYTTIKVEK

DESCRIPTION OF CERTAIN EMBODIMENTS

Reference will now be made in detail to exemplary embodiments, examples of which are illustrated in the accompanying drawings.

Definitions

Unless otherwise noted, technical terms herein are used according to conventional usage by one of ordinary skill in the art of molecular biology. For common terms in molecular biology, conventional usage may be found in standard textbooks such as, for example, Genes V by Benjamin Lewin, published by Oxford University Press, 1994 (ISBN 0-19-854287-9); Kendrew et al. (eds.); *The Encyclopedia of Molecular Biology*, published by Blackwell Science Ltd., 1994 (ISBN 0-632-02182-9); and *Molecular Biology and Biotechnology: a Comprehensive Desk Reference* edited by Robert A. Meyers, published by VCH Publishers, Inc., 1995 (ISBN 1-56081-569-8).

As used herein, the singular forms "a", "an", and "the" include plural references unless the context clearly indicates otherwise. Thus, for example, reference to "an epitope" includes reference to one or more epitopes and reference to "the method" includes reference to equivalent steps and methods known to those of ordinary skill in the art that could be modified or substituted for the methods provided herein.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention provided herein. Such equivalents are encompassed by the present invention.

Throughout this specification and the claims which follow, unless the context requires otherwise, the word "comprise", and variations such as "comprises" and "comprising" mean "includes", and therefore include a stated integer or step or group of integers or steps and do exclude any other integer or step or group of integers or steps. When used herein the term "comprising" can be substituted with the term "containing", "including" or "having". Any of the aforementioned terms (comprising, containing, including, having), whenever used herein in the context of an aspect or embodiment of the present invention can be substituted with the term "consisting of".

When used herein, the term "consisting of" excludes any element, step, or ingredient not specified in the claim. When used herein, "consisting essentially of" excludes any materials or steps "which would affect the basic and novel characteristics" of the product or method defined in the rest of the claim. *Water Techs. Corp. v. Calco Ltd.,* 7 U.S.P.Q.2d 1097, 1102 (Fed. Cir. 1988).

As used herein, the conjunctive "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore to satisfy the requirement of the term "and/or" as used herein. Concurrent applicability of more than one of the options is also understood to fall within the meaning, and therefore satisfy the requirement of the term "and/or."

All publications, patent applications, patents, and other references mentioned herein are incorporated by reference in their entirety. In case of conflict, the present specification, including all definitions, will control.

Adjuvant. A vehicle used to enhance antigenicity. Adjuvants can include: (1) suspensions of minerals (alum, aluminum hydroxide, or phosphate) on which antigen is adsorbed; (2) water-in-oil emulsions in which an antigen solution is emulsified in mineral oil (Freund's incomplete adjuvant), sometimes with the inclusion of killed mycobacteria (Freund's complete adjuvant) to further enhance antigenicity by inhibiting degradation of antigen and/or causing an influx of macrophages and/or activating immune cells; (3) immunostimulatory oligonucleotides such as, for example, those including a CpG motif can also be used as adjuvants (for example see U.S. Pat. Nos. 6,194,388; and 6,207,646); and (4) purified or recombinant proteins such as costimulatory molecules. Exemplary adjuvants include, but are not limited to, B7-1, ICAM-1, LFA-3, and GM-CSF.

Antigen; antigenic determinant; epitope. A compound, composition, or substance that can stimulate the production of antibodies or a CD4+ or CD8+ T-cell response in an animal, including compositions that are injected or absorbed into an animal. An antigen reacts with the immune system to produce an antigen-specific humoral or cellular immune response. The term "antigen" includes all related epitopes of a particular compound, composition or substance. The term "epitope" or "antigenic determinant" refers to a site on an antigen to which B- and/or T-cells respond, either alone or in conjunction with another protein such as, for example, a major histocompatibility complex ("MHC") protein or a T-cell receptor. T cell epitopes are formed from contiguous stretches of 8 to ~20 amino acids. B cell epitopes can be formed both from contiguous amino acids or noncontiguous amino acids juxtaposed by secondary and/or tertiary folding of a protein. B cell epitopes formed from contiguous amino acids are typically retained on exposure to denaturing solvents, while epitopes formed by tertiary folding are typically lost on treatment with denaturing solvents. A B cell epitope typically includes at least 5, 6, 7, 8, 9, 10 or more amino acids—but generally less than 20 amino acids—in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996).

An antigen can be a tissue-specific (or tissue-associated) antigen or a disease-specific (or disease-associated) antigen. Those terms are not mutually exclusive, because a tissue-specific antigen can also be a disease-specific antigen. A tissue-specific antigen is expressed in a limited number of tissues. Tissue-specific antigens include, for example, prostate-specific antigen ("PSA"). A disease-specific antigen is expressed coincidentally with a disease process, where antigen expression correlates with or is predictive of development of a particular disease. Disease-specific antigens include, for example, HER-2, which is associated with certain types of breast cancer, or PSA, which is associated with prostate cancer. A disease-specific antigen can be an antigen recognized by T-cells or B-cells. Tissue- and/or disease-specific antigens can include, but are not limited to, bacterial antigens, fungal antigens, parasite antigens, or tumor-associated antigens, or viral antigens.

Bacterial antigens. Antigens derived from one or more bacterial species or strains thereof, such as, for example, *Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diptheriae, Enterococcus faecalis, Enterococcus faecium, Escherichia coli*, enterotoxigenic *Escherichia coli*, enteropathogenic *Escherichia coli, Escherichia coli*)157:H7, *Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae,* and *Yersinia pestis.*

Fungal antigens. Antigens derived from one or more fungal species or strains thereof, such as, for example, *Aspergillus clavatus, Aspergillus flavus, Aspergillus fumigatus, Aspergillus nidulans, Aspergillus niger, Aspergillus terreus, Blastomyces dermatitidis, Candida albicans, Candida dubliniensis, Candida glabrata, Candida parapsilosis, Candida rugosa, Candida tropicalis, Cryptococcus albidus, Cryptococcus gattii, Cryptococcus laurentii, Cryptococcus neoformans, Histoplasma capsulatum, Microsporum canis, Pneumocystis carinii, Pneumocystis jirovecii, Sporothrix schenckii, Stachbotrys chartarum, Tinea barbae, Tinea captitis, Tinea corporis, Tinea cruris, Tinea faciei, Tinea incognito, Tinea nigra, Tinea versicolor, Trichophyton rubrum* and *Trichophyton tonsurans.*

Parasite antigens. Antigens derived from one or more parasite species or strains thereof, such as, for example, *Anisakis* spp. *Babesia* spp., *Baylisascaris procyonis, Cryptosporidium* spp., *Cyclospora cayetanensis, Diphyllobothrium* spp., *Dracunculus medinensis, Entamoeba histolytica, Giardia duodenalis, Giardia intestinalis, Giardia lamblia, Leishmania* sp., *Plasmodium falciparum, Schistosoma mansoni, Schistosoma haematobium, Schistosoma japonicum, Taenia* spp., *Toxoplasma gondii, Trichinella spiralis,* and *Trypanosoma cruzi.*

Tumor-associated antigens. Antigens over-expressed or expressed predominantly on particular tumor types, such as, for example, 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/F$_c$εRII, CD33, CD35/complement receptor 1 ("CR1"), CD44/PGP-1, CD45/leucocyte common antigen ("LCA"), CD46/membrane cofactor protein ("MCP"), CD52/CAM PATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin, gastrin-releasing hormone, ganglioside 2 ("GD2")/ganglioside 3 ("GD3")/ganglioside-monosialic acid-2 ("GM2"), gonadotropin releasing hormone ("GnRH"), UDP-GlcNAc: $R_1Man(\alpha1-6)R_2$ [GlcNAc to $Man(\alpha1-6)$] $\beta1,6$-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, Her2/neu, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding gene 1 ("MAGE-1"), melanoma antigen-encoding gene 2 ("MAGE-2"), melanoma antigen-encoding gene 3 ("MAGE-3"), melanoma antigen-encoding gene 4 ("MAGE-4"), mammaglobin, MAP17, Melan-A/melanoma antigen recognized by T-cells-1 ("MART-1"), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor ("PDGF"), μPA, PRAME, probasin, progenipoietin, prostate-specific antigen ("PSA"), prostate-specific membrane antigen ("PSMA"), RAGE-1, Rb, RCAS1, SART-1, SSX-family, STAT3, STn, TAG-72, transforming growth factor-alpha ("TGF-α"), transforming growth factor-beta ("TGF-β"), Thymosin-beta-15, tumor necrosis factor-alpha ("TNF-α"), TP1, TRP-2, tyrosinase, vascular endothelial growth factor ("VEGF"), ZAG, p16INK4, and glutathione-S-transferase ("GST").

Viral antigens. Antigens derived from one or more virus types or isolates thereof, such as, for example, adenovirus, Coxsackievirus, Crimean-Congo hemorrhagic fever virus, cytomegalovirus ("CMV"), dengue virus, Ebola virus, Epstein-Barr virus ("EBV"), Guanarito virus, herpes simplex virus-type 1 ("HSV-1"), herpes simplex virus-type 2 ("HSV-2"), human herpesvirus-type 8 ("HHV-8"), hepatitis A virus ("HAV"), hepatitis B virus ("HBV"), hepatitis C virus ("HCV"), hepatitis D virus ("HDV"), hepatitis E virus ("HEV"), human immunodeficiency virus ("HIV"), influenza virus, Junin virus, Lassa virus, Machupo virus, Marburg virus, measles virus, human metapneumovirus, mumps virus, Norwalk virus, human papillomavirus ("HPV"), parainfluenza virus, parvovirus, poliovirus, rabies virus, respiratory syncytial virus ("RSV"), rhinovirus, rotavirus, rubella virus, Sabia virus, severe acute respiratory syndrome virus ("SARS"), Middle East Respiratory Syndrome Coronavirus ("MERS-CoV"), varicella zoster virus, variola virus, West Nile virus, and yellow fever virus.

cDNA (complementary DNA). A piece of DNA lacking internal non-coding segments (introns) and regulatory sequences that determine the timing and location of transcription initiation and termination. cDNA can be synthesized in the laboratory by reverse transcription of messenger RNA ("mRNA") extracted from cells.

Conservative variant. A "conservative" variant is a variant protein or polypeptide having one or more amino acid substitutions that do not substantially affect or decrease an activity or antigenicity of the protein or an antigenic epitope thereof. Generally conservative substitutions are those in which a particular amino acid is substituted with another amino acid having the same or similar chemical characteristics. For example, replacing a basic amino acid such as lysine with another basic amino acid such as arginine or glutamine is a conservative substitution. The term conservative variant also includes the use of a substituted amino acid in place of an unsubstituted parent amino acid, provided that antibodies raised to the substituted polypeptide also immunoreact with the unsubstituted polypeptide, and/or that the substituted polypeptide retains the function of the unsubstituted polypeptide. Non-conservative substitutions are those that replace a particular amino acid with one having different chemical characteristics, and typically reduce an activity or antigenicity of the protein or an antigenic epitope thereof.

Specific, non-limiting examples of conservative substitutions include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

CD4. Cluster of differentiation factor 4, a T-cell surface protein that mediates interaction with the MHC Class II molecule. Cells that express CD4, referred to as "CD4+" cells, are often helper T (e.g., "$T_H$", "$T_H1$" or "$T_H2$") cells.

CD8. Cluster of differentiation factor 8, a T-cell surface protein that mediates interaction with the MHC Class I molecule. Cells that express CD8, referred to as "CD8+" cells, are often cytotoxic T ("CTL") cells.

Costimulatory molecule. T-cell activation typically requires binding of the T-cell receptor ("TCR") with a peptide-MHC complex as well as a second signal delivered via the interaction of a costimulatory molecule with its ligand. Costimulatory molecules are molecules that, when bound to their ligand, deliver the second signal required for T-cell activation. The most well-known costimulatory molecule on the T-cell is CD28, which binds to either B7-1 or B7-2. Other costimulatory molecules that can also provide the second signal necessary for activation of T-cells include intracellular adhesion molecule-1 ("ICAM-1"), intracellular adhesion molecule-2 ("ICAM-2"), leukocyte function associated antigen-1 ("LFA-1"), leukocyte function associated antigen-2 ("LFA-2"), and leukocyte function associated antigen-3 ("LFA-3"). The combination of B7-1, ICAM-1, and LFA-3 is referred to as "TRICOM", for "TRIad of COstimulatory Molecules".

Dendritic cell (DC). Dendritic cells are the main antigen presenting cells ("APCs") involved in primary immune responses. Dendritic cells include plasmacytoid dendritic cells and myeloid dendritic cells. Their major function is to obtain antigen in tissues, migrate to lymphoid organs and present the antigen in order to activate T-cells. Immature dendritic cells originate in the bone marrow and reside in the periphery as immature cells.

Double-stranded RNA (dsRNA). Recombinant poxvirus virus comprising heterologous or native nucleic acids expressing an increased number or amount of dsRNA (e.g.

expressing excess dsRNA) according to any embodiment of the present invention triggers the release of cytokines, chemokines, effector molecules and/or increased expression of costimulatory molecules or activates one or more pattern recognition receptor(s) (PRRs) and/or activates cells (e.g dendritic cells, macrophages, B cells or other types of immune cells) and thus preferably triggers or induces an enhanced innate immune response. Excess dsRNA can be determined by any method suitable, preferably by using a method to determine enhanced innate immune response or any method as described in the examples preferably the method according to Example 16. Preferably, excess dsRNA can be defined as the amount of dsRNA early in infection that generates an enhanced innate immune response when using the recombinant poxvirus vector of the present invention. More preferably, excess dsRNA can be defined as the amount of dsRNA transcribed during the early phase of virus infection with the recombinant poxvirus comprising heterologous nucleic acids expressing or generating dsRNA compared to the control. Excess dsRNA can be generated by driving transcription of sense and antisense RNA with identical or overlapping sequence stretches preferably of at least 100 bp in length by using poxviral promoters with early activity (e.g, immediate early, early, or early/late poxviral promoters). Another method of determining excess dsRNA is to determine enhanced activation of one or more PRR(s) e.g. PKR as determined by increased phosphorylation of a PKR substrate (e.g. elF2$\alpha$ at position Serine-51) as shown in Example 7. Preferably, increased phosphorylation of a PKR substrate (e.g. elF2$\alpha$ at position Serine-51) increases by at least 2-fold, at least 4-fold, at least 6-fold, at least 8-fold, at least 10-fold, at least 15-fold, at least 20-fold, at least 30-fold, at least 40-fold, at least 50-fold, at least 100-fold or more as compared to the control.

Early in infection. Gene expression of poxviruses is regulated in a cascade fashion. Early transcription of viral genes is driven by the viral transcriptional machinery carried with the viral particle into the newly infected cell and is under control of early viral promoters that are recognized by the early viral transcription complex. It is well known that once the virion and host membranes have fused and the virus core has been released into the cytoplasm, the endogenous RNA polymerase and encapsidated transcription factors that comprise the viral gene expression, begin the first cascade of early viral gene expression which synthesizes viral mRNA under the control of early promoters. Usually early in infection e.g. early phase lasts about 1 to 2 hours prior to genome replication. Preferably, early in infection is the time span between binding of the virus particle (e.g. the recombinant poxvirus) to the host cell and onset of the viral genome replication (e.g. recombinant poxvirus genome replication). Among early proteins are transcription factors for the replication of the viral dsDNA genome and the next transcription phase termed intermediate that can only start after onset of viral genome replication. Preferably, early in infection is within 30 min, one hour or two hours of infection or after inoculation, preferably after the virus core has been released into the cytoplasm of a cell.

Expression Control Sequences. Nucleic acid sequences that regulate the expression of a heterologous nucleic acid sequence to which they are operatively linked. Expression control sequences are operatively linked to a nucleic acid sequence when the expression control sequences control and regulate the transcription and/or translation of the nucleic acid sequence. Thus, the term "expression control sequences" encompasses promoters, enhancers, transcription terminators, start codons, splicing signals for introns, and stop codons. The term "control sequences" includes, at a minimum, components the presence of which can influence transcription and/or translation of the heterologous nucleic acid sequence and can also include additional components whose presence is advantageous such as, for example, leader sequences and fusion partner sequences.

The term "expression control sequences" encompasses promoter sequences. A promoter is a minimal sequence sufficient to direct transcription of a homologous or heterologous gene. Also included are those promoter elements sufficient to render promoter-dependent gene expression cell-type specific, tissue-specific, or inducible by external signals or agents; such elements may be located in the 5' or 3' regions of the gene. The term "promoter" encompasses both constitutive and inducible promoters. See, e.g., Bitter et al., *Methods in Enzymology* 153:516-544 (1987). Exemplary promoter sequences include, but are not limited to, the retrovirus long terminal repeat ("LTR"), the adenovirus major late promoter, the vaccinia virus 7.5K promoter ("Pr7.5"), the vaccinia virus synthetic early/late promoter ("sE/L"), the PrSynllm promoter, the PrLE1 promoter, the PrH5m promoter, the PrS promoter, a hybrid early/late promoter, or a cowpox virus ATI promoter. Other suitable promoters include, but are not limited to, the SV40 early promoter, the adenovirus major late promoter, the human CMV immediate early I promoter, and various poxvirus promoters including, but not limited to the following vaccinia virus or MVA-derived promoters: the 30K promoter, the 13 promoter, the sE/L promoter, the Pr7.5K promoter, the 40K promoter, the C1 promoter, the PrSynllm promoter, the PrLE1 promoter, the PrH5m promoter, the PrS promoter, a hybrid early/late promoter PrHyb, the PrS5E promoter, the PrA5E promoter, the Pr13.5-long promoter, and the Pr4LS5E promoter; a cowpox virus ATI promoter, or the following fowlpox-derived promoters: the Pr7.5K promoter, the 13 promoter, the 30K promoter, or the 40K promoter.

Heterologous. Originating from separate genetic sources or species. A polypeptide that is heterologous to modified vaccinia virus Ankara ("MVA") originated from a nucleic acid not included within the MVA genome such as, for example, a bacterial antigen, a fungal antigen, a parasite antigen, a tumor-associated antigen, or a viral antigen. The term is interpreted broadly to encompass any non-native nucleic acid encoding an RNA or protein not normally encoded by the MVA genome or any non-native protein encoded by such a non-native nucleic acid.

Homologue; variant. The term "homologue" or "variant" when referring to a gene or protein sequence encompasses the native amino acid sequence of the gene or protein in question, protein fragments still able to elicit an immune response in a host, as well as homologues or variants of proteins and protein fragments including, for example, glycosylated proteins or polypeptides. Thus, proteins and polypeptides are not limited to particular native amino acid sequences but encompass sequences identical to the native sequence as well as modifications to the native sequence, such as deletions, additions, insertions and substitutions. Preferably, such homologues or variants have at least about 80%, 81%, 82%, 83%, 84%, 85%, 86%, 87%, 88%, or 89%, at least about 90%, 91%, 92%, 93%, or 94%, at least about 95%, 96%, 97%, 98% or 99%, or about 100% amino acid sequence identity with the referenced protein or polypeptide. The term homologue or variant also encompasses truncated, deleted or otherwise modified nucleotide or protein sequences.

The term homologue or variant also encompasses degenerate variants of native sequences. A degenerate variant is a polynucleotide encoding a protein or fragment thereof that includes a sequence containing codons that differ from the native or wild-type gene sequence but still specifies the same amino acid sequence. The genetic code specifies 20 natural amino acids, most of which are encoded by more than one codon. Thus, it is a redundant or degenerate code. All degenerate nucleotide sequences are encompassed in this disclosure provided the amino acid sequence of the protein encoded by the degenerate polynucleotide remains unchanged.

Techniques for determining sequence identity between amino acid sequences are known in the art. Two or more sequences can be compared by determining their "percent identity." The percent identity of two sequences is the number of exact matches between two aligned sequences divided by the length of the shorter sequence and multiplied by 100.

"Percent (%) amino acid sequence identity" with respect to proteins, polypeptides, antigenic protein fragments, antigens and epitopes described herein is defined as the percentage of amino acid residues in a candidate sequence that are identical with the amino acid residues in the reference sequence (i.e., the protein, polypeptide, antigenic protein fragment, antigen or epitope from which it is derived), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the level of ordinary skill in the art, for example, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

Host cells. Cells in which a vector can be propagated and its DNA expressed. The cells may be prokaryotic (e.g., bacterial) or eukaryotic (e.g., mammalian or human). The term also encompasses progeny of the original host cell, even though all progeny may not be identical to the parental cell since there may be mutations that occur during replication.

Immune response. An adaptive response of an immune system cell, such as a B-cell, T-cell, or monocyte, to a stimulus. An adaptive response is a response to a particular antigen, and is thus described as "antigen-specific". An adaptive immune response can include the production of antibodies to a particular antigen by a B-cell, T-cell help by a CD4$^+$ helper T-cell, expanding a population of antigen-specific CD8$^+$ T-cells (cytotoxic T lymphocytes, "CTLs"), cytotoxic activity of CD8$^+$ T-cells directed against cells expressing a particular antigen, or yet another type of antigen-specific immune response.

Immunogenic composition. As used herein, the term "immunogenic composition" refers to a composition comprising a recombinant poxvirus comprising heterologous nucleic acids expressing early double-stranded RNA (dsRNA). The term also encompasses recombinant poxviruses comprising heterologous nucleic acids expressing early dsRNA and nucleic acid sequences encoding a heterologous disease-associated antigen. In certain embodiments, the heterologous disease-associated antigen is an infectious disease-associated antigen or a tumor-associated antigen. In certain embodiments, the disease-associated antigen is an infectious disease antigen. In certain embodiments, the infectious disease antigen is a viral antigen, a bacterial antigen, a fungal antigen, or a parasite antigen. The recombinant poxvirus may optionally include additional nucleic acids encoding, for example, one or more costimulatory molecules as described elsewhere herein. Such compositions may include the recombinant poxvirus, optionally formulated with one or more pharmaceutically acceptable carriers.

"In need thereof". When used with respect to methods of enhancing an immune response and use of the recombinant poxviruses, immunogenic compositions, and pharmaceutical compositions provided herein, a subject "in need thereof" may be an individual who has been diagnosed with or previously treated for a medical condition resulting from, for example, a viral, bacterial, fungal, or parasite infection, or for a neoplastic condition (i.e., cancer). With respect to prevention, the subject in need thereof may also be a subject at risk for developing a medical condition (e.g., having a family history of the condition, life-style factors indicative of risk for the condition, etc.).

Lymphocytes. A type of white blood cell that is involved in the immune defenses of the body. There are two main types of lymphocytes: B-cells and T-cells.

Major Histocompatibility Complex ("MHC"). A generic designation meant to encompass the histocompatability antigen systems described in different species, including the human leukocyte antigens ("HLA").

Mammal. This term includes both human and non-human mammals. Similarly, the term "subject" includes both human and veterinary subjects.

Open reading frame ("ORF"). A series of nucleotide codons following a eukaryotic start codon (ATG) specifying a series of amino acids without any internal termination codons that is capable of being translated to produce a polypeptide, or a series of nucleotides without any internal termination codons that is capable of being transcribed to produce an RNA molecule, such as, for example, ribosomal RNA (rRNA) or transfer RNA (tRNA).

Operably linked. A first nucleic acid sequence is operably linked to a second nucleic acid sequence when the first nucleic acid sequence is placed in a functional relationship with the second nucleic acid sequence. For example, a promoter is operably linked to a coding sequence if the promoter is placed in a position where it can direct transcription of the coding sequence. Generally, operably linked DNA sequences are contiguous and, where necessary to join two protein-coding regions, in the same reading frame.

Pharmaceutically acceptable carriers. The terms "pharmaceutically acceptable carrier" or "pharmaceutically suitable carrier" and the like as used herein refer to pharmaceutical excipients, for example, pharmaceutically, physiologically, acceptable organic or inorganic carrier substances suitable for enteral or parenteral application which do not deleteriously react with the extract. *Remington's Pharmaceutical Sciences*, by E. W. Martin, Mack Publishing Co., Easton, PA, 15th Edition (1975), describes compositions and formulations using conventional pharmaceutically acceptable carriers suitable for administration of the vectors and compositions disclosed herein. Generally the nature of the carrier used depends on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like, as a vehicle. For solid compositions (such as powders, pills, tablets, or capsules), conventional non-toxic solid carriers include, for example, pharmaceutical grades of mannitol, lactose, starch, or magnesium stearate. Pharmaceutical compositions can also contain minor amounts of non-toxic auxiliary substances such as wetting or emulsifying agents, preservatives, pH-buffering agents and the like such as, for example, sodium acetate or sorbitan monolaurate.

"Pharmaceutically effective amount," "therapeutically effective amount," "effective amount". As used herein, those terms (and cognates thereof) refer to an amount that results in a desired pharmacological and/or physiological effect for a specified condition (e.g., a medical condition, disease, infection, or disorder) or one or more of its symptoms and/or to completely or partially prevent the occurrence of the condition or symptom thereof and/or may be therapeutic in terms of a partial or complete cure for the condition and/or adverse effect attributable to the condition. The "pharmaceutically effective amount" or "therapeutically effective amount" will vary depending on the composition being administered, the condition being treated/prevented, the severity of the condition being treated or prevented, the age and relative health of the individual, the route and form of administration, the judgment of the attending medical or veterinary practitioner, and other factors appreciated by the skilled artisan in view of the teachings provided herein.

Polynucleotide; nucleic acid. The term polynucleotide refers to a nucleic acid polymer at least 300 bases long composed of ribonucleotides (i.e., RNA) or deoxyribonucleotides (i.e., DNA or cDNA) and capable or not capable of encoding a polypeptide or protein. The term includes single- and double-stranded forms of DNA.

Polypeptide or Protein. The term polypeptide or protein refers to a polymer at least 100 amino acids long, generally greater than 30 amino acids in length.

Poxvirus. The term "poxvirus" refers to either of the two subfamilies of the family Poxviridae: Chordopoxvirinae and Entomopoxvirinae. Members of the Chordopoxvirinae subfamily infect vertebrates. Members of the Entomopoxvirinae subfamily infect insects (i.e., invertebrates). The term "poxvirus" also refers to members of any of the genera of Chordopoxvirinae (e.g., avipox viruses, capripox viruses, leporipox viruses, molluscipox viruses, orthopox viruses, parapox viruses, suipoxviruses, and yatapox viruses), including those four that may infect humans (orthopox viruses, parapox viruses, yatapox viruses, and molluscipox viruses), whether productively or not, but preferably the orthopox and/or avipox viruses. The term "poxvirus" also refers to members of any of the genera of Entomopoxvirinae (e.g., alpha-entomopox viruses, beta-entomopox viruses, and gamma-entomopox viruses).

Avipox viruses include canarypox virus, fowlpox virus, mynahpox virus, pigeonpox virus, and quailpox virus. Capripox viruses include sheeppox viruses, goatpox viruses, and lumpy skin disease virus. Leporipox viruses include myxoma virus, Shope fibroma virus (also known as rabbit fibroma virus), hare fibroma virus, and squirrel fibroma virus. Molluscipox viruses include Molluscum contagiosum virus. Orthopox viruses include buffalopox virus, camelpox virus, cowpox virus, ectromelia virus, monkeypox virus, raccoonpox virus, smallpox virus (also known as variola virus), and vaccinia virus. The term "vaccinia virus" refers to both the wild-type vaccinia virus and any of the various attenuated strains or isolates subsequently isolated including, for example, vaccinia virus-Western Reserve, vaccinia virus-Copenhagen, Dryvax (also known as vaccinia virus-Wyeth), ACAM2000, chorioallantois vaccinia virus Ankara (CVA), modified vaccinia virus Ankara (MVA), and modified vaccinia virus Ankara-Bavarian Nordic ("MVA-BN"). Parapox viruses include bovine papular stomatitis virus, ORF virus, parapoxvirus of New Zealand red deer, and pseudocowpox virus. Suipox viruses include swinepox virus. Yatapox viruses include tanapox virus and yaba monkey tumor virus.

The term "Modified Vaccinia Virus Ankara" or "MVA" refers to a virus generated by more than 570 serial passages of the dermal vaccinia strain Ankara [Chorioallantois vaccinia virus Ankara virus (CVA); for review see Mayr et al. (1975), *Infection* 3:6-14] on chicken embryo fibroblasts. CVA was maintained in the Vaccination Institute, Ankara, Turkey for many years and used as the basis for vaccination of humans. However, due to the often severe post-vaccination complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells [Mayr et al. (1975)]. It was shown in a variety of animal models that the resulting MVA was avirulent [Mayr, A. & Danner, K. (1978), *Dev. Biol. Stand.* 41:225-234]. As part of the early development of MVA as a pre-smallpox vaccine, there were clinical trials using MVA-517 in combination with Lister Elstree [Stickl (1974), Prev. Med. 3:97-101; Stickl and Hochstein-Mintzel (1971), Munich Med. Wochenschr. 113:1149-1153] in subjects at risk for adverse reactions from vaccinia. In 1976, MVA derived from MVA-571 seed stock (corresponding to the $571^{st}$ passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. (1978), *Zentralbl. Bacteriol.* (B) 167: 375-390). MVA-572 was deposited at the European Collection of Animal Cell Cultures as ECACC V94012707.

As a result of the passaging used to attenuate MVA, there are a number of different strains or isolates, depending on the passage number in CEF cells. For example, MVA-572 was used in Germany during the smallpox eradication program, and MVA-575 was extensively used as a veterinary vaccine. MVA-575 was deposited on Dec. 7, 2000, at the European Collection of Animal Cell Cultures (ECACC) with the deposition number V00120707. The attenuated CVA-virus MVA (Modified Vaccinia Virus Ankara) was obtained by serial propagation (more than 570 passages) of the CVA on primary chicken embryo fibroblasts.

Even though Mayr and colleagues demonstrated during the 1970s that MVA is highly attenuated and avirulent in humans and mammals, certain investigators have reported that MVA is not fully attenuated in mammalian and human cell lines since residual replication might occur in these cells [Blanchard et al. (1998), *J. Gen. Virol.* 79:1159-1167; Carroll & Moss (1997), *Virology* 238:198-211; U.S. Pat. No. 5,185,146; Ambrosini et al. (1999), *J. Neurosci. Res.* 55: 569]. It is assumed that the results reported in these publications have been obtained with various known strains of MVA, since the viruses used essentially differ in their properties, particularly in their growth behaviour in various cell lines. Such residual replication is undesirable for various reasons, including safety concerns in connection with use in humans.

Strains of MVA having enhanced safety profiles for the development of safer products, such as vaccines or pharmaceuticals, have been developed by Bavarian Nordic: MVA was further passaged by Bavarian Nordic and is designated MVA-BN. MVA as well as MVA-BN lacks approximately 13% (26.6 kb mainly from six regions) of the genome compared with ancestral CVA virus. The deletions affect a number of virulence and host range genes, as well as the genes required to form type A inclusion bodies. A sample of MVA-BN corresponding to passage 583 was deposited on Aug. 30, 2000 at the European Collection of Cell Cultures (ECACC) under number V00083008.

MVA-BN can attach to and enter human cells where virally-encoded genes are expressed very efficiently. However, assembly and release of progeny virus does not occur. MVA-BN is strongly adapted to primary chicken embryo fibroblast (CEF) cells and does not replicate in human cells. In human cells, viral genes are expressed, and no infectious virus is produced. MVA-BN is classified as Biosafety Level 1 organism according to the Centers for Disease Control and Prevention in the United States. Preparations of MVA-BN and derivatives have been administered to many types of animals, and to more than 4000 human subjects, including immune-deficient individuals. All vaccinations have proven to be generally safe and well tolerated. Despite its high attenuation and reduced virulence, in preclinical studies MVA-BN has been shown to elicit both humoral and cellular immune responses to vaccinia and to heterologous gene products encoded by genes cloned into the MVA genome [E. Harrer et al. (2005), *Antivir. Ther.* 10(2):285-300; A. Cosma et al. (2003), *Vaccine* 22(1):21-9; M. Di Nicola et al. (2003), *Hum. Gene Ther.* 14(14):1347-1360; M. Di Nicola et al. (2004), *Clin. Cancer Res.,* 10(16):5381-5390].

The terms "derivatives" or "variants" of MVA refer to viruses exhibiting essentially the same replication charac-teristics as MVA as described herein, but exhibiting differ-ences in one or more parts of their genomes. MVA-BN as well as a derivative or variant of MVA-BN fails to repro-ductively replicate in vivo in humans and mice, even in severely immune suppressed mice. More specifically, MVA-BN or a derivative or variant of MVA-BN has preferably also the capability of reproductive replication in chicken embryo fibroblasts (CEF), but no capability of reproductive replication in the human keratinocyte cell line HaCat [Bou-kamp et al (1988), *J. Cell. Biol.* 106: 761-771], the human bone osteosarcoma cell line 143B (ECACC No. 91112502), the human embryo kidney cell line 293 (ECACC No. 85120602), and the human cervix adenocarcinoma cell line HeLa (ATCC No. CCL-2). Additionally, a derivative or variant of MVA-BN has a virus amplification ratio at least two-fold less, more preferably three-fold less than MVA-575 in Hela cells and HaCaT cell lines. Tests and assay for these properties of MVA variants are described in WO 02/42480 (US 2003/0206926) and WO 03/048184 (US 2006/0159699), both incorporated herein by reference.

The amplification or replication of a virus is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The advantages of MVA-based vaccine include their safety profile as well as availability for large scale vaccine production. Preclinical tests have revealed that MVA-BN demonstrates superior attenuation and efficacy compared to other MVA strains (WO 02/42480). An additional property of MVA-BN strains is the ability to induce substantially the same level of immunity in vaccinia virus prime/vaccinia virus boost regimes when compared to DNA-prime/vaccinia virus boost regimes.

The recombinant MVA-BN viruses, the most preferred embodiment described herein, are considered to be safe because of their distinct replication deficiency in mamma-lian cells and their well-established avirulence. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

In another aspect, an MVA viral strain suitable for gen-erating the recombinant virus may be strain MVA-572, MVA-575 or any similarly attenuated MVA strain. Also suitable may be a mutant MVA, such as the deleted chorio-allantois vaccinia virus Ankara (dCVA). A dCVA comprises six deletion sites of the MVA genome, referred to as deletion I (del I), deletion II (del II), deletion III (del III), deletion IV (del IV), deletion V (del V), and deletion VI (del VI). The deletion sites are particularly useful for the insertion of multiple heterologous sequences. The dCVA can reproduc-tively replicate (with an amplification ratio of greater than 10) in a human cell line (such as human 293, 143B, and MRC-5 cell lines), which then enable the optimization by further mutation or attenuation useful for a virus-based vaccination strategy (see, e.g., WO 2011/092029).

Prime-boost vaccination. The term "prime-boost vaccina-tion" refers to a vaccination strategy using a first, priming injection of a vaccine targeting a specific antigen followed at intervals by one or more boosting injections of the same vaccine antigen. Prime-boost vaccination may be homolo-gous or heterologous with respect to the vaccine modality (RNA, DNA, protein, vector, virus-like particle) delivering the vaccine antigen. A homologous prime-boost vaccination uses a vaccine comprising the same immunogen and vector for both the priming injection and the one or more boosting injections. A heterologous prime-boost vaccination uses a vaccine comprising the same immunogen for both the prim-ing injection and the one or more boosting injections but different vectors for the priming injection and the one or more boosting injections. For example, a homologous prime-boost vaccination may use an MVA vector comprising nucleic acids expressing an immunogen and TRICOM for both the priming injection and the one or more boosting injections. In contrast, a heterologous prime-boost vaccina-tion may use an MVA vector comprising nucleic acids expressing an immunogen and TRICOM for the priming injection and a fowlpox vector comprising nucleic acids expressing an immunogen and TRICOM for the one or more boosting injections. Heterologous prime-boost vaccination also encompasses various combinations such as, for example, use of a plasmid encoding an immunogen in the priming injection and use of a poxvirus vector encoding the same immunogen in the one or more boosting injections, or use of a recombinant protein immunogen in the priming injection and use of a plasmid or poxvirus vector encoding the same protein immunogen in the one or more boosting injections.

Recombinant; recombinant nucleic acid; recombinant vector; recombinant poxvirus. The term "recombinant" when applied to a nucleic acid, vector, poxvirus and the like refers to a nucleic acid, vector, or poxvirus made by an artificial combination of two or more otherwise heterologous segments of nucleic acid sequence, or to a nucleic acid, vector or poxvirus comprising such an artificial combination of two or more otherwise heterologous segments of nucleic acid sequence. The artificial combination is most commonly accomplished by the artificial manipulation of isolated segments of nucleic acids, using well-established genetic engineering techniques.

Sequence identity. The term "sequence identity" refers to the degree of identity between the nucleic acid or amino acid sequences. Sequence identity is frequently measured in terms of percent identity (often described as sequence "similarity" or "homology"). The higher the percent sequence identity, the more similar the two sequences are. Homologs or variants of a protein immunogen will have a relatively high degree of sequence identity when aligned using standard methods.

Methods of aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucl. Acids Res.* 16:10881, 1988; and Pearson and Lipman, *Proc. Nat'l Acad. Sci. USA* 85:2444, 1988. In addition, Altschul et al., *Nature Genet.* 6:119, 1994, presents a detailed consideration of sequence alignment methods and homology calculations. The NCBI Basic Local Alignment Search Tool (BLAST) (Altschul et al., *J. Mol. Biol.* 215:403, 1990) is available from several sources, including the National Center for Biotechnology Information (NCBI, Bethesda, MD; see also blast.ncbi.nlm.nih.gov/Blast.cgi), for use in connection with the sequence analysis programs blastp, blastn, blastx, tblastn and tblastx.

Homologs and variants of a protein immunogen typically have at least 90%, 91%, 92%, 93%, 94%, 95%, 96%, 97%, 98% or 99% amino acid sequence identity over a full-length alignment with the amino acid sequence of the wild-type immunogen prepared with NCBI Blast v2.0, using blastp set to the default parameters. For comparisons of amino acid sequences of greater than about 30 amino acids, the Blast 2 sequences function is employed using the default BLOSUM62 matrix set to the default parameters (gap existence cost of 11, and a per residue gap cost of 1).

Subject. Living multi-cellular vertebrate organisms, including, for example, humans, non-human mammals and birds. The term "subject" may be used interchangeably with the terms "mammal" or "animal" herein.

T-Cell. A lymphocyte or white blood cell essential to the adaptive immune response. T-cells include, but are not limited to, CD4$^+$ T-cells and CD8$^+$ T-cells. A CD4$^+$ T-cell is an immune cell that carries a marker on its surface known as "cluster of differentiation 4" ("CD4"). These cells, also known as helper T-cells, help orchestrate the immune response, including both antibody and CTL responses. CD8$^+$ T-cells carry the "cluster of differentiation 8" ("CD8") marker. CD8$^+$ T-cells include both CTLs, memory CTLs, and suppressor T-cells.

Therapeutically active polypeptide. An agent composed of amino acids, such as a protein, that induces a biological effect and/or an adaptive immune response, as measured by clinical response (e.g., an increase in CD4$^+$ T-cells, CD8$^+$ T-cells, or B-cells, an increase in protein expression level, a measurable reduction in tumor size, or a reduction in number of metastases). Therapeutically active molecules can also be made from nucleic acids such as, for example, a poxvirus vector comprising a nucleic acid encoding a protein or protein immunogen operably linked to an expression control sequence.

Therapeutically effective amount. A "therapeutically effective amount" is a quantity of a composition or a cell sufficient to achieve a desired therapeutic or clinical effect in a subject being treated. For example, a therapeutically effective amount of a poxviral vector comprising a nucleic acid encoding a protein or protein immunogen operably linked to an expression control sequence would be an amount sufficient to elicit a biologic response or an antigen-specific immune response or to reduce or eliminate clinical signs or symptoms of an infectious or other disease in a patient or population of patients having a disease or disorder. A therapeutically effective amount of the poxvirus vectors and compositions comprising the poxvirus vectors provided herein is an amount sufficient to raise an immune response to cells expressing the target antigen. The immune response must be of sufficient magnitude to reduce or eliminate clinical signs or symptoms of disease in a patient or population of patients having the targeted disorder.

Transduced or Transformed. The term "transduced" or "transformed" refers to a cell into which a recombinant nucleic acid has been introduced by standard molecular biological methods. As used herein, the term transduction encompasses all techniques by which a nucleic acid molecule might be introduced into such a cell, including infection with viral vectors, transformation with plasmid vectors, and introduction of naked DNA by electroporation, lipofection, or particle gun acceleration.

TRICOM. A Triad of COstimlatory Molecules consisting of B7-1 (also known as CD80), intracellular adhesion molecule-1 (ICAM-1, also known as CD54) and lymphocyte function-associated antigen-3 (LFA-3, also known as CD58), commonly included in recombinant viral vectors (e.g., poxviral vectors) expressing a specific antigen in order to increase the antigen-specific immune response. The individual components of TRICOM can be under the control of the same or different promoters, and can be provided on the same vector with the specific antigen or on a separate vector. Exemplary vectors are disclosed, for example, in Hodge et al., "A Triad of Costimulatory Molecules Synergize to Amplify T-Cell Activation," *Cancer Res.* 59:5800-5807 (1999) and U.S. Pat. No. 7,211,432 B2, both of which are incorporated herein by reference.

Vector. A carrier introducing a nucleic acid molecule of interest into a host cell, thereby producing a transduced or transformed host cell. Vectors generally include nucleic acid sequences enabling them to replicate in a host cell, such as an origin of replication, as well as one or more selectable marker genes, expression control sequences, restriction endonuclease recognition sequences, primer sequences and a variety of other genetic elements known in the art. Commonly used vector types include plasmids for expression in bacteria (e.g., *E. coli*) or yeast (e.g., *S. cerevisiae*), shuttle vectors for constructing recombinant poxviruses, cosmids, bacterial artificial chromosomes, yeast artificial chromosomes, and viral vectors. Viral vectors include poxvirus vectors, retrovirus vectors, adenovirus vectors, herpes virus vectors, baculovirus vectors, Sindbis virus vectors, and poliovirus vectors, among others.

Poxvirus vectors include, but are not limited to orthopox viruses, avipox viruses, parapox viruses, yatapox viruses, and molluscipox viruses, but preferably the orthopox and/or avipox viruses, as defined in more detail above. Orthopox viruses include smallpox virus (also known as variola virus), vaccinia virus, cowpox virus, and monkeypox virus. Avipox viruses include canarypox virus and fowlpox virus. The term "vaccinia virus" refers to both the wild-type vaccinia virus and any of the various attenuated strains or isolates subsequently isolated including, for example, vaccinia virus-Western Reserve, vaccinia virus-Copenhagen, Dryvax (also known as vaccinia virus-Wyeth), ACAM2000, modified vaccinia virus Ankara ("MVA"), and modified vaccinia virus Ankara-Bavarian Nordic ("MVA-BN").

Recombinant Poxviruses

In one aspect, provided herein are recombinant poxviruses comprising heterologous nucleic acids expressing early double-stranded RNA (dsRNA). In certain embodiments, the recombinant poxviruses comprise heterologous nucleic acids expressing excess dsRNA within 1 or 2 hours post-infection. In certain embodments, provided herein are recombinant poxviruses comprising heterologous nucleic acids expressing early or excess dsRNA prior to genome replication of said recombinant poxvirus. In certain embodiments, the recombinant poxviruses comprising heterologous nucleic acids expressing early ds RNA within 1 or 2 hours post-infection. In certain embodiments, the recombinant poxviruses can comprise a single heterologous nucleic acid from which both strands are transcribed to generate early dsRNA. In certain embodiments, the recombinant poxviruses can comprise an additional promoter directing early antisense transcription of an early transcribed native poxvirus gene, thus expressing early dsRNA. In certain embodiments, the recombinant poxviruses generating early dsRNA further comprise nucleic acid sequences encoding a heterologous disease-associated antigen. In certain embodiments, the recombinant poxvirus further comprises nucleic acid sequences encoding one or more costimulatory molecules. In certain embodiments, the one or more costimulatory molecules is TRICOM (i.e., B7-1, ICAM-1 and LFA-3). In certain embodiments, the heterologous disease-associated antigen is an infectious disease-associated antigen or a tumor-associated antigen. In certain embodiments, the heterologous diseaseassociated antigen is an infectious disease antigen. In certain embodiments, the infectious disease antigen is a viral antigen, a bacterial antigen, a fungal antigen, or a parasite antigen.

In certain embodiments, the infectious disease antigen is a viral antigen. In certain embodiments, the viral antigen is derived from a virus selected from the group consisting of adenovirus, Coxsackievirus, Crimean-Congo hemorrhagic fever virus, cytomegalovirus (CMV), dengue virus, Ebola virus, Epstein-Barr virus (EBV), Guanarito virus, herpes simplex virus-type 1 (HSV-1), herpes simplex virus-type 2 (HSV-2), human herpesvirus-type 8 (HHV-8), hepatitis A virus (HAV), hepatitis B virus (HBV), hepatitis C virus (HCV), hepatitis D virus (HDV), hepatitis E virus (HEV), human immunodeficiency virus (HIV), influenza virus, Junin virus, Lassa virus, Machupo virus, Marburg virus, measles virus, human metapneumovirus, mumps virus, Norwalk virus, human papillomavirus (HPV), parainfluenza virus, parvovirus, poliovirus, rabies virus, respiratory syncytial virus (RSV), rhinovirus, rotavirus, rubella virus, Sabia virus, severe acute respiratory syndrome virus (SARS), varicella zoster virus, variola virus, West Nile virus, and yellow fever virus.

In certain embodiments, the infectious disease antigen is a bacterial antigen. In certain embodiments, the bacterial antigen is derived from a bacterium selected from the group consisting of *Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diptheriae, Enterococcus faecalis, Enterococcus fae-*

*cium, Escherichia coli,* enterotoxigenic *Escherichia coli,* enteropathogenic *Escherichia coli, Escherichia coli* 157:H7, *Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae,* and *Yersinia pestis.*

In certain embodiments, the infectious disease antigen is a fungal antigen. In certain embodiments, the fungal antigen is derived from a fungus selected from the group consisting of *Aspergillus clavatus, Aspergillus flavus, Aspergillus fumigatus, Aspergillus nidulans, Aspergillus niger, Aspergillus terreus, Blastomyces dermatitidis, Candida albicans, Candida dubliniensis, Candida glabrata, Candida parapsilosis, Candida rugosa, Candida tropicalis, Cryptococcus albidus, Cryptococcus gattii, Cryptococcus laurentii, Cryptococcus neoformans, Histoplasma capsulatum, Microsporum canis, Pneumocystis carinii, Pneumocystis jirovecii, Sporothrix schenckii, Stachbotrys chartarum, Tinea barbae, Tinea captitis, Tinea corporis, Tinea cruris, Tinea faciei, Tinea incognito, Tinea nigra, Tinea versicolor, Trichophyton rubrum* and *Trichophyton tonsurans.*

In certain embodiments, the infectious disease antigen is a parasite antigen. In certain embodiments, the parasite antigen is derived from a parasite selected from the group consisting of *Anisakis* spp. *Babesia* spp., *Baylisascaris procyonis, Cryptosporidium* spp., *Cyclospora cayetanensis, Diphyllobothrium* spp., *Dracunculus medinensis, Entamoeba histolytica, Giardia duodenalis, Giardia intestinalis, Giardia lamblia, Leishmania* sp., *Plasmodium falciparum, Schistosoma mansoni, Schistosoma haematobium, Schistosoma japonicum, Taenia* spp., *Toxoplasma gondii, Trichinella spiralis,* and *Trypanosoma cruzi.*

In certain embodiments, the heterologous disease-associated antigen is a tumor-associated antigen. In certain embodiments, the tumor-associated antigen is selected from the group consisting of 5-α-reductase, α-fetoprotein (AFP), AM-1, APC, April, B melanoma antigen gene (BAGE), β-catenin, Bcl12, bcr-abl, Brachyury, CA-125, caspase-8 (CASP-8, also known as FLICE), Cathepsins, CD19, CD20, CD21/complement receptor 2 (CR2), CD22/BL-CAM, CD23/F$_c$εRII, CD33, CD35/complement receptor 1 (CR1), CD44/PGP-1, CD45/leucocyte common antigen (LCA), CD46/membrane cofactor protein (MCP), CD52/CAM-PATH-1, CD55/decay accelerating factor (DAF), CD59/protectin, CDC27, CDK4, carcinoembryonic antigen (CEA), c-myc, cyclooxygenase-2 (cox-2), deleted in colorectal cancer gene (DCC), DcR3, E6/E7, CGFR, EMBP, Dna78, farnesyl transferase, fibroblast growth factor-8a (FGF8a), fibroblast growth factor-8b (FGF8b), FLK-1/KDR, folic acid receptor, G250, G melanoma antigen gene family (GAGE-family), gastrin 17, gastrin-releasing hormone, ganglioside 2 (GD2)/ganglioside 3 (GD3)/ganglioside-monosialic acid-2 (GM2), gonadotropin releasing hormone (GnRH), UDP-GlcNAc:R$_1$Man(α1-6)R$_2$ [GlcNAc to Man(α1-6)]; β1,6-N-acetylglucosaminyltransferase V (GnT V), GP1, gp100/Pme117, gp-100-in4, gp15, gp75/tyrosine-related protein-1 (gp75/TRP-1), human chorionic gonadotropin (hCG), heparanase, Her2/neu, human mammary tumor virus (HMTV), 70 kiloDalton heat-shock protein (HSP70), human telomerase reverse transcriptase (hTERT), insulin-like growth factor receptor-1 (IGFR-1), interleukin-13 receptor (IL-13R), inducible nitric oxide synthase (iNOS), Ki67, KIAA0205, K-ras, H-ras, N-ras, KSA, LKLR-FUT, melanoma antigen-encoding gene 1 (MAGE-1), melanoma antigen-encoding gene 2 (MAGE-2), melanoma antigen-encoding gene 3 (MAGE-3), melanoma antigen-encoding gene 4 (MAGE-4), mammaglobin, MAP17, Melan-A/melanoma antigen recognized by T-cells-1 (MART-1), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor (PDGF), μPA, PRAME, probasin, progenipoietin, prostate-specific antigen (PSA), prostate-specific membrane antigen (PSMA), RAGE-1, Rb, RCAS1, SART-1, SSX-family, STAT3, STn, TAG-72, transforming growth factor-alpha (TGF-α), transforming growth factor-beta (TGF-β), Thymosin-beta-15, tumor necrosis factor-alpha (TNF-α), TP1, TRP-2, tyrosinase, vascular endothelial growth factor (VEGF), ZAG, p16INK4, and glutathione-S-transferase (GST).

In certain embodiments, the recombinant poxvirus is a member of the subfamily Chordopoxvirinae or the subfamily Entomopoxvirinae. In certain embodiments, the recombinant poxvirus is a member of the subfamily Chordopoxvirinae. In certain embodiments, the recombinant poxvirus is a member of a Chordopoxvirinae genera selected from the group consisting of avipox viruses, capripox viruses, leporipox viruses, molluscipox viruses, orthopox viruses, parapox viruses, suipoxviruses, and yatapox viruses. In certain embodiments, the recombinant poxvirus is an avipox virus. In certain embodiments, the avipox virus is selected from the group consisting of canarypox virus, fowlpox virus, mynahpox virus, pigeonpox virus, and quailpox virus. In certain embodiments, the recombinant poxvirus is a capripox virus. In certain embodiments, the capripox virus is selected from the group consisting of sheeppox virus, goatpox virus, and lumpy skin disease virus. In certain embodiments, the recombinant poxvirus is a leporipox virus. In certain embodiments, the leporipox virus is selected from the group consisting of myxoma virus, Shope fibroma virus (also known as rabbit fibroma virus), hare fibroma virus, and squirrel fibroma virus. In certain embodiments, the recombinant poxvirus is a molluscipox virus. In certain embodiments, the molluscipox virus is Molluscum contagiosum virus. In certain embodiments, the recombinant poxvirus is an orthopox virus. In certain embodiments, the orthopox virus is selected from the group consisting buffalopox virus, camelpox virus, cowpox virus, ectromelia virus, monkeypox virus, raccoonpox virus, smallpox virus (also known as variola virus), and vaccinia virus. In certain embodiments, the orthopox virus is vaccinia virus. In certain embodiments, the vaccinia virus is selected from the group consisting of vaccinia virus-Western Reserve, vaccinia virus-Copenhagen, Dryvax (also known as vaccinia virus-Wyeth), ACAM2000, chorioallantois vaccinia virus Ankara ("CVA"), modified vaccinia virus Ankara ("MVA"), and modified vaccinia virus Ankara-Bavarian Nordic ("MVA-BN"). In certain embodiments, the recombinant poxvirus is a parapox virus. In certain embodiments, the parapox virus is selected from the group consisting of bovine papular stomatitis virus, ORF virus, parapoxvirus of New Zealand red deer, and pseudocowpox virus. In certain embodiments, the recombinant poxvirus is a suipox virus. In certain embodiments, the suipox virus is swinepox virus. In certain embodiments, the recombinant poxvirus is a yatapox virus.

In certain embodiments, the yatapox virus is selected from the group consisting of tanapox virus and yaba monkey tumor virus.

In certain embodiments, the heterologous nucleic acids expressing early dsRNA comprise sequences encoding complementary RNA transcripts, wherein the complementary RNA transcripts anneal after transcription to produce dsRNA. In certain embodiments, the complementary RNA transcripts comprise protein-encoding open reading frames (ORFs) or non-protein-coding genes. In certain embodiments, the complementary RNA transcripts or complementary portions of the RNA transcripts overlap by 50, 100, 150, 200, 250, 300, 350, 400, 450, 500, 550, 600, 650, 700, 750, 800, 850, 900, 950, or 1000 nucleotides. In certain embodiments, the complementary RNA transcripts overlap by more than 50, more than 100, more than 150, more than 200, more than 250, more than 300, more than 350, more than 400, more than 450, more than 500, more than 550, more than 600, more than 650, more than 700, more than 750, more than 800, more than 850, more than 900, more than 950, or more than 1000 nucleotides. In certain embodiments, the complementary RNA transcripts overlap by between 100 and 1000, between 200 and 1000, between 300 and 1000, between 400 and 1000, between 500 and 1000, between 600 and 1000, between 700 and 1000, between 800 and 1000, between 900 and 1000, between 200 and 900, between 300 and 800, between 400 and 700, between 300 and 750, between 300 and 730, or between 500 and 600 nucleotides.

In certain embodiments, the heterologous nucleic acids in transcribed into RNA with complementary nucleic acid or complementary sequence of preferably 50, 60, 70, 80, 90, 100% complementary sequence. In certain embodiments, the heterologous nucleic acids encoding complementary RNA transcripts comprise two complementary sequences. In certain embodiments, the complementary sequences are separated by one or more essential viral genes or non-complementary nucleic acid. In certain embodiments, the the identical or highly similar sequences encoding partially or completely complementary transcripts are separated by one or more essential viral genes. In certain embodiments, the heterologous nucleic acid encoding complementary RNA transcripts comprise two complementary sequences on separate transcripts or nucleic acids. In certain embodiments, a sense messenger RNA (mRNA) is transcribed from one complementary sequence and an anti-sense mRNA is transcribed from the other complementary sequence. In certain embodiments, a sense messenger RNA (mRNA) is transcribed from one of the two identical or highly similar sequences and an anti-sense mRNA is transcribed from the other identical or highly similar sequence. In certain embodiments, expression of the sequences encoding overlapping complementary RNA transcripts is directed by one or more poxviral promoters. In certain embodiments, the one or more poxviral promoters is an early promoter or an immediate-early promoter.

In certain embodiments, the complementary RNA transcript or portion of the RNA transcript comprises nucleotides on different nucleic acid molecules. In certain embodiments, the complementary portions of the RNA transcripts comprise nucleic acids other than siRNA or complementary RNA transcripts of short stretches such as e.g. 21 to 23 basepairs.

In certain embodiments, the poxviral promoter is an early promoter. In certain embodiments, the early promoter is selected from the group consisting of the Pr7.5 promoter, and the PrS promoter. In certain embodiments, the poxviral promoter is an immediate-early promoter. In certain embodiments, the immediate-early promoter is selected from the group consisting of the I3L promoter, the 30K promoter, the 40K promoter, the PrHyb promoter, the PrS5E promoter, the Pr4LS5E promoter, and the Pr13.5-long promoter.

Compositions

In another aspect, provided herein are immunogenic compositions comprising any of the recombinant poxviruses comprising heterologous nucleic acids expressing double-stranded RNA (dsRNA) provided herein, and optionally a pharmaceutically acceptable carrier or excipient. In certain embodiments, the immunogenic compositions comprise any of the recombinant poxviruses comprising heterologous nucleic acids expressing dsRNA provided herein, and further comprise nucleic acid sequences encoding any of the heterologous disease-associated antigens provided herein and optionally a pharmaceutically acceptable carrier or excipient.

In another aspect, provided herein are pharmaceutical compositions comprising any of the recombinant poxviruses comprising heterologous nucleic acids expressing early double-stranded RNA (dsRNA) provided herein, and a pharmaceutically acceptable carrier or excipient. In certain embodiments, the pharmaceutical compositions comprise any of the recombinant poxviruses comprising heterologous nucleic acids expressing dsRNA provided herein, and further comprise nucleic acid sequences encoding any of the heterologous disease-associated antigens provided herein and a pharmaceutically acceptable carrier or excipient.

The recombinant poxviruses used to prepare the immunogenic compositions and the pharmaceutical compositions provided herein comprise a suspension or solution of recombinant poxvirus particles having a concentration range from $10^4$ to $10^5$ $TCID_{50}$/ml, $10^5$ to $5\times10^8$ $TCID_{50}$/ml, $10^6$ to $10^8$ $TCID_{50}$/ml, or $10^7$ to $10^8$ $TCID_{50}$/ml. In certain embodiments, the compositions are formulated as single doses comprising between $10^6$ to $10^5$ $TCID_{50}$, or comprising $10^6$ $TCID_{50}$, $10^7$ $TCID_{50}$, $10^8$ $TCID_{50}$ or $5\times10^8$ $TCID_{50}$. The recombinant poxviruses disclosed herein are provided in a physiologically acceptable form based, for example, on experience in the preparation of poxvirus vaccines used for vaccination against smallpox as described by H. Stickl et al., *Dtsch. med. Wschr.* 99:2386-2392 (1974). For example, purified poxviruses can be stored at −80° C. at a titer of $5\times10^8$ $TCID_{50}$/ml, formulated in about 10 mM Tris, 140 mM NaCl, at pH 7.7. In certain embodiments, poxvirus preparations, e.g., $10^2$-$10^8$ or $10^2$-$10^5$ poxvirus particles, can be lyophilized in 100 ml of phosphate-buffered saline (PBS) in the presence of 2% (w/v) peptone and 1% (w/v) human serum albumin (HSA) and stored in an ampoule made of glass or other suitable material.

Alternatively, freeze-dried poxvirus particle preparations can be prepared by stepwise freeze-drying of a suspension of poxvirus particles formulated in a solution such as, for example, 10 mM Tris, 140 mM NaCl, at pH 7.7, or PBS plus 2% (w/v) peptone and 1% (w/v) HSA. In certain embodiments, the solution contains one or more additional additives such as mannitol, dextran, sugar, glycine, lactose or polyvinylpyrrolidone. In certain embodiments, the solution contains other aids such as antioxidants or inert gas, stabilizers or recombinant proteins (e.g., human serum albumin, or HSA) suitable for in vivo administration. The solutions are then aliquoted into appropriate storage vessels such as, for example, glass ampoules, and the storage vessels are sealed. In certain embodiments, the immunogenic and/or pharmaceutical compositions are stored at a temperature between 4° C. and room temperature for several months. In certain embodiments, the storage vessels are stored at a temperature below −20° C., below −40° C., below −60° C., or below −80° C.

In certain embodiments, the pharmaceutically acceptable carrier or excipient comprises one or more additives, antibiotics, preservatives, adjuvants, diluents and/or stabilizers. Such auxiliary substances can be water, saline, glycerol, ethanol, wetting or emulsifying agents, pH buffering substances, or the like. Generally the nature of the carrier used depends on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like, as a vehicle. Suitable carriers are typically large, slowly-metabolized molecules such as proteins, polysaccharides, polylactic acids, polyglycolic acids, polymeric amino acids, amino acid copolymers, lipid aggregates, or the like.

Methods and Uses

In another aspect, provided herein are methods of enhancing innate immune activation comprising administering any one of the pharmaceutical compositions or recombinant poxvirus provided herein to a subject in need thereof, wherein the pharmaceutical composition or recombinant poxvirus enhances innate immune activation when administered to a subject. In another aspect, provided herein is the use of any one of the pharmaceutical compositions or recombinant poxvirus provided herein in the manufacture of a medicament for the treatment or prevention of a condition mediated by a poxvirus or mediated by a heterologous disease-associated antigen. In another aspect, provided herein is a poxvirus or any one of the pharmaceutical compositions provided herein for use as a medicament. In another aspect, provided herein is a poxvirus of any one of the pharmaceutical compositions provided herein for use in enhancing innate immune activation or for the treatment of prevention of a condition mediated by a poxvirus or mediated by a heterologous disease-associated antigen. In another aspect, provided herein is the use of any one of the pharmaceutical compositions provided herein for the treatment or prevention of a condition mediated by a poxvirus or mediated by a heterologous disease-associated antigen. In certain embodiments, the subject is a vertebrate. In certain embodiments, the vertebrate is a mammal. In certain embodiments, the mammal is a human.

In certain embodiments, any of the pharmaceutical compositions comprising a recombinant poxvirus further comprising nucleic acid sequences encoding a heterologous disease-associated antigen provided herein, enhance innate immune activation compared to an identical pharmaceutical composition comprising a recombinant poxvirus lacking heterologous nucleic acids expressing excess early dsRNA when administered to a subject (whether the recombinant poxvirus further comprises nucleic acid sequences encoding a heterologous disease-associated antigen or not). In certain embodiments, the subject is a vertebrate. In certain embodiments, the vertebrate is a mammal. In certain embodiments, the mammal is a human.

In certain embodiments, any of the pharmaceutical compositions provided herein are administered to the subject by any suitable route of administration known to one or ordinary skill in the art. In certain embodiments, the pharmaceutical compositions are provided as a lyophilisate. In certain embodiments, the lyophilisate is dissolved in an aqueous solution. In certain embodiments, the aqueous solution is physiological saline, phosphate-buffered saline, or Tris buffer at physiological pH. In certain embodiments, the pharmaceutical compositions are administered systemically. In certain embodiments, the pharmaceutical compositions are administered locally. In certain embodiments, any of the pharmaceutical compositions provided herein are administered subcutaneously, intravenously, intramuscularly, intradermally, intranasally, orally, topically, parenterally, or by any other route of administration known to the skilled practitioner. The route of administration, dose, and treatment protocol can be optimized by those skilled in the art.

In certain embodiments, any of the pharmaceutical compositions provided herein are administered to the subject in a single dose. In certain embodiments, any of the pharmaceutical compositions provided herein are administered to the subject in multiple doses. In certain embodiments, any of the pharmaceutical compositions are administered to the subject in 2, 3, 4, 5, 6, 7, 8, 9, 10, 11, 12, 13, 14, 15, 16, 17, 18, 19, 20, 21, 22, 23, 24, 25 or more doses. In certain embodiments, any of the pharmaceutical compositions provided herein are administered in a first priming dose followed by administration of one or more additional boosting doses (i.e., administered by a 'prime-boost' vaccination protocol). In certain embodiments, the 'prime-boost' vaccination protocol is a homologous prime-boost protocol. In certain embodiments, the 'prime-boost' protocol is a heterologous prime-boost protocol. In certain embodiments, the first or priming dose comprises a dose of any of the pharmaceutical compositions provided herein, comprising $10^7$ to $10^8$ $TCID_{50}$ of any of the recombinant poxviruses provided herein. In certain embodiments, the second and subsequent boosting doses comprises a dose of any of the pharmaceutical compositions provided herein, comprising $10^7$ to $10^8$ $TCID_{50}$ of any of the recombinant poxviruses provided herein. In certain embodiments, the second or boosting dose is administered 1, 2, 3, 4, 5, 6, 7, or more days after the first or priming dose. In certain embodiments, the second or boosting dose is administered 1, 2, 3, 4, 5, 6, 7, 8, 9, 10, 11, 12 or more weeks after the first or priming dose. In certain embodiments, the second or boosting dose is administered 1, 2, 3, 4, 5, 6, 7, 8, 9, 10, 11, 12 or more months after the first or priming dose. In certain embodiments, the second or boosting dose is administered 1, 2, 3, 4, 5 or more years after the first or priming dose. In certain embodiments, subsequent boosting doses are administered 1, 2, 3, 4, 5, 6, 7, or more days after the first boosting dose. In certain embodiments, subsequent boosting doses are administered 1, 2, 3, 4, 5, 6, 7, 8, 9, 10, 11, 12 or more weeks after the first boosting dose. In certain embodiments, subsequent boosting doses are administered 1, 2, 3, 4, 5, 6, 7, 8, 9, 10, 11, 12 or more months after the first boosting dose. In certain embodiments, subsequent boosting doses are administered 1, 2, 3, 4, 5 or more years after the first boosting dose.

In certain embodiments, the enhanced innate immune response comprises enhanced production of type I interferons (type I IFNs), cytokines and chemokines.

In certain embodiments, the enhanced innate immune response comprises enhanced production of type I IFNs. In certain embodiments, the enhanced production of type I IFNs comprises enhanced transcription of interferon-beta (IFN-β)-encoding messenger RNA (mRNA). In certain embodiments, transcription of IFN-β-encoding mRNA increases by at least 2-fold, at least 4-fold, at least 6-fold, at least 8-fold, at least 10-fold, at least 20-fold, at least 30-fold, at least 40-fold, at least 50-fold, at least 100-fold or more. In certain embodiments, the enhanced production of type I IFNs comprises enhanced secretion of IFN-β-protein. In certain embodiments, secretion of IFN-β-protein increases by at least 2-fold, at least 4-fold, at least 6-fold, at least 8-fold, at least 10-fold, at least 20-fold, at least 30-fold, at least 40-fold, at least 50-fold, at least 100-fold or more.

In certain embodiments, the enhanced production of type I IFNs comprises enhanced transcription of interferon-alpha (IFN-α)-encoding mRNA, and transcription of IFN-α-encoding mRNA increases by at least 2-fold, at least 4-fold, at least 6-fold, at least 8-fold, at least 10-fold, at least 20-fold, at least 30-fold, at least 40-fold, at least 50-fold, at least 100-fold or more. In certain embodiments, the enhanced production of type I IFNs comprises enhanced secretion of IFN-α-protein, and secretion of IFN-α-protein increases by at least 2-fold, at least 4-fold, at least 6-fold, at least 8-fold, at least 10-fold, at least 20-fold, at least 30-fold, at least 40-fold, at least 50-fold, at least 100-fold or more.

In certain embodiments, the enhanced production of type I IFNs comprises enhanced transcription of interferon-gamma (IFN-γ)-encoding mRNA, and transcription of IFN-γ-encoding mRNA increases by at least 2-fold, at least 4-fold, at least 6-fold, at least 8-fold, at least 10-fold, at least 20-fold, at least 30-fold, at least 40-fold, at least 50-fold, at least 100-fold or more. In certain embodiments, the enhanced production of type I IFNs comprises enhanced secretion of IFN-γ-protein, and secretion of IFN-γ-protein increases by at least 2-fold, at least 4-fold, at least 6-fold, at least 8-fold, at least 10-fold, at least 20-fold, at least 30-fold, at least 40-fold, at least 50-fold, at least 100-fold or more.

In certain embodiments, the enhanced innate immune response comprises enhanced production of cytokines. In certain embodiments, the enhanced production of cytokines comprises enhanced transcription of interleukin-6 (IL-6)-encoding mRNA, and transcription of IL-6-encoding mRNA increased by at least 1.8-fold, at least 2-fold, at least 4-fold, at least 6-fold, at least 8-fold, at least 10-fold, at least 20-fold, at least 30-fold, at least 40-fold, at least 50-fold, at least 100-fold or more. In certain embodiments, the enhanced production of cytokines comprises enhanced secretion of IL-6-protein, and secretion of IL-6-protein increases by at least 2-fold, at least 4-fold, at least 6-fold, at least 8-fold, at least 10-fold, at least 20-fold, at least 30-fold, at least 40-fold, at least 50-fold, at least 100-fold or more.

In certain embodiments, the enhanced production of cytokines comprises enhanced transcription of interleukin-18 (IL-18)-encoding mRNA, and transcription of IL-18-encoding mRNA increases by at least 2-fold, at least 4-fold, at least 6-fold, at least 8-fold, at least 10-fold, at least 20-fold, at least 30-fold, at least 40-fold, at least 50-fold, at least 100-fold or more. In certain embodiments, the enhanced production of cytokines comprises enhanced secretion of IL-18-protein, and secretion of IL-18-protein increases by at least 2-fold, at least 4-fold, at least 6-fold, at least 8-fold, at least 10-fold, at least 20-fold, at least 30-fold, at least 40-fold, at least 50-fold, at least 100-fold or more.

In certain embodiments, the enhanced innate immune response comprises enhanced production of chemokines. In certain embodiments, the enhanced production of chemokines comprises enhanced transcription of CXCL1-encoding mRNA, and transcription of CXCL1-encoding mRNA increases by at least 2-fold, at least 4-fold, at least 6-fold, at least 8-fold, at least 10-fold, at least 20-fold, at least 30-fold, at least 40-fold, at least 50-fold, at least 100-fold or more. In certain embodiments, the enhanced production of chemokines comprises enhanced secretion of CXCL1-protein, and secretion of CXCL1-protein increases by at least 2-fold, at least 4-fold, at least 6-fold, at least 8-fold, at least 10-fold, at least 20-fold, at least 30-fold, at least 40-fold, at least 50-fold, at least 100-fold or more.

In certain embodiments, the enhanced production of chemokines comprises enhanced transcription of CCL2-encoding mRNA, and transcription of CCL2-encoding mRNA increases by at least 2-fold, at least 4-fold, at least 6-fold, at least 8-fold, at least 10-fold, at least 20-fold, at least 30-fold, at least 40-fold, at least 50-fold, at least 100-fold or more. In certain embodiments, the enhanced production of chemokines comprises enhanced secretion of CCL2-protein, and secretion of CCL2-protein increases by at least 2-fold, at least 4-fold, at least 6-fold, at least 8-fold, at least 10-fold, at least 20-fold, at least 30-fold, at least 40-fold, at least 50-fold, at least 100-fold or more.

In certain embodiments, the enhanced production of chemokines comprises enhanced transcription of CCL5-encoding mRNA, and transcription of CCL5-encoding mRNA increases by at least 2-fold, at least 4-fold, at least 6-fold, at least 8-fold, at least 10-fold, at least 20-fold, at least 30-fold, at least 40-fold, at least 50-fold, at least 100-fold or more. In certain embodiments, the enhanced production of chemokines comprises enhanced secretion of CCL5-protein, and secretion of CCL5-protein increases by at least 2-fold, at least 4-fold, at least 6-fold, at least 8-fold, at least 10-fold, at least 20-fold, at least 30-fold, at least 40-fold, at least 50-fold, at least 100-fold or more.

EXAMPLES

Example 1: A CVA Mutant Lacking B15 and Containing an Additional Neo$^r$ Cassette is Highly Attenuated We identified a highly attenuated CVA mutant using a recombination system based on the CVA genome cloned as a bacterial artificial chromosome (BAC), wherein the neo/rpsL cassette served positive/negative selection purposes during mutagenesis of the CVA-BAC (Meisinger-Henschel et al., 2010). The CVA wild-type virus contains an insertion of BAC control sequences and additional markers in the intergenic region between ORFs I3L and I4L to allow propagation of the circularized genome as a BAC in bacteria. These sequences include a neo-IRES-EGFP cassette expressed under the poxviral pS promoter. It has previously been demonstrated that this BAC-derived CVA has indistinguishable properties from the wild-type plaque-purified CVA (Meisinger 2010). The BAC-derived CVA is therefore considered to be indistinguishable from wild-type CVA and is referred to as CVA wt in the examples below.

Figure 1:
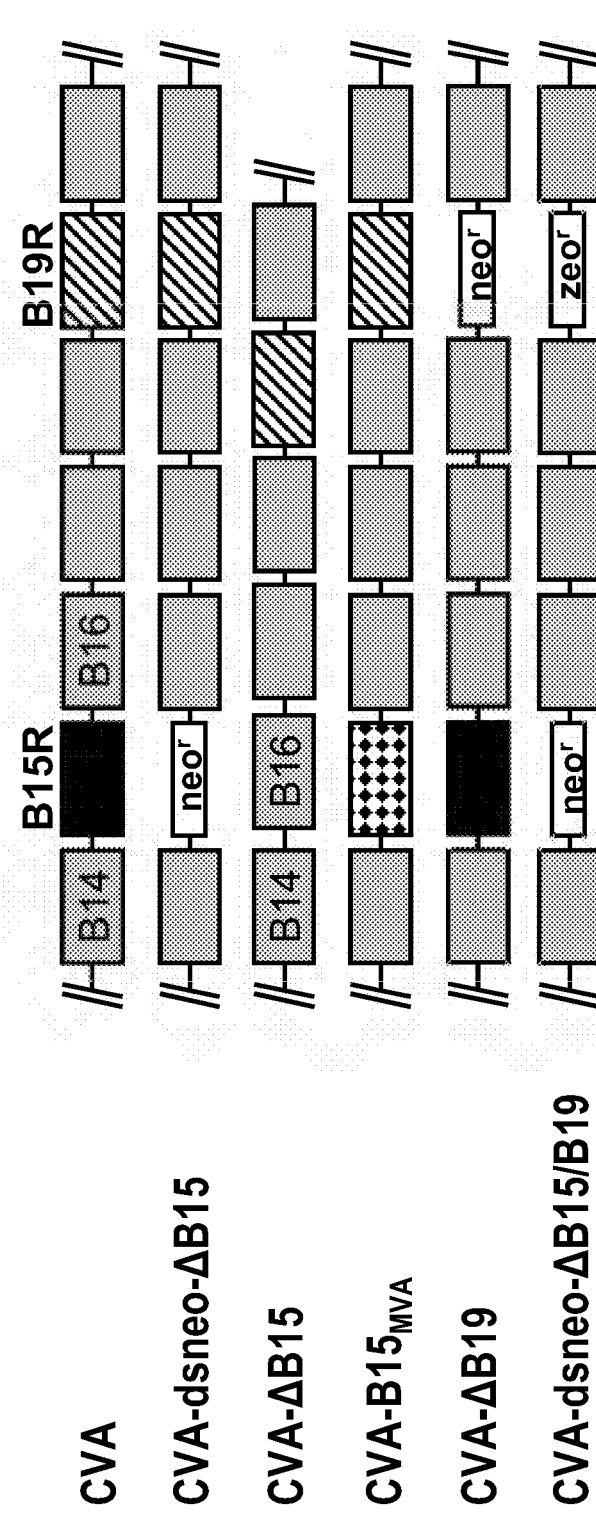
FIG. 1 depicts a schematic representation of CVA mutants overproducing early dsRNA and corresponding control mutants. Boxes represent CVA ORFs in the genomic region between ORFs B14R and B20R and are not drawn to scale. The box representing the CVA version of the B15 ORF is shown in black, whereas the MVA version of B15R is indicated by a diamond pattern. A hatched box represents the B19R ORF. All other ORFs are shown as grey boxes. The bacterial selection markers (neo$^r$ and zeo$^r$) replacing CVA ORFs in the various deletion mutants are shown as smaller boxes with an indication of the specific marker.
Figures 2A, 2B, 2C:
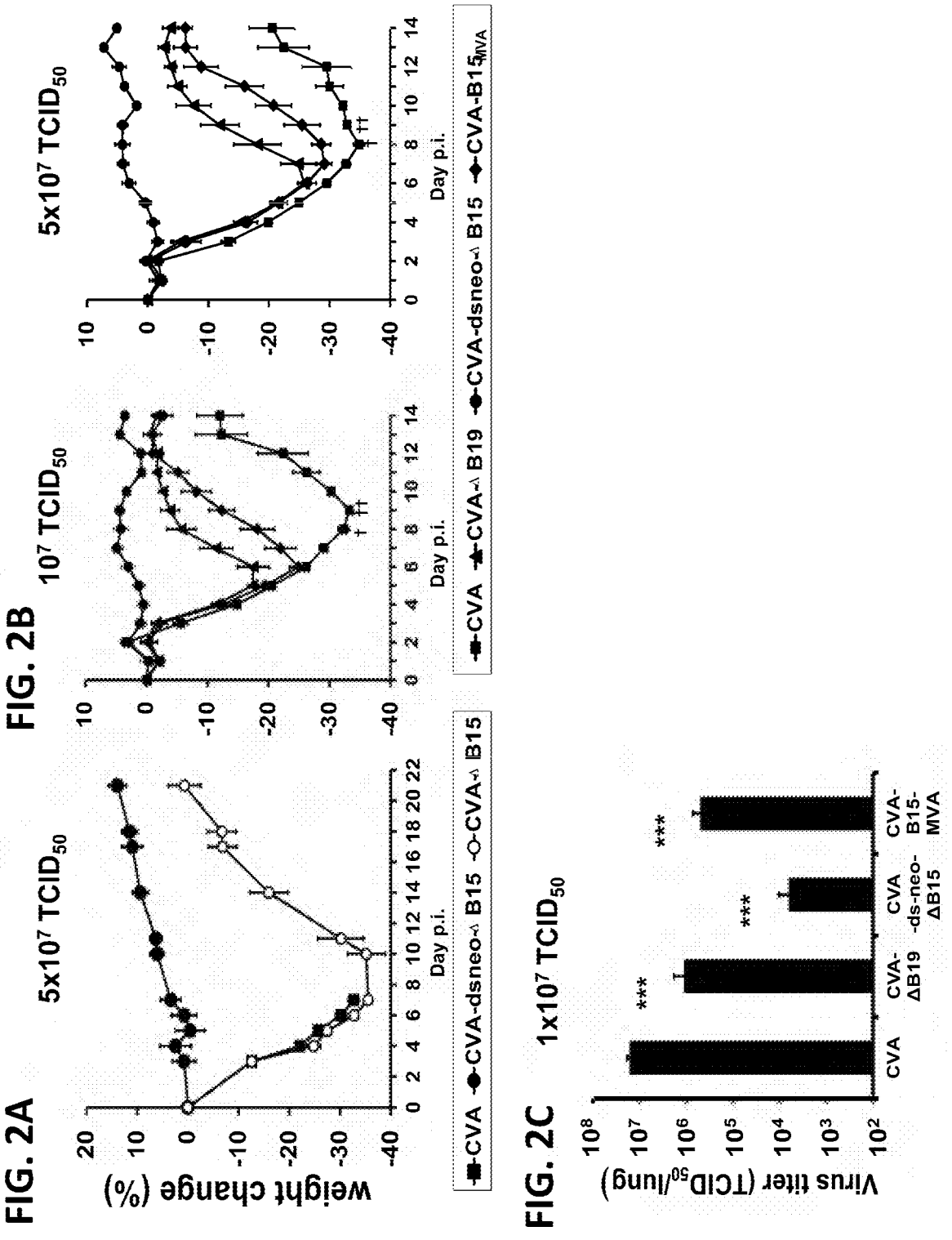
FIGS. 2A, 2B, and 2C show the virulence of CVA-dsneo-ΔB15 and related CVA mutants in BALB/c mice. Groups of three to five 6-8 week-old female BALB/c mice were infected intranasally with a 50 μl inoculum containing 5×10$^7$ (FIG. 2A, FIG. 2B right panel) or 10$^7$ TCID$_{50}$ (FIG. 2B left panel, FIG. 2C) of purified stock of the indicated CVA mutants.

Surprisingly, a mutant CVA harboring the neo/rpsL selection cassette in place of the B15R ORF (CVA-dsneo-ΔB15, see FIG. 1) was highly attenuated upon intranasal infection of BALB/c mice, while the CVA-ΔB15 deletion mutant without the neo/rpsL selection cassette was only moderately attenuated (FIG. 2A). Even after intranasal inoculation of mice with a dose of $5\times10^7$ TCID$_{50}$, CVA-dsneo-ΔB15 caused no detectable weight loss (FIGS. 2A and 2B) and no other disease symptoms (data not shown), whereas wild-type CVA is mostly lethal at this dose (FIGS. 2A and 2B). When the CVA version of B15R was replaced by the MVA version of B15R, the attenuation of the ensuing mutant CVA-B15$_{MVA}$ was also moderate (FIG. 2B), and comparable to the attenuation observed for CVA-ΔB15 (FIG. 2B). The B15 protein expressed by CVA-B15$_{MVA}$ migrated slightly faster in SDS-PAGE than its CVA homolog, confirming that CVA-B15$_{MVA}$ expressed the proper B15 version derived from MVA lacking 6 amino acids (data not shown). These results are consistent with the recently published observation that the MVA version of B15, which has an internal deletion of a stretch of six amino acids, is non-functional (McCoy et al. (2010), *J. Gen. Virol.* 91:2216-2220). Thus, CVA-B15$_{MVA}$ most probably represents a B15 null mutant.

As a reference for vaccinia virus attenuation, we deleted the B19R gene encoding the secreted IFN type I receptor of orthopoxviruses. CVA-ΔB19 was slightly more attenuated than CVA-ΔB15, but significantly less attenuated than CVA-dsneo-ΔB15 (FIG. 2B).

Infectious viral titers in lungs of mice were analyzed after intranasal infection with a dose of $1\times10^7$ TCID$_{50}$. Mice infected with CVA-dsneo-ΔB15 showed very low viral titers of less than $1\times10^4$ TCID$_{50}$ in lungs at six days post-infection, whereas viral titers in lungs of CVA-infected mice exceeded $1\times10^7$ TCID$_{50}$ (FIG. 2C, p<0.001 by Student's t test). Viral titers in lungs of mice infected with CVA-ΔB19 and CVA-B15$_{MVA}$ were reduced by approximately an order of magnitude (p<0.001) compared to those of CVA (FIG. 2C) reflecting the reduced but still significant pathogenicity of these viruses (FIG. 2B). Thus, infectious virus titers in lungs after intranasal infection correlated very well with the observed pathogenicity pattern of the CVA mutants and confirmed the strong attenuation of CVA-dsneo-ΔB15.

To exclude unwanted mutations in CVA-dsneo-ΔB15 as the cause of its severe attenuation, we determined the nucleotide sequences of the complete coding regions of CVA-dsneo-ΔB15 (202,615 nucleotides) and CVA-ΔB15 (201,296 nucleotides). Both viruses contained only the expected mutations, which had been deliberately introduced into their coding regions. Thus, the surprisingly strong attenuation of CVA-dsneo-ΔB15 appeared to depend on the presence of the neo/rpsL cassette.

Figures 3A, 3B:
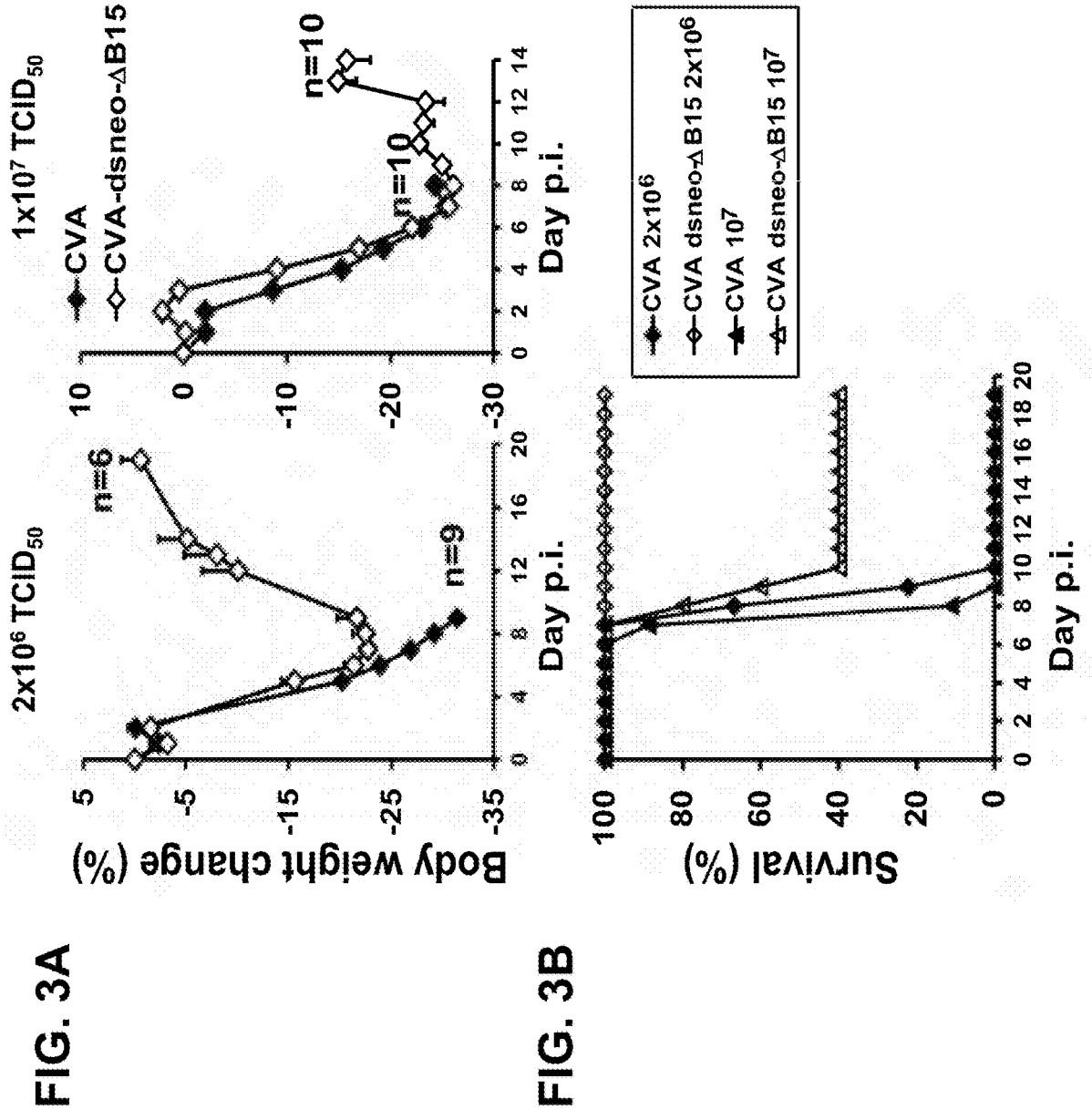
FIGS. 3A and 3B show the virulence of CVA-dsneo-ΔB15 in IFNAR$^{0/0}$ mice.

Example 2: Virulence of CVA-Dsneo-ΔB15 in IFN-α/β Receptor Deficient (IFNAR$^{0/0}$) Mice To investigate whether the IFN type I system contributed to the strong attenuation of CVA-dsneo-ΔB15 in mice, IFNAR$^{0/0}$ mice lacking a functional IFN α/β receptor were infected with graded doses of CVA and CVA-dsneo-ΔB15. At a high dose of $5\times10^7$ TCID$_{50}$, CVA-dsneo-ΔB15 was uniformly lethal for IFNAR$^{0/0}$ mice (data not shown). A subset of IFNAR$^{0/0}$ mice survived after infection with an intermediate dose of $1\times10^7$ of CVA-dsneo-ΔB15, and all mice survived when infected with a dose of $2\times10^6$ TCID$_{50}$ (FIGS. 3A and 3B). IFNAR$^{0/0}$ mice infected with wild-type CVA uniformly died even at the lowest dose of $2\times10^6$ TCID$_{50}$ (FIGS. 3A and 3B). Notably, CVA-dsneo-ΔB15 was still highly pathogenic for IFNAR$^{0/0}$ mice even at the lowest dose used of $2\times10^6$ TCID$_{50}$ as evidenced by significant weight loss of more than 20% (FIG. 3A).

Thus, the IFN type I system appears to be an important factor involved in the strong attenuation of CVA-dsneo-ΔB15. The fact that IFNAR$^{0/0}$ mice infected with doses of $2\times10^6$ and $1\times10^7$ TCID$_{50}$ of CVA-dsneo-ΔB15 partially or completely survived, whereas all IFNAR$^{0/0}$ mice infected with wt CVA died, suggested that IFN type I-independent factors contributed to the attenuation of CVA-dsneo-ΔB15 to a minor extent. B15 has been previously reported to be an inhibitor of NFκB activation in VACV infected cells (Chen et al. (2008), *PLoS. Pathog.* 4:e22-). Therefore, the antiviral effect of enhanced NFκB activation due to the lack of B15 might have been responsible for the moderate attenuation of CVA-dsneo-ΔB15 compared to CVA in IFNAR$^{0/0}$ mice. Along the same lines, less efficient NFκB inhibition might also provide an explanation for the moderate attenuation of CVA-ΔB15 in wild-type mice (FIGS. 2A, 2B, and 2C) since it lacks B15. However it is far less attenuated than CVA-dsneo-ΔB15 because it also lacks the neo/rpsL cassette, which is responsible for most of the attenuation of CVA-dsneo-ΔB15.

Example 3: IFN-α and IFN-λ Induction in Dendritic Cells (DCs) by CVA-Dsneo-ΔB15

Figure 4:
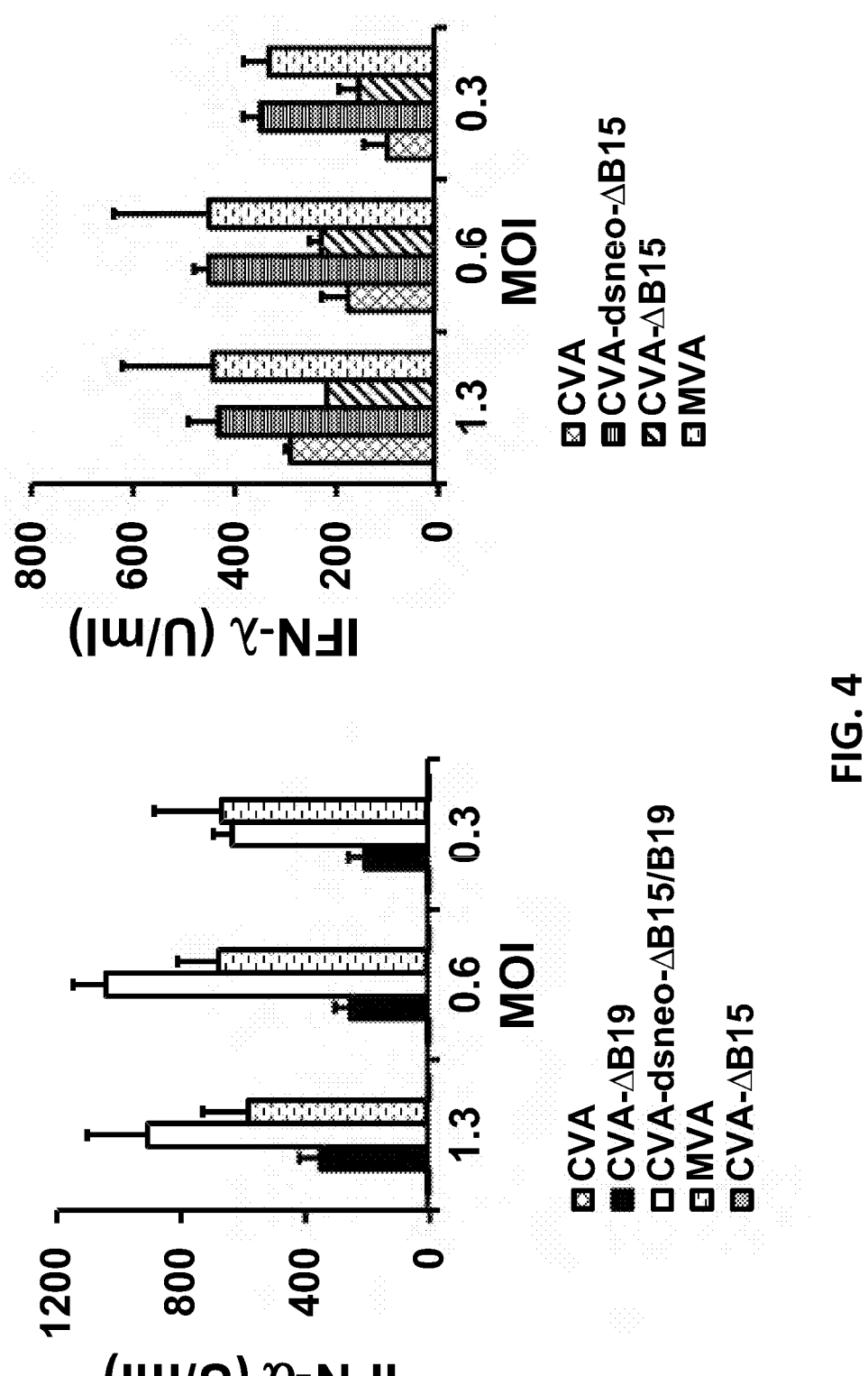
FIG. 4 shows IFN-α and IFN-λ, induction in DCs by CVA-dsneo-ΔB15. FL-DC from wild-type C57BL/6 mice were infected with the indicated viruses at the indicated MOIs for 18 h. DC culture supernatants were analyzed for IFN-α and IFN-λ by ELISA. CVA and CVA-ΔB15 did not induce detectable amounts of IFN-α.

Since DCs are efficient producers of type I and type III IFN, as well as of other cytokines, we evaluated the capacity of the various CVA constructs provided herein to induce these IFNs in murine bone marrow-derived DCs, which were generated using the fms-like tyrosine kinase 3 ligand (flt3-L or FL) culture system. Murine IFN-α, but not murine IFN-β, is bound by the orthopoxviral B19 protein. This binding partially or completely prevents detection of IFN-α in the IFN-α-specific ELISA (data not shown). To facilitate analysis of IFN-α induction by CVA-dsneo-ΔB15, an additional deletion was introduced by replacing the B19R gene with a zeocin resistance gene (FIG. 1). Attenuation of the resulting CVA-dsneo-ΔB15/B19 double deletion mutant was indistinguishable from that of CVA-dsneo-ΔB15 in the BALB/c disease model except that viral titers in lungs of infected mice were even lower at day six after infection (data not shown). While IFN-α was not detectable in supernatants of CVA-infected FL-DCs as expected, CVA-ΔB19 induced detectable amounts of IFN-α (FIG. 4) demonstrating that wild-type CVA is able to induce moderate levels of IFN-α, which are masked from ELISA-based detection by B19. The double deletion mutant CVA-dsneo-ΔB15/1319 induced significantly higher levels of IFN-α than CVA-ΔB19 in FL-DCs, which were comparable to those induced by MVA (FIG. 4). This demonstrated that the neo-ΔB15 mutation conferred higher interferon inducing capacity to CVA. B15 did not contribute to this effect since CVA-ΔB15 induced no detectable IFN-β, thus behaving like CVA wt.

Because orthopoxviruses do not express a binding protein for IFN-λ, we were able to directly analyze mutant CVA-dsneo-ΔB15 for its capacity to induce IFN-λ secretion by FL-DCs. CVA-dsneo-ΔB15 induced significantly higher IFN-λ levels in supernatants of FL-DCs than CVA or CVA-ΔB15 (FIG. 4). IFN-λ levels induced by CVA-dsneo-ΔB15 were very similar to those induced by MVA. Taken together, the above results indicate that CVA-dsneo-ΔB15 is a potent inducer of IFN-α and IFN-λ comparable to MVA which lacks a number of immunomodulators (Antoine et al. (1998), *Virology* 244:365-396; Meisinger-Henschel et al. (2007), *J. Gen. Virol.* 88:3249-3259) resulting in increased activation of DCs compared to its ancestor CVA (Samuelsson et al. (2008), *J. Clin. Invest* 118:1776-1784).

Example 4: IFN-β Induction in a Murine Cell Line by CVA and CVA-Dsneo-ΔB15

Figures 5A, 5B:
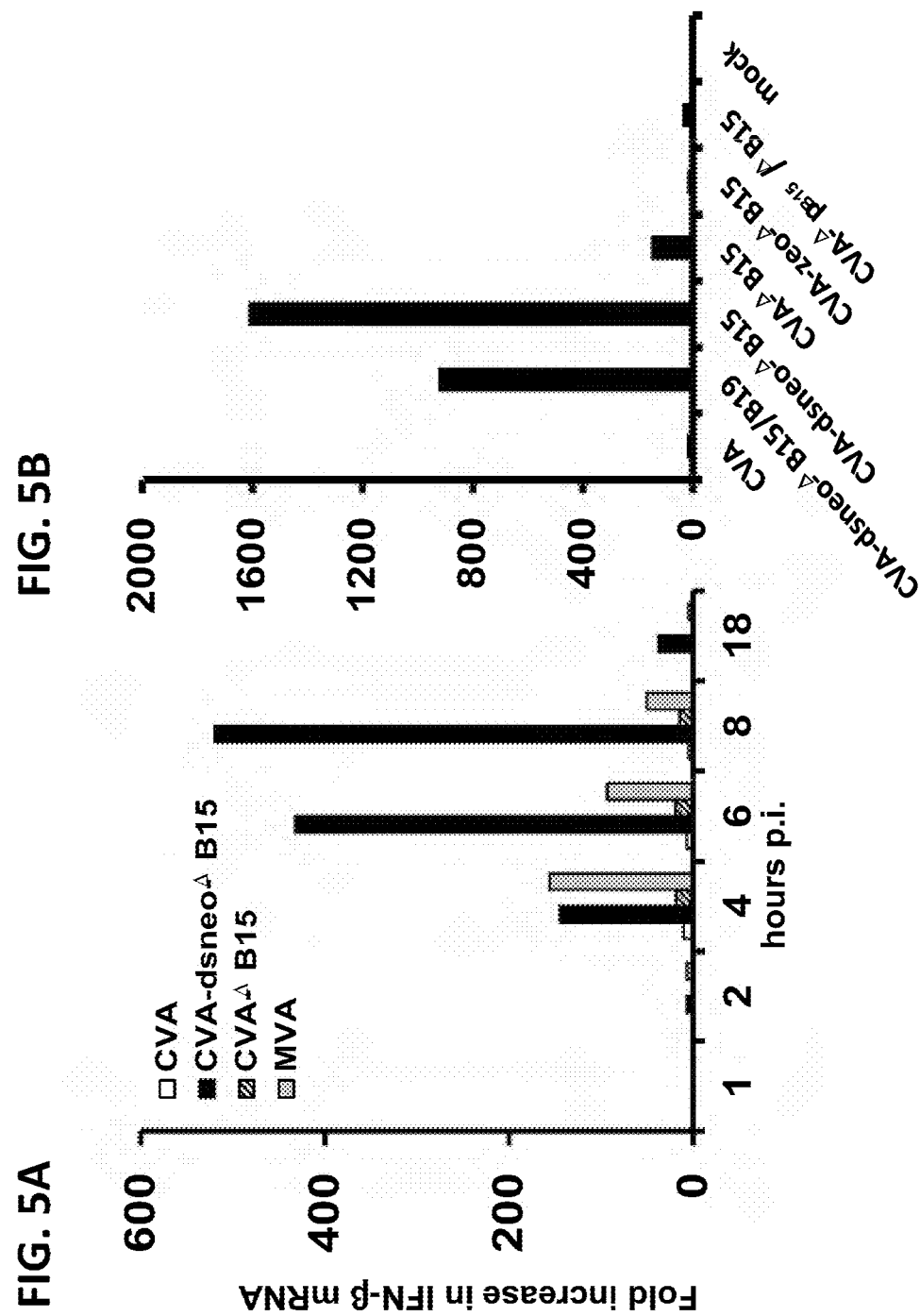
FIGS. 5A and 5B shows the kinetics of IFN-β mRNA induction by CVA-dsneo-ΔB15 in A31 cells by and the role of the neo cassette inserts.

To reveal whether the enhanced type I IFN-inducing capacity of CVA-dsneo-ΔB15 was confined to DCs, murine BALB/3T3 clone A31 (A31) fibroblast cells were infected with the various CVA constructs and IFN-β mRNA levels were determined by quantitative reverse transcriptase PCR (RT-qPCR). While CVA and CVA-ΔB15 induced only very low IFN-β gene expression, CVA-dsneo-ΔB15 infection stimulated increased levels of IFN-β transcripts in A31 cells (FIG. 5A). Induction of IFN-6 mRNA by CVA-dsneo-ΔB15 at 4 hours post-infection was similar to that obtained with MVA at this time point (FIG. 5A). Levels of IFN-β transcripts in MVA-infected A31 cells usually declined after 4 hours post-infection, whereas IFN-6 mRNA induced by CVA-dsneo-ΔB15 increased even further and clearly exceeded those induced by MVA from 6 hours post-infection onwards (FIG. 5A). These data in conjunction with the nearly complete reversal of attenuation of CVA-dsneo-ΔB15 in IFNAR$^{o/o}$ mice strongly suggest that the avirulence of this virus mutant in wild-type mice was likely caused by a strongly enhanced IFN type I induction.

When the neo ORF at the B15R locus of CVA-dsneo-ΔB15 was either deleted (CVA-ΔB15) or replaced by a zeocin (zeo) resistance cassette (CVA-zeo-ΔB15), the IFN-β stimulatory capacity of the resulting mutant viruses was almost completely absent (FIG. 5B). Since the neomycin ORF had been inserted in place of the B15R ORF leaving the strong early B15R promoter (pB15) intact, we deleted pB15 from CVA-dsneo-ΔB15. The resulting mutant CVA-Δp$_{B15}$-neo-ΔB15 induced only CVA wt levels of IFN-β transcripts (FIG. 5B). Thus, transcription of the neo ORF in the CVA-dsneo-ΔB15 mutant appeared to be essential for IFN-β stimulatory capacity. Neo cassette transcription in CVA-dsneo-ΔB15-infected A31 cells was confirmed by RT-qPCR analysis targeting the rpsL portion of the neo/rpsL insert (data not shown). The neo and rpsL ORFs had been inserted in reverse complementary orientation with respect to the B15 promoter and only a very short ORF is predicted to be translated from the neo cassette, should this antisense RNA be used by the translation machinery at all.

Since the CVA-dsneo-ΔB15 mutant expressed a second neo transcript in sense orientation under control of an early/late promoter from the EGFP/neo cassette in the BAC backbone, the neo sequences within the two partially complementary transcripts might form partially double-stranded RNA (dsRNA). This dsRNA most probably served as an additional PAMP in infected cells leading to enhanced induction of type I and type III IFNs.

Figure 6A:
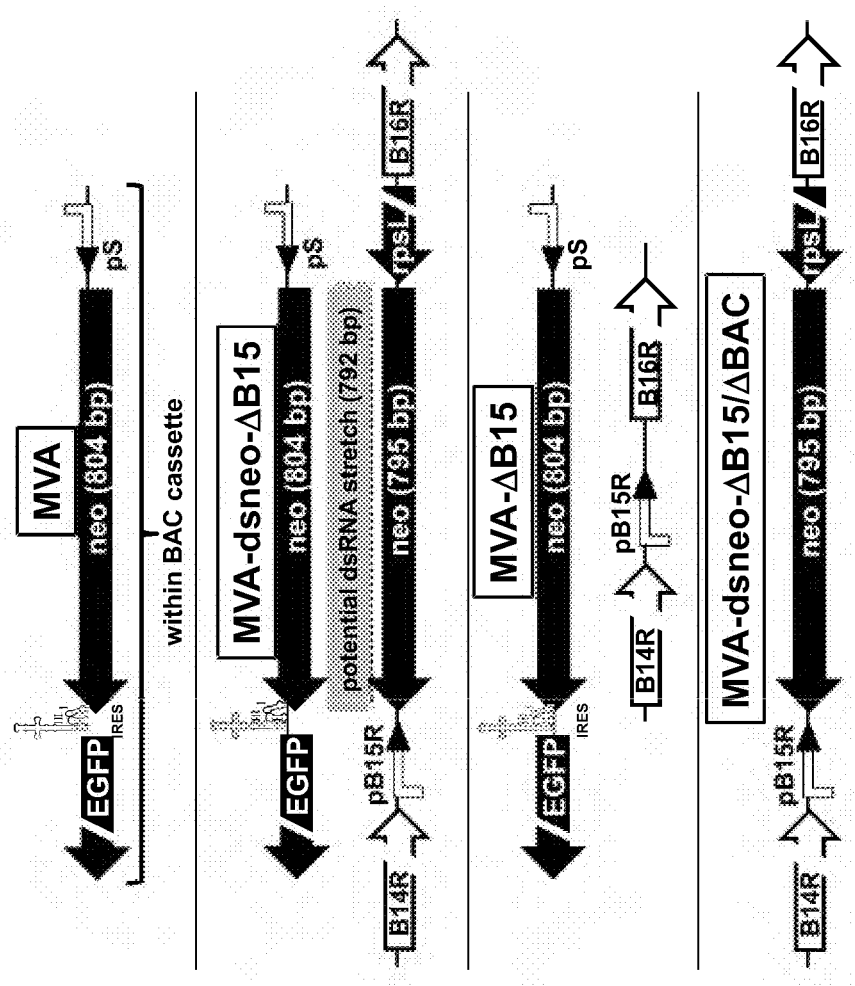
Figure 6B:
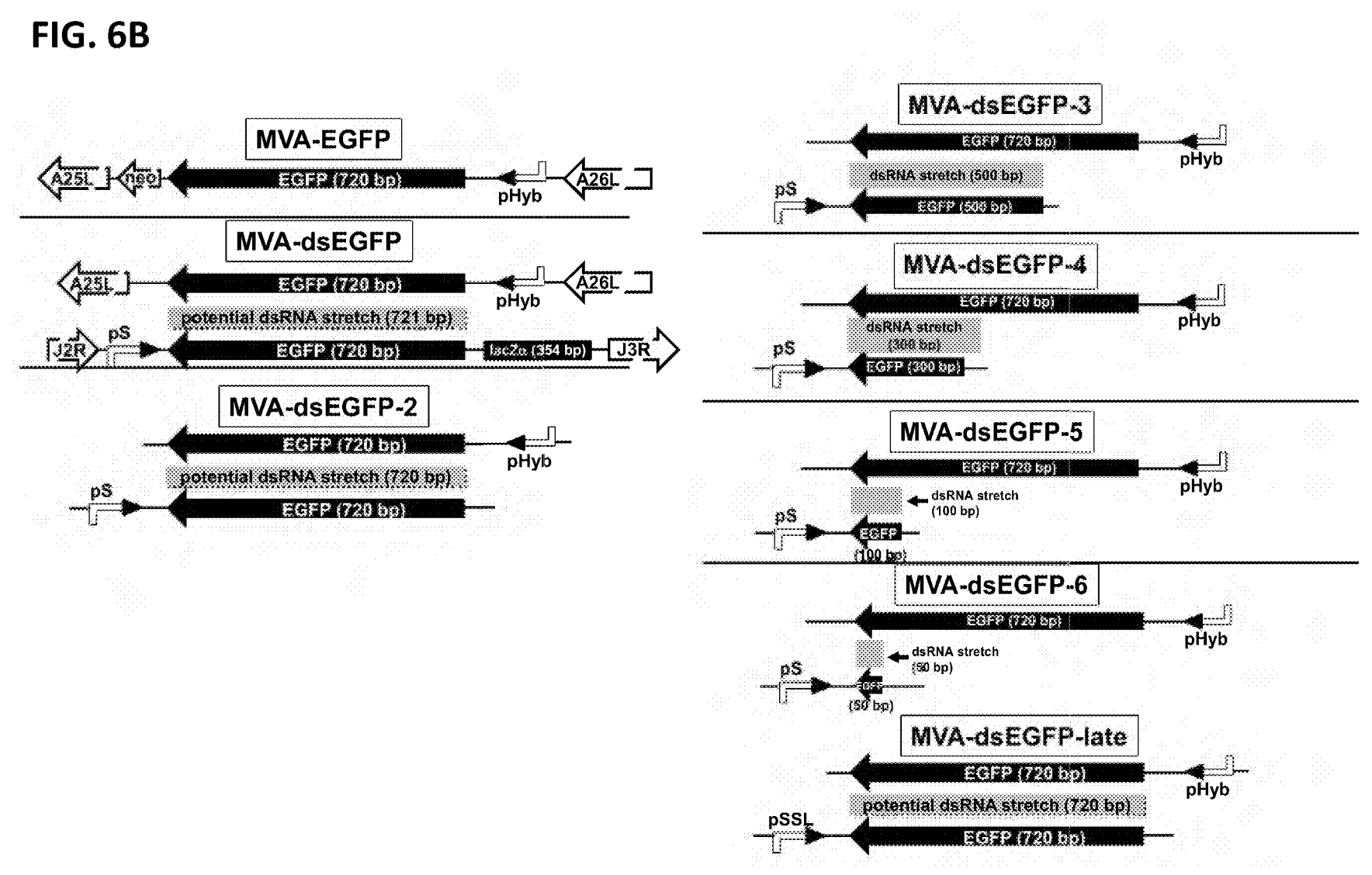

Example 5: MVA Vectors Expressing Complementary RNAs of Pairs of Foreign Inserts Induce IFN-β in Murine Cells To demonstrate applicability of the dsRNA principle to MVA, two pairs of recombinant MVA vectors expressing two complementary transcripts of either the neo or the EGFP gene were constructed. This was achieved by inserting two copies of the neo or the EGFP ORFs at sites distant from each other in the MVA genome, each under the control of a poxviral early/late promoter. The BAC-derived wild-type MVA already contained one copy of the neo/EGFP cassette within the BAC backbone insert (FIG. 6A). It has previously been demonstrated that the BAC cassette including the neo/EGFP cassette does not alter the properties of MVA and is thus equivalent to wild-type MVA (Meisinger-Henschel et al. (2010), *J. Virol.* 84: 9907-9919). MVA-dsneo-ΔB15 contained a second neo ORF at the B15R locus in reverse orientation relative to the endogenous B15R promoter as part of the neo/rpsL cassette (FIG. 6A). MVA-dsneo-ΔB15 thus exactly reproduced the constellation of neo inserts in the CVA-dsneo-ΔB15 mutant described above. For construction of MVA-dsEGFP, the neo/EGFP cassette was first deleted from the BAC-insert of MVA wild-type. To obtain recombinant MVA-dsEGFP, the EGFP ORF was then inserted twice into the MVA genome at distant sites under control of early/late promoters directing transcription of either sense or anti-sense EGFP RNAs, enabling the formation of a dsRNA of 720 bp (FIG. 6B). An MVA construct expressing only a sense EGFP transcript from a single EGFP insertion (MVA-EGFP) served as reference for MVA-dsEGFP constructs throughout (FIG. 6B).

Murine A31 cells infected with an MVA generating complementary transcripts of the two inserted IFN-β gene transcription (FIG. 7A), compared to the BAC-derived MVA wt virus with a single neo cassette. When the whole BAC cassette containing the sense neo ORF was deleted from MVA-dsneo-ΔB15 using FRT-based recombination, the resulting MVA-neo-ΔB15/ΔBAC only induced wild-type levels of IFN-β mRNA (FIG. 7A). An MVA virus with a deletion of the B15R gene (MVA-ΔB15) and containing only the sense neo cassette in the BAC backbone also induced wild-type IFN-β mRNA levels (FIG. 7A). This demonstrated that the increased capacity of MVA-dsneo-ΔB15 to induce IFN-β was dependent on the presence of both sense and antisense neo expression cassettes, and was not caused by the B15R deletion per se. MVA-dsneo-ΔB15 as well as CVA-dsneo-ΔB15 induced high amounts of IFN-β mRNA after 5 hours of infection (FIG. 7A). IFN-β mRNA expression induced by MVA-dsneo-ΔB15 decreased between 5 and 7 hours post-infection, whereas CVA-dsneo-ΔB15 induced IFN-β mRNA levels remained high at 7 hours post-infection (FIG. 7A). Therefore, levels of MVA-dsneo-ΔBIS-induced IFN-β were determined at 5 hours post-infection in all further experiments. Culture supernatants of MVA-dsneo-ΔB15 infected A31 cells contained increased amounts of IFN-β 18 hours after infection compared to MVA wt or the single-neo cassette MVA constructs (FIG. 7B), confirming the results of the IFN-β mRNA analysis.

The above results were reproduced with a set of MVA recombinants directing the generation of complementary early transcripts from two separate EGFP inserts. One EGFP ORF under control of a strong early promoter directed the expression of sense EGFP-mRNA and was inserted into IGR136/137. The corresponding single-insertion MVA recombinant MVA-EGFP expressed EGFP and induced wild-type levels of IFN-β mRNA in murine A31 cells (FIG. 7C). An MVA containing an additional EGFP cassette inserted into IGR86/87 driving early/late expression of an antisense EGFP transcript under control of the pS promoter (Chakrabarti 1997) induced strongly increased amounts of IFN-β mRNA (FIG. 7C). Thus, early dsRNA derived from heterologous DNA inserts in the MVA genome stimulated IFN-β secretion independent of the sequence of the insert.

The latter observation was confirmed by analysis of IFN-β induction on the protein level. Similar to MVA-dsneo-ΔB15, MVA-dsEGFP stimulated the secretion of significantly higher amounts of IFN-β into culture supernatants than the corresponding MVA-EGFP (FIG. 7D). Amounts of IFN-β in the supernatants of A31 cells infected with the various MVA recombinants varied considerably between experiments presumably due to variation in passage number, cell density and state of the cells.

Example 6: Early Viral Transcription is Sufficient to Induce Increased IFN-β Levels by MVA dsRNA Mutants It was postulated that dsRNA-mediated IFN-β induction would be mainly dependent on dsRNA that is generated early during infection. Treatment of MVA-dsEGFP-2 infected mouse embryo fibroblast cells (MEFs) with AraC, which blocks replication of the viral genome and consequently post-replicative (intermediate and late) gene expression, did not diminish enhanced IFN-β gene expression (FIG. 8A), demonstrating that early transcription of dsRNA is sufficient for enhanced IFN-β induction. The reason for the moderate increase in IFN-β in MVA wt infected MEFs treated with AraC (FIG. 8A) is unclear. An MVA mutant lacking the E3L gene, which encodes a dsRNA binding protein masking dsRNA from recognition, enhanced IFN-β induction in MEFs to some extent, as expected from previously published observations in CEF and (Hornemann et al. (2003), *J. Virol.* 77:8394-8407). Treatment of MVA-ΔE3L-infected cells with AraC clearly decreased IFN-β induction (FIG. 8A). This was expected since significant amounts of viral dsRNA are naturally only generated at the post-replicative stage of the poxviral life cycle from ~2 hours post-infection onwards. Consistent with this notion, AraC-treated MVA-E3L did not induce more IFN-β mRNA than wt MVA when late gene expression was blocked by AraC treatment (FIG. 8A).

An MVA mutant expressing the antisense EGFP transcript under control of the late promoter pSSL (MVA-dsEGFP-late) induced levels of IFN-β mRNA similar to MVA wt (FIG. 8B). This provided further evidence that formation of dsRNA at early times of infection before the onset of DNA replication is a prerequisite for the IFN inducer phenotype of MVA-dsEGFP and highly likely also for MVA-dsneo-ΔB15. Thus, early expression of dsRNA by MVA is necessary and sufficient to induce IFN-β in infected cells. Very likely, the same principle is underlying the increased innate stimulatory capacity of CVA-dsneo-ΔB15.

Example 7: MVA-Dsneo-ΔB15 and MVA-dsEGFP Activate Protein Kinase R (PKR)

PKR is constitutively synthesized in cells at moderate levels as an inactive kinase, which is activated by binding to dsRNA. PKR expression is upregulated by type I IFN. One major substrate of activated PKR is the translation initiation factor subunit eIF2α, which is phosphorylated by PKR. Phosphorylation of eIF2α (P-eIF2α) upon infection leads to the abortion of translation in the infected cell as an antiviral countermeasure and might also be involved in PKR-mediated apoptosis induction. eIF2α phosphorylation was analyzed as an indicator for PKR activation by dsRNA in murine A31 cells. An MVA mutant (MVA-ΔE3L) lacking the gene for the vaccinia virus PKR inhibitor E3, which also binds and sequesters dsRNA, served as a positive control. MVA-dsneo-ΔB15 and MVA-dsEGFP activated PKR as early as 1 hour after infection of A31 cells, whereas MVA wt did not detectably activate PKR throughout infection (FIG. 9). The amount of P-eIF2α increased further until 4 hours post-infection in cells infected with both neo and EGFP-based early dsRNA producer mutants (FIG. 9). At 6 hours post-infection, P-eIF2α amounts in MVA-dsneo-ΔB15 and MVA-dsEGFP infected cells started to decline and were almost undetectable at 8 hours post-infection for MVA-dsneo-ΔB15, while P-eIF2α was still weakly detectable at this time point in MVA-dsEGFP infected cells (FIG. 9). In addition, the P-eIF2α signal was consistently stronger over the first 6 hours of infection in MVA-dsEGFP infected cells compared to MVA-dsneo-ΔB15 infected cells (FIG. 9), suggesting somewhat stronger PKR activating activity of MVA-dsEGFP compared to MVA-dsneo-ΔB15.

In contrast to the early dsRNA producer mutants, the P-eIF2α signal induced by MVA-ΔE3L was undetectable until 2 h post-infection and increased very sharply between 2 h and 3 h post-infection, remaining high for the rest of the observation period up to 8 h post-infection (FIG. 9). MVA-ΔE3L induced the strongest P-eIF2α signal of all mutants from 4 h post-infection onwards (FIG. 9). These kinetics are consistent with dsRNA being formed late in infection during MVA infection by annealing of partially complementary transcripts from intermediate and late viral genes. Due to the lack of E3, PKR activation induced by this late dsRNA was not blocked. In contrast, the kinetics of PKR activation by the MVA recombinants generating neo- or EGFP-dsRNA are consistent with a very early presence of stimulative amounts of dsRNA in infected cells. Since these recombinants express E3 protein, the PKR activation appears to be down-regulated later in infection when sufficient E3 protein has accumulated in infected cells.

Example 8: PKR is Required for Increased IFN-β mRNA Induction and Accumulation of IFN-ß in Cell Supernatants In wt MEFs, MVA-EGFP induced very similar amounts of IFN-β transcript like wt MVA as expected, whereas MVA-dsEGFP induced enhanced IFN-β mRNA synthesis (FIG. 10A). In contrast, MVA-dsEGFP did not induce enhanced IFN-β gene expression in PKR-deficient MEFs (FIG. 10A). The secretion of IFN-β protein by MVA-dsEGFP infected MEFs was likewise strongly dependent on functional PKR (FIG. 10B). Sendai virus (SeV), a negative strand RNA virus which is known to induce IFN-β via a PKR-independent pathway, served as positive control for the competency of PKR-deficient MEFs to secrete IFN-β. Interestingly, wt MEFs secreted only marginal amounts of IFN-β in response to SeV infection, if at all, whereas SeV efficiently induced IFN-β mRNA and protein in PKR$^{0/0}$ MEFs, confirming that the PKR$^{0/0}$ MEFs were fully competent to generate and secrete IFN-β (FIGS. 10A and 10B). Taken together, PKR appeared to be an important cellular sensor involved in the enhanced induction of IFN-β by MVA-dsEGFP. The induction of the IFN-β gene by MVA and MVA-EGFP (corresponding to wt MVA) in wt MEFs was also partially dependent on PKR (FIG. 10A), implicating a general role of this dsRNA sensor for innate immune activation by MVA, at least in MEFs. Taken together, the increased induction of IFN-β by MVA-dsEGFP was completely dependent on the dsRNA sensor PKR, which provides further evidence that dsRNA produced by MVA-dsEGFP is responsible for the observed increase in innate immune activation.

Example 9: Length Requirements for the Stimulatory Effect of Early dsRNA

The initial MVA-dsEGFP construct was designed to mimic the MVA-dsneo-ΔB15 construct, including a non-complementary overhang derived from the bacterial β-ga-lactosidase (β-gal) gene at the 3' end of the antisense EGFP transcript. To characterize further the dsRNA length requirements for enhanced IFN-β induction, a nested set of mutants with progressively shortened EGFP ORF overlaps of between 720 to 50 bp was constructed (FIG. 6B). MVA-dsEGFP-2 and all other dsEGFP mutants lacked the extra 3' overhang at the antisense transcript (FIG. 6B). In wt-MEFs, MVAs expressing complementary EGFP transcripts with decreasing EGFP overlap lengths induced decreasing amounts of IFN-β mRNA and protein (FIGS. 11A and 11B). In wt MEFs, the 3-gal-derived 3' overhang was not essential for the IFN-β enhancing effect (FIG. 11A). An EGFP transcript overlap of 100 bases (MVA-dsEGFP-5) stimulated clearly less IFN-β than MVA-dsEGFP but still enhanced the IFN-β response compared to the reference MVA-EGFP (FIGS. 11A and 11B). Again, in PKR$^{0/0}$ MEFs almost no IFN-β mRNA and no IFN-β was induced by the various MVA recombinants (FIGS. 11A and 11B). An MVA recombinant with a 50 bp EGFP insert overlap had no detectable excess IFN-β stimulating ability.

Thus, a minimum overlap of the two complementary recombinant transcripts of between 50 and 100 by was required for increased IFN-β induction in MEFs (FIG. 11C).

Example 10: MVA-dsEGFP Replication Properties and Stability of the Inducer Phenotype Propagation of MVA-dsEGFP in secondary chicken embryo fibroblasts (CEF) to obtain bulk purified MVA-dsEGFP preparations revealed normal virus yields within the range of MVA wt (data not shown). A multistep growth analysis demonstrated that MVA-dsEGFP retained a replication-restricted phenotype in human and murine cells (FIG. 12B), but replicated slightly less efficient in CEF as wt MVA (FIG. 12A). This slightly impaired replication was also observed when the average yields of viral stocks of MVA-dsEGFP obtained from CEF cells were related to those of MVA-EGFP. The ratio of the yields of MVA-dsEGFP/MVA-EGFP was around 0.5 (Table 1) and decreased further when MVA-EGFP yields were compared to those of MVA-5 and MVA-6 to about 0.1 (Table 1). Since MVA-dsEGFP-5 and -6 only induced slightly more IFN- if at all, the effect on viral replication was probably not mediated via soluble type I IFN. When chicken DF-1 cells were used for production of viral stocks, there was not a tendency to decreased yields when shorter EGFP-dsRNAs were expressed (Table 1). Thus, DF-1 cells represent an even more suitable cell type for propagation of early dsRNA-overproducing MVA mutants than CEF cells.

To assess whether the enhanced IFN-β stimulatory capacity of MVA-dsEGFP was preserved after repeated passaging, we conducted 10 passages of MVA-EGFP and MVA-dsEGFP in the interferon-competent chicken cell line DF-1 employing a low multiplicity of infection (MOI) of approximately 0.01. MVA-dsEGFP passaged 10 times on DF-1 cells induced an enhanced IFN-β response comparable to that of the starting MVA-dsEGFP virus passaged only once in DF-1 cells (FIG. 12C). Basal IFN-β induction of MVA-EGFP was also unaltered after 10 DF-1 passages (FIG. 12C). Thus, the enhanced interferon stimulatory capacity of MVA-dsEGFP was maintained after multiple passages in DF-1 cells. Neither MVA nor MVA-dsEGFP or MVA-dsneo-ΔB15 induced IFN-β gene expression in DF-1 cells or CEF cells (data not shown). This supported the notion that no strong counter-selective pressure was operative in DF-1 cells to relimit enhanced IFN type I induction during MVA-dsEGFP replication providing an argument for the observed stability of the IFN-β inducer phenotype. Taken together with the unimpaired yields of MVA-dsEGFP mutants, DF-1 cells represent an even more suitable cell type for propagation of early dsRNA-overproducing MVA mutants than CEF cells.

Example 11: Increased Induction of Cytokines In Vivo

Levels of systemic cytokines in response to infection of C57BL/6 mice with MVA-dsEGFP were analyzed at 6 hours post-infection The levels of IFN-α in blood after MVA-dsEGFP infection were significantly higher than those of the controls (FIG. 13A), similar to the in vitro observations (FIGS. 9 and 10). Levels of IFN-γ, the inflammatory cytokines IL-18 and IL-6 as well as of the chemokines CXCL1, CCL2, and CCL5 were also significantly increased in MVAdsEGFP-infected mice. The response was at least partially dependent on the presence of the signaling adaptor molecule IPS-1 (FIGS. 13A, 13B, 13C, 13D, 13E, 13F, and 13G), which is required for IFN type I and cytokine induction via the dsRNA recognition receptors RIG-I and MDA-5. In contrast, all observed increases in induction of cytokines and chemokines including IFN-$\alpha$, IFN-$\gamma$, IL-6, IL-18, CXCL1, CCL2, and CCL5 were dependent on PKR. Whereas basal induction of IFN-$\alpha$, CXCL1, and CCL2 by MVA-EGFP was not strongly affected by PKR deficiency, the basal levels of IFN-$\gamma$, IL-6, IL-18 and CCL5 appeared to be reduced in PKR-deficient mice. These results demonstrate that early dsRNA production by MVA enhanced the IFN type I response as well as inflammatory cytokine induction not only in cultured cells but also in vivo based on the activation of similar pattern recognition molecules like in cultured cells. PKR as well as recognition receptors signaling via IPS-1 were involved in mediating enhanced IFN type I expression by MVA-dsEGFP in vivo.

Example 13: Enhanced CD8 T Cell Responses by MVA-dsEGFP in Mice

C57BL/6 mice were immunized by different routes with MVA-dsEGFP and the CD8 T cell responses against the immunodominant epitopes in each strain background were determined using dextramer staining. The number of CD8 T cells in spleens of C57BL/6 mice directed against the immunodominant B8R epitope of vaccinia virus was significantly increased seven days after intravenous immunization with MVA-dsEGFP compared to MVA-EGFP (FIG. 14) (p=0.048 by unpaired two-tailed student's t test).

Example 14: Enhanced IFN-$\beta$ Gene Induction by MVA-dsEGFP in Human Cells To demonstrate that the stimulatory effect of early dsRNA generated by recombinant MVA is not limited to murine cells, cultures of the human diploid lung fibroblast cell line MRC-5 were infected with the MVA recombinants generating early dsRNA. Whereas basal IFN-$\beta$ gene induction by MVA-EGFP was occasionally undetectable in human MRC-5 cells (FIG. 15 and data not shown), MVA-dsneo-$\Delta$B15 and MVA-dsEGFP efficiently induced IFN-$\beta$ mRNA expression in human MRC-5 cells (FIG. 15). Efficiency of IFN-$\beta$ gene induction decreased with progressively shortened EGFP ORF overlaps (FIG. 15), similar to the results obtained with murine cells. Shortening the EGFP ORF overlap to 300 and 100 nt strongly reduced the IFN-$\beta$ stimulatory activity of the respective recombinants MVA-dsEGFP-4 and MVA-dsEGFP-5 (FIG. 15). Thus, increased IFN-$\beta$ induction by dsRNA generated early during infection with MVA is not confined to murine cells but was at least as prominent in human cells and hence is very likely to occur also in primary human cells and tissues as well as in human subjects vaccinated with recombinant poxviruses expressing complementary RNA transcripts.

Example 15: Enhanced IFN-$\beta$ Induction by MVA-dsE3L Generating Early dsRNA from a Native MVA Gene We inserted the early/late H5m promoter (Wyatt et al. (1996), Vaccine 14:1451-1458) possessing a strong early component downstream of the native early E3L ORF of MVA to direct early expression of antisense E3L RNA (FIG. 16A). The E3L ORF contains a homopolymeric T7 stretch in the antisense strand containing the $T_5NT$ consensus sequence of the orthopoxviral early transcription termination signal (ETTS). This antisense ETTS in the E3L ORF might probably limit the length of the early antisense transcript to approximately 250-300 nucleotides instead of the full ~650 nucleotides of the complete E3L transcript. We have therefore mutated this ETTS (FIG. 16A) by exchange of one T residue by an A without altering the encoded amino acid sequence of E3. A suitable antisense ETTS sequence for termination of the early full-length antisense E3 transcript was naturally present in the E3L/E4L intergenic region (FIG. 16A).

The resulting mutant MVA-dsE3L induced high levels of IFN-$\beta$ mRNA in MEFs (FIG. 16B) that were comparable to those of the best available dsRNA-based inducer, transfected poly (I:C), as positive control (data not shown). MVA-dsE3L appeared to induce clearly higher IFN-$\beta$ mRNA levels than MVA-dsEGFP (FIG. 16B). MVA-dsEGFP-5 and MVA-dsEGFP-late served as negative controls for IFN-$\beta$ mRNA induction together with the reference virus MVA-EGFP (FIG. 16B). Thus, generation of early dsRNA from MVA vectors can also be achieved by generation of early expressed antisense transcripts from native early MVA genes instead of inserting two partially or completely identical heterologous sequences.

Example 16: EGFP dsRNA Formation

To demonstrate the formation of dsRNA from sense and antisense transcripts of the EGFP gene in MVA-dsEGFP-720(o) infected cells, we isolated and combined total RNA from two 6-wells per virus of AraC-treated (40 µg/ml) BALB/3T3-A31 cells using the Trizol® method. DNase-treated total RNA samples were digested with single strand-specific RNases A and T1 (Ambion) or with RNase A/T1 plus dsRNA-specific RNase V1 (Ambion) in a total volume of 20 µl for 1 h at 37° C. The digested RNA samples and the untreated control sample (undigested) were purified using the RNA Clean & Concentrator kit (Zymo Research, Freiburg, Germany) and denatured at 95° C. for 3 min. Reverse transcription and quantitative PCR was performed as described above employing a commercially available EGFP TaqMan® assay (Mr04329676_mr, Life Technologies). The mean of the fold induction of EGFP RNA over mock from the duplicate qPCR reactions of undigested RNA samples was calculated and set to 100%. The percentage of remaining EGFP RNA was calculated employing the fold induction values of EGFP RNA after A/T1 and A/T1/V1 digests obtained from MVA-EGFP and MVA-dsEGFP-720 (o) infected cells.

Example 17: Cell and Viruses $IFNAR^{o/o}$ and $IPS-1^{o/o}$ mouse embryo fibroblasts (MEF) were prepared from 15-day old $C57BL/6-IFNAR^{o/o}$ and 14-day old $C57BL/6-IPS-1^{o/o}$ embryos by standard procedures, and $PKR^{o/o}$ MEFs and corresponding PKR-sufficient control MEFs. All cell lines were cultivated in Dulbecco's modified Eagle medium (DMEM, Gibco/Invitrogen, Darmstadt, Germany) supplemented with 10% fetal calf serum (FCS, Pan Biotech, Aidenbach, Germany). Primary chicken embryo fibroblast (CEF) cells were prepared from 11 day-old embryonated chicken eggs and cultured in VP-SFM (Gibco) for virus stock production or DMEM supplemented with 10% FCS for replication analysis. GM-CSF (granulocyte macrophage colony stimulating factor)-dependent dendritic cells (GM-DC) were generated from freshly prepared murine bone marrow by cultivation with recombinant murine GM-CSF (tebu-bio, Offenbach, Germany).

MVA wild-type (MVA) and MVA mutants were propagated on secondary CEF or DF-1 cells and titrated on CEF cells using the $TCID_{50}$ method as described (Meisinger-Hentschel et al., 2007. J Gen Virol. 84:3249-3259). CVA wild-type (CVA) and CVA mutants were propagated on Vero cells and titrated by the $TCID_{50}$ method on CV-1 cells. Shope Fibroma Virus was obtained from ATCC (VR-364) and was propagated and titrated on rabbit cornea SIRC cells. Sendai virus strain Cantell was obtained from Charles River Laboratories at 2000 HA units/ml. All viruses used in animal experiments were purified twice through a 36% sucrose cushion.

Example 18: BAC Recombineering and Reactivation of Infectious Virus

Construction of the CVA and MVA-BACs has been described previously (Lee and Esteban, 1994. Virology 199:491-496). For generation of MVA recombinants expressing sense and antisense EGFP mRNA and all corresponding controls, the neo-IRES-EGFP cassette in the BAC backbone of these constructs was replaced by a bacterial tetracycline resistance cassette. The MVA-EGFP recombinant contained a bacterial kanamycin resistance cassette (NPT I) downstream of the EGFP ORF, which is under the control of the strong early/late pHyb promoter. MVA-ΔE3L was obtained by replacing nucleotides 42697-43269 (ORF MVA050L) with a NPT I kanamycin resistance cassette by homologous recombination in E. coli.

For reactivation of infectious virus, 106 BHK-21 cells were transfected with 3 μg of BAC DNA using Fugene® HD (Promega, Mannheim, Germany), and 60 min later infected with Shope fibroma virus to provide the required helper functions. Reactivated virus was isolated and helper virus was removed as previously described (Meisinge(Meisinger-Henschel et al. (2007), J. Gen. Virol. 88:3249-3259).

Example 19: Mouse Infection Experiments

Mice were anaesthetized by ketamine/xylazine injection prior to intranasal infection with $2\times10^6$, $1\times10^7$, and $5\times10^7$ $TCID_{50}$ of CVA and CVA mutants diluted in PBS to a final volume of 50 μl per mouse. Animals were weighed and inspected daily for two weeks and the signs of illness were scored on an arbitrary scale from 0-4. For analysis of systemic cytokine levels, mice were injected i.v. with 200 μl of the respective virus dilutions and bled 6 h later by the tail vein.

Example 20: Systemic Cytokine Level Analysis by Cytometric Bead Assay

Cytokine concentrations in mouse sera drawn 6 h after i.v. infection were determined by the bead-based FlowCytomix assay for the indicated mouse cytokines (eBioscience, Frankfurt, Germany) according to the manufacturer's instructions. The statistical significance for differences between treatment groups was analyzed using the non-parametric Mann-Whitney U test. The overall significance level (0.05) was Bonferroni corrected by dividing with the number of groups (e.g. 11 cytokines and chemokines tested in B6129SF2/J mice), i.e. the overall Bonferroni corrected level was set to 0.05/11=0.00455 for comparison between B6129SF/2 treatment groups.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

---

We claim:

1. An engineered poxvirus that differs from wild-type poxvirus in comprising an additional early or immediate early poxviral promoter inserted downstream of the E3L gene and directing antisense transcription of said gene to produce an antisense RNA transcript that anneals with the sense transcript of said gene to form dsRNA that is more than 100 nucleotides in length.

2. The poxvirus of claim 1, wherein said dsRNA is produced prior to replication of the viral genome in a host cell infected with said poxvirus.

3. The poxvirus of claim 2, wherein said E3L coding region comprises inactivated antisense early transcription termination signals.

4. The poxvirus of claim 1, wherein said promoter is pH5m.

5. The poxvirus of claim 1, wherein said dsRNA is produced within 2 hours after infection of a host cell by the poxvirus.

6. The poxvirus of claim 1, wherein said dsRNA is more than 500 nucleotides in length.

7. The poxvirus of claim 1, further comprising heterologous sequences encoding one or more bacterial, viral, fungal, parasite, or tumor antigens.

8. The poxvirus of claim 1, further comprising heterologous sequences encoding the costimulatory molecules-known as TRICOM (B7-1, ICAM-1, and LFA-3).

9. The poxvirus of claim 1 that is selected from the group consisting of vaccinia virus, cowpox virus, and monkeypox virus.

10. The poxvirus of claim 9 that is a vaccinia virus that is modified vaccinia virus Ankara (MVA).

11. A method of enhancing an innate immune response comprising administering the poxvirus of claim 1 to a vertebrate subject; wherein said administration increases production of type I interferons (type I IFNs) in the subject.

12. The method of claim 11 wherein said administration increases the production of IFN-β in the subject by at least 2-fold.

13. The poxvirus of claim 1, wherein said promoter is selected from the group consisting of Pr7.5, PrS, I3L, 30K, 40K, PrHyb, PrS5E, Pr4LS5E, Pr13.5-long, and pE3L.

14. A non-human host cell comprising an engineered poxvirus that differs from wild-type poxvirus in comprising an additional early or immediate early poxviral promoter inserted downstream of the E3L gene and directing antisense transcription of said gene to produce an antisense RNA transcript that anneals with the sense transcript of said gene to form dsRNA in the host cell prior to replication of the viral genome, wherein said dsRNA is more than 100 nucleotides in length.

15. The host cell of claim 14 that comprises E3L dsRNA that is more than 500 nucleotides in length.

16. The host cell of claim 14 wherein said dsRNA is produced within 2 hours of infection of the host cell with the poxvirus.

17. The host cell of claim 14 wherein phosphorylation of a PKR substrate in the host cell is increased by at least 2-fold compared to a host cell comprising an unmodified poxvirus.

18. The host cell of claim 17 wherein said PKR substrate is Serine 51 of eIF2a.

19. A non-human host cell infected by an engineered poxvirus encoding E3L that comprises said poxvirus and further comprises dsRNA encoded by said E3L gene that is more than 100 nucleotides in length and is present in the host cell prior to replication of the viral genome, wherein the production of IFN-β by said host cell is increased by at least 2-fold compared to the production of IFN-β in a host cell infected with an unmodified poxvirus.

20. The host cell of claim 19, wherein said dsRNA is more than 500 nucleotides in length.

\* \* \* \* \*

SEQUENCE LISTING

<160> NUMBER OF SEQ ID NOS: 9

<210> SEQ ID NO 1
<211> LENGTH: 352
<212> TYPE: PRT
<213> ORGANISM: Monkeypox virus
<220> FEATURE:
<221> NAME/KEY: Accession No. Q5IXK2; IFN-alpha/beta-receptor-like
      secreted glycoprotein
<222> LOCATION: (1)..(352)

<400> SEQUENCE: 1

Met Met Lys Met Lys Met Met Val Arg Ile Tyr Phe Val Ser Leu Ser
1               5                   10                  15

Leu Leu Leu Phe His Ser Tyr Ala Ile Asp Ile Glu Asn Glu Ile Thr
            20                  25                  30

Glu Phe Phe Asn Lys Met Arg Asp Thr Leu Pro Ala Lys Asp Ser Lys
        35                  40                  45

Trp Leu Asn Pro Val Cys Met Phe Gly Gly Thr Met Asn Asp Met Ala
    50                  55                  60

Ala Leu Gly Glu Pro Phe Ser Ala Lys Cys Pro Pro Ile Glu Asp Ser
65                  70                  75                  80

Leu Leu Ser His Arg Tyr Lys Asp Tyr Val Val Lys Trp Glu Arg Leu
                85                  90                  95

Glu Lys Asn Arg Arg Arg Gln Val Ser Asn Lys Arg Val Lys His Gly

```
            100              105              110

Asp Leu Trp Ile Ala Asn Tyr Thr Ser Lys Phe Ser Asn Arg Arg Tyr
        115              120              125

Leu Cys Thr Val Thr Thr Lys Asn Gly Asp Cys Val Gln Gly Val Val
    130              135              140

Arg Ser His Val Trp Lys Pro Ser Ser Cys Ile Pro Lys Thr Tyr Glu
145              150              155              160

Leu Gly Thr Tyr Asp Lys Tyr Gly Ile Asp Leu Tyr Cys Gly Ile Leu
            165              170              175

Tyr Ala Lys His Tyr Asn Asn Ile Thr Trp Tyr Lys Asp Asn Lys Glu
        180              185              190

Ile Asn Ile Asp Asp Phe Lys Tyr Ser Gln Ala Gly Lys Glu Leu Ile
        195              200              205

Ile His Asn Pro Glu Leu Glu Asp Ser Gly Arg Tyr Asp Cys Tyr Val
    210              215              220

His Tyr Asp Asp Val Arg Ile Lys Asn Asp Ile Val Val Ser Arg Cys
225              230              235              240

Lys Ile Leu Thr Val Ile Pro Ser Gln Asp His Arg Phe Lys Leu Ile
        245              250              255

Leu Asp Pro Lys Ile Asn Val Thr Ile Gly Glu Pro Ala Asn Ile Thr
        260              265              270

Cys Ser Ala Val Ser Thr Ser Leu Phe Val Asp Asp Val Leu Ile Glu
    275              280              285

Trp Lys Asn Pro Ser Gly Trp Ile Ile Gly Leu Asp Phe Gly Val Tyr
    290              295              300

Ser Ile Leu Thr Ser Arg Gly Gly Ile Thr Glu Ala Thr Leu Tyr Phe
305              310              315              320

Glu Asn Val Thr Glu Glu Tyr Ile Gly Asn Thr Tyr Thr Cys Arg Gly
            325              330              335

His Asn Tyr Tyr Phe Asp Lys Thr Leu Thr Thr Thr Val Val Leu Glu
        340              345              350
```

<210> SEQ ID NO 2
<211> LENGTH: 351
<212> TYPE: PRT
<213> ORGANISM: Vaccinia virus, strain Western Reserve
<220> FEATURE:
<221> NAME/KEY: Accession No. P25213, Soluble interferon alpha/beta
      receptor B19
<222> LOCATION: (1)..(351)

<400> SEQUENCE: 2

```
Met Thr Met Lys Met Met Val His Ile Tyr Phe Val Ser Leu Leu Leu
1               5               10              15

Leu Leu Phe His Ser Tyr Ala Ile Asp Ile Glu Asn Glu Ile Thr Glu
            20              25              30

Phe Phe Asn Lys Met Arg Asp Thr Leu Pro Ala Lys Asp Ser Lys Trp
        35              40              45

Leu Asn Pro Ala Cys Met Phe Gly Gly Thr Met Asn Asp Ile Ala Ala
    50              55              60

Leu Gly Glu Pro Phe Ser Ala Lys Cys Pro Ile Glu Asp Ser Leu
65              70              75              80

Leu Ser His Arg Tyr Lys Asp Tyr Val Val Lys Trp Glu Arg Leu Glu
            85              90              95

Lys Asn Arg Arg Arg Gln Val Ser Asn Lys Arg Val Lys His Gly Asp
            100              105              110
```

-continued

```
Leu Trp Ile Ala Asn Tyr Thr Ser Lys Phe Ser Asn Arg Arg Tyr Leu
        115                 120                 125

Cys Thr Val Thr Thr Lys Asn Gly Asp Cys Val Gln Gly Ile Val Arg
        130                 135                 140

Ser His Ile Arg Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His Tyr Asn Asn Ile Thr Trp Tyr Lys Asp Asn Lys Glu Ile
                180                 185                 190

Asn Ile Asp Asp Ile Lys Tyr Ser Gln Thr Gly Lys Glu Leu Ile Ile
        195                 200                 205

His Asn Pro Glu Leu Glu Asp Ser Gly Arg Tyr Asp Cys Tyr Val His
        210                 215                 220

Tyr Asp Asp Val Arg Ile Lys Asn Asp Ile Val Val Ser Arg Cys Lys
225                 230                 235                 240

Ile Leu Thr Val Ile Pro Ser Gln Asp His Arg Phe Lys Leu Ile Leu
                245                 250                 255

Asp Pro Lys Ile Asn Val Thr Ile Gly Glu Pro Ala Asn Ile Thr Cys
                260                 265                 270

Thr Ala Val Ser Thr Ser Leu Leu Ile Asp Asp Val Leu Ile Glu Trp
        275                 280                 285

Glu Asn Pro Ser Gly Trp Leu Ile Gly Phe Asp Phe Asp Val Tyr Ser
        290                 295                 300

Val Leu Thr Ser Arg Gly Gly Ile Thr Glu Ala Thr Leu Tyr Phe Glu
305                 310                 315                 320

Asn Val Thr Glu Glu Tyr Ile Gly Asn Thr Tyr Lys Cys Arg Gly His
                325                 330                 335

Asn Tyr Tyr Phe Glu Lys Thr Leu Thr Thr Thr Val Val Leu Glu
                340                 345                 350
```

```
<210> SEQ ID NO 3
<211> LENGTH: 351
<212> TYPE: PRT
<213> ORGANISM: Vaccinia virus, strain Copenhagen
<220> FEATURE:
<221> NAME/KEY: Accession No. Q5CAD5:  IFN-alpha-beta-receptor-like
      secreted glycoprotein; Vaccinia virus, strain Copenhagen
<222> LOCATION: (1)..(351)
<220> FEATURE:
<221> NAME/KEY: Accession No. Q5CAD5:  IFN-alpha-beta-receptor-like
      secreted glycoprotein
<222> LOCATION: (1)..(351)

<400> SEQUENCE: 3
```

```
Met Thr Met Lys Met Met Val His Ile Tyr Phe Val Ser Leu Leu Leu
1               5                   10                  15

Leu Leu Phe His Ser Tyr Ala Ile Asp Ile Glu Asn Glu Ile Thr Glu
                20                  25                  30

Phe Phe Asn Lys Met Arg Asp Thr Leu Pro Ala Lys Asp Ser Lys Trp
            35                  40                  45

Leu Asn Pro Ala Cys Met Phe Gly Gly Thr Met Asn Asp Ile Ala Ala
        50                  55                  60

Leu Gly Glu Pro Phe Ser Ala Lys Cys Pro Pro Ile Glu Asp Ser Leu
65                  70                  75                  80

Leu Ser His Arg Tyr Lys Asp Tyr Val Val Lys Trp Glu Arg Leu Glu
                85                  90                  95
```

-continued

```
Lys Asn Arg Arg Arg Gln Val Ser Asn Lys Arg Val Lys His Gly Asp
            100                 105                 110

Leu Trp Ile Ala Asn Tyr Thr Ser Lys Phe Ser Asn Arg Arg Tyr Leu
            115                 120                 125

Cys Thr Val Thr Thr Lys Asn Gly Asp Cys Val Gln Gly Ile Val Arg
            130                 135                 140

Ser His Ile Lys Lys Pro Pro Ser Cys Ile Pro Lys Thr Tyr Glu Leu
145                 150                 155                 160

Gly Thr His Asp Lys Tyr Gly Ile Asp Leu Tyr Cys Gly Ile Leu Tyr
                165                 170                 175

Ala Lys His Tyr Asn Asn Ile Thr Trp Tyr Lys Asp Asn Lys Glu Ile
                180                 185                 190

Asn Ile Asp Asp Ile Lys Tyr Ser Gln Thr Gly Lys Lys Leu Ile Ile
                195                 200                 205

His Asn Pro Glu Leu Glu Asp Ser Gly Arg Tyr Asn Cys Tyr Val His
            210                 215                 220

Tyr Asp Asp Val Arg Ile Lys Asn Asp Ile Val Val Ser Arg Cys Lys
225                 230                 235                 240

Ile Leu Thr Val Ile Pro Ser Gln Asp His Arg Phe Lys Leu Ile Leu
                245                 250                 255

Asp Pro Lys Ile Asn Val Thr Ile Gly Glu Pro Ala Asn Ile Thr Cys
                260                 265                 270

Thr Ala Val Ser Thr Ser Leu Leu Ile Asp Asp Val Leu Ile Glu Trp
            275                 280                 285

Glu Asn Pro Ser Gly Trp Leu Ile Gly Phe Asp Phe Asp Val Tyr Ser
            290                 295                 300

Val Leu Thr Ser Arg Gly Gly Ile Thr Glu Ala Thr Leu Tyr Phe Glu
305                 310                 315                 320

Asn Val Thr Glu Glu Tyr Ile Gly Asn Thr Tyr Lys Cys Arg Gly His
                325                 330                 335

Asn Tyr Tyr Phe Glu Lys Thr Leu Thr Thr Thr Val Val Leu Glu
                340                 345                 350
```

```
<210> SEQ ID NO 4
<211> LENGTH: 353
<212> TYPE: PRT
<213> ORGANISM: Vaccinia virus, strain Ankara (CVA)
<220> FEATURE:
<221> NAME/KEY: Accession No. A9J168:  Soluble and cell surface
      interferon-alpha/beta receptor;
<222> LOCATION: (1)..(353)

<400> SEQUENCE: 4
```

```
Met Lys Met Thr Met Lys Met Met Val His Ile Tyr Phe Val Ser Leu
1               5                   10                  15

Leu Leu Leu Leu Phe His Ser Tyr Ala Ile Asp Ile Glu Asn Glu Ile
            20                  25                  30

Thr Glu Phe Phe Asn Lys Met Arg Asp Thr Leu Pro Ala Lys Asp Ser
            35                  40                  45

Lys Trp Leu Asn Pro Ala Cys Met Phe Gly Gly Thr Met Asn Asp Ile
            50                  55                  60

Ala Ala Leu Gly Glu Pro Phe Ser Ala Lys Cys Pro Pro Ile Glu Asp
65                  70                  75                  80

Ser Leu Leu Ser His Arg Tyr Lys Asp Tyr Val Val Lys Trp Glu Arg
                85                  90                  95
```

```
Leu Glu Lys Asn Arg Arg Arg Gln Val Ser Asn Lys Arg Val Lys His
        100                 105                 110

Gly Asp Leu Trp Ile Ala Asn Tyr Thr Ser Lys Phe Ser Asn Arg Arg
        115                 120                 125

Tyr Leu Cys Thr Val Thr Thr Lys Asn Gly Asp Cys Val Gln Gly Ile
        130                 135                 140

Val Arg Ser His Ile Lys Lys Pro Pro Ser Cys Ile Pro Lys Thr Tyr
145                 150                 155                 160

Glu Leu Gly Thr His Asp Lys Tyr Gly Ile Asp Leu Tyr Cys Gly Ile
                165                 170                 175

Leu Tyr Ala Lys His Tyr Asn Asn Ile Thr Trp Tyr Lys Asp Asn Lys
            180                 185                 190

Glu Ile Asn Ile Asp Asp Ile Lys Tyr Ser Gln Thr Gly Lys Lys Leu
            195                 200                 205

Ile Ile His Asn Pro Glu Leu Glu Asp Ser Gly Arg Tyr Asn Cys Tyr
        210                 215                 220

Val His Tyr Asp Asp Val Lys Ile Lys Asn Asp Ile Val Val Ser Arg
225                 230                 235                 240

Cys Lys Ile Leu Thr Val Ile Pro Ser Gln Asp His Arg Phe Lys Leu
                245                 250                 255

Ile Leu Asp Pro Lys Ile Asn Val Thr Ile Gly Glu Pro Ala Asn Ile
                260                 265                 270

Thr Cys Thr Ala Val Ser Thr Ser Leu Leu Ile Asp Asp Val Leu Ile
        275                 280                 285

Glu Trp Glu Asn Pro Ser Gly Trp Leu Ile Gly Phe Asp Phe Asp Val
        290                 295                 300

Tyr Ser Val Leu Thr Ser Arg Gly Gly Ile Thr Glu Ala Thr Leu Tyr
305                 310                 315                 320

Phe Glu Asn Val Thr Glu Glu Tyr Ile Gly Asn Thr Tyr Lys Cys Arg
                325                 330                 335

Gly His Asn Tyr Tyr Phe Glu Lys Thr Leu Thr Thr Thr Val Val Leu
            340                 345                 350

Glu

<210> SEQ ID NO 5
<211> LENGTH: 358
<212> TYPE: PRT
<213> ORGANISM: Ectromelia virus
<220> FEATURE:
<221> NAME/KEY: Accession No. Q9JFS5:  IFN-alpha/beta binding protein
<222> LOCATION: (1)..(358)

<400> SEQUENCE: 5

Met Met Lys Met Thr Met Lys Met Met Val Arg Ile Tyr Phe Val Ser
1                 5                   10                  15

Leu Ser Leu Ser Leu Ser Leu Leu Leu Phe His Ser Tyr Ala Ile Asp
            20                  25                  30

Ile Glu Asn Glu Ile Thr Glu Phe Phe Asn Lys Met Arg Asp Thr Leu
        35                  40                  45

Pro Ala Lys Asp Ser Lys Trp Leu Asn Pro Ser Cys Met Phe Gly Gly
        50                  55                  60

Thr Met Asn Asp Met Ala Ala Leu Gly Glu Pro Phe Ser Ala Lys Cys
65                  70                  75                  80

Pro Pro Ile Glu Asp Ser Leu Leu Ser His Arg Tyr Asn Asp Lys Asp
                85                  90                  95
```

-continued

```
Asn Val Val Asn Trp Glu Lys Ile Gly Lys Thr Arg Arg Pro Leu Asn
                100                 105                 110

Arg Arg Val Lys Asn Gly Asp Leu Trp Ile Ala Asn Tyr Thr Ser Asn
            115                 120                 125

Asp Ser His Arg Arg Tyr Leu Cys Thr Val Thr Thr Lys Asn Gly Asp
        130                 135                 140

Cys Val Gln Gly Ile Val Arg Ser His Ile Arg Lys Pro Pro Ser Cys
145                 150                 155                 160

Ile Pro Glu Thr Tyr Glu Leu Gly Thr His Asp Lys Tyr Gly Ile Asp
                165                 170                 175

Leu Tyr Cys Gly Ile Leu Tyr Ala Lys His Tyr Asn Asn Ile Thr Trp
            180                 185                 190

Tyr Lys Asn Asn Gln Glu Leu Ile Ile Asp Gly Thr Lys Tyr Ser Gln
            195                 200                 205

Ser Gly Gln Asn Leu Ile Ile His Asn Pro Glu Leu Glu Asp Ser Gly
        210                 215                 220

Arg Tyr Asp Cys Tyr Val His Tyr Asp Asp Val Arg Ile Lys Asn Asp
225                 230                 235                 240

Ile Val Val Ser Arg Cys Lys Ile Leu Thr Val Ile Pro Ser Gln Asp
                245                 250                 255

His Arg Phe Lys Leu Ile Leu Asp Pro Lys Ile Asn Val Thr Ile Gly
            260                 265                 270

Glu Pro Ala Asn Ile Thr Cys Thr Ala Val Ser Thr Ser Leu Leu Val
            275                 280                 285

Asp Asp Val Leu Ile Asp Trp Glu Asn Pro Ser Gly Trp Ile Ile Gly
        290                 295                 300

Leu Asp Phe Gly Val Tyr Ser Ile Leu Thr Ser Ser Gly Gly Ile Thr
305                 310                 315                 320

Glu Ala Thr Leu Tyr Phe Glu Asn Val Thr Glu Glu Tyr Ile Gly Asn
                325                 330                 335

Thr Tyr Thr Cys Arg Gly His Asn Tyr Tyr Phe Asp Lys Thr Leu Thr
            340                 345                 350

Thr Thr Val Val Leu Glu
        355
```

```
<210> SEQ ID NO 6
<211> LENGTH: 357
<212> TYPE: PRT
<213> ORGANISM: Cowpox virus
<220> FEATURE:
<221> NAME/KEY: Accession No. Q5CAC3:  Soluble interferon-alpha/beta
      receptor
<222> LOCATION: (1)..(357)

<400> SEQUENCE: 6
```

```
Met Lys Met Thr Met Lys Met Met Val His Ile Tyr Phe Val Ser Leu
1               5                   10                  15

Ser Leu Ser Leu Ser Leu Leu Leu Phe His Ser Tyr Ala Ile Asp Ile
            20                  25                  30

Glu Asn Glu Ile Thr Glu Phe Phe Asn Lys Met Lys Asp Thr Leu Pro
        35                  40                  45

Ala Lys Asp Ser Lys Trp Leu Asn Pro Ala Cys Met Phe Gly Gly Thr
        50                  55                  60

Met Asn Asp Met Ala Ala Ile Gly Glu Pro Phe Ser Ala Lys Cys Pro
65                  70                  75                  80

Pro Ile Glu Asp Ser Leu Leu Ser His Arg Tyr Lys Asp Lys Asp Asn
```

-continued

```
                  85                  90                  95

Val Val Asn Trp Glu Lys Ile Gly Lys Thr Arg Arg Pro Leu Asn Arg
                 100                 105                 110

Arg Val Lys Asn Gly Asp Leu Trp Ile Ala Asn Tyr Thr Ser Asn Asp
                 115                 120                 125

Ser Arg Arg Arg Tyr Leu Cys Thr Val Ile Thr Lys Asn Gly Asp Cys
             130                 135                 140

Ile Gln Gly Ile Val Arg Ser His Val Arg Lys Pro Ser Ser Cys Ile
145                 150                 155                 160

Pro Glu Ile Tyr Glu Leu Gly Thr His Asp Lys Tyr Gly Ile Asp Leu
                 165                 170                 175

Tyr Cys Gly Ile Ile Tyr Ala Lys His Tyr Asn Asn Ile Thr Trp Tyr
             180                 185                 190

Lys Asp Asn Lys Glu Ile Asn Ile Asp Asp Ile Lys Tyr Ser Gln Thr
                 195                 200                 205

Gly Lys Glu Leu Ile Ile His Asn Pro Ala Leu Glu Asp Ser Gly Arg
             210                 215                 220

Tyr Asp Cys Tyr Val His Tyr Asp Asp Val Arg Ile Lys Asn Asp Ile
225                 230                 235                 240

Val Val Ser Arg Cys Lys Ile Leu Thr Val Ile Pro Ser Gln Asp His
                 245                 250                 255

Arg Phe Lys Leu Ile Leu Asp Pro Lys Ile Asn Val Thr Ile Gly Glu
                 260                 265                 270

Pro Ala Asn Ile Thr Cys Thr Ala Val Ser Thr Ser Leu Leu Val Asp
             275                 280                 285

Asp Val Leu Ile Glu Trp Glu Asn Pro Ser Gly Trp Leu Ile Gly Phe
         290                 295                 300

Asp Phe Asp Val Tyr Ser Val Leu Thr Ser Arg Gly Gly Ile Thr Glu
305                 310                 315                 320

Ala Thr Leu Tyr Phe Glu Asn Val Thr Glu Glu Tyr Ile Gly Asn Thr
                 325                 330                 335

Tyr Lys Cys Arg Gly His Asn Tyr Tyr Phe Glu Lys Thr Leu Thr Thr
             340                 345                 350

Thr Val Val Leu Glu
         355

<210> SEQ ID NO 7
<211> LENGTH: 355
<212> TYPE: PRT
<213> ORGANISM: Camelpox virus
<220> FEATURE:
<221> NAME/KEY: Accession No. Q5CA87:  Soluble interferon-alpha/beta
      receptor
<222> LOCATION: (1)..(355)

<400> SEQUENCE: 7

Met Lys Met Thr Met Lys Met Met Val His Ile Tyr Phe Val Ser Leu
1               5                   10                  15

Ser Leu Ser Leu Leu Leu Phe His Ser Tyr Ala Ile Asp Ile Glu Asn
                 20                  25                  30

Glu Ile Thr Asp Phe Phe Asn Lys Met Lys Asp Ile Leu Pro Thr Lys
             35                  40                  45

Asp Ser Lys Trp Leu Asn Pro Ala Cys Met Phe Gly Gly Thr Thr Asn
         50                  55                  60

Asp Met Ala Ala Ile Gly Glu Pro Phe Ser Ala Lys Cys Pro Pro Ile
65                  70                  75                  80
```

-continued

```
Glu Asp Ser Leu Leu Ser His Arg Tyr Lys Asn Lys Asp Asn Val Val
             85              90              95

Asn Trp Glu Lys Ile Gly Lys Thr Lys Arg Pro Leu Asn Arg Arg Val
            100             105             110

Lys Asn Gly Asp Leu Trp Ile Ala Asn Tyr Thr Ser Asn Asp Ser Arg
            115             120             125

Arg Arg Tyr Leu Cys Thr Ala Ile Thr Lys Asn Gly Asp Cys Ile Gln
        130             135             140

Gly Ile Ile Arg Ser His Val Arg Lys Pro Ser Ser Cys Ile Pro Glu
145             150             155             160

Ile Tyr Glu Leu Gly Thr His Asp Lys Tyr Gly Ile Asp Leu Tyr Cys
            165             170             175

Gly Ile Ile Tyr Ala Lys His Tyr Asn Asn Ile Thr Trp Tyr Lys Asp
            180             185             190

Asn Lys Glu Ile Asn Ile Asp Asp Ile Lys Tyr Ser Gln Thr Gly Lys
            195             200             205

Glu Leu Ile Ile His Asn Pro Ala Leu Glu Asp Ser Gly Arg Tyr Asp
        210             215             220

Cys Tyr Val His Tyr Asp Asp Val Arg Ile Lys Asn Asp Ile Val Val
225             230             235             240

Ser Arg Cys Lys Ile Leu Thr Val Thr Pro Ser Gln Asp His Arg Phe
            245             250             255

Lys Leu Ile Leu Asp Pro Lys Ile Asn Val Thr Ile Gly Glu Pro Ala
            260             265             270

Asn Ile Thr Cys Thr Ala Val Ser Thr Ser Leu Leu Val Asp Asp Val
            275             280             285

Leu Ile Glu Trp Glu Asn Pro Ser Gly Trp Leu Ile Gly Phe Asp Phe
        290             295             300

Asp Val Tyr Ser Val Leu Thr Ser Arg Gly Gly Ile Thr Glu Ala Thr
305             310             315             320

Leu Tyr Phe Glu Asn Val Thr Glu Glu Tyr Ile Gly Asn Thr Tyr Lys
            325             330             335

Cys Arg Gly His Asn Tyr Tyr Phe Glu Lys Thr Leu Thr Thr Thr Val
            340             345             350

Val Leu Glu
        355
```

```
<210> SEQ ID NO 8
<211> LENGTH: 344
<212> TYPE: PRT
<213> ORGANISM: Swinepox virus, strain Swine/Nebraska/17077-99/1999
<220> FEATURE:
<221> NAME/KEY: Accession No. Q8V3G4: IFN-alpha/beta-like binding
      protein
<222> LOCATION: (1)..(344)

<400> SEQUENCE: 8
```

```
Met Ile Ser Ile Lys Lys Tyr Asn Ile Leu Leu Phe Ile Ile Ser Phe
1               5               10              15

Ile Tyr Cys Ser Ala Asp Asn Asp Ile Asp Ser Leu Tyr Glu Gly Tyr
            20              25              30

Lys Glu Phe Leu Asp Pro Lys Leu Lys Gln Phe Leu Asn Asp Asn Cys
            35              40              45

Thr Tyr Arg Gly Tyr Arg Asp Phe Phe Leu Tyr Asn Glu Glu Pro Ala
        50              55              60
```

-continued

```
Asn Ile Lys Cys Pro Leu Leu Asn Asp Ile Leu Leu Arg Gln Lys Tyr
65                  70                  75                  80

His Asn Tyr Thr Ile Leu Trp Lys Lys Leu Gly Glu Arg Ser Ser Arg
                85                  90                  95

Leu Leu Asn Thr His Gly Ser Ile Phe Leu Asp Phe Phe Pro Tyr Lys
                100                 105                 110

Ser Glu Leu Arg Gly Ser Val Tyr Glu Cys Met Ile Ile Leu Asn Asn
            115                 120                 125

Thr Cys Asp Gln Phe Ile Leu Lys Leu Asn Asp Ile Arg Ser Asn Pro
            130                 135                 140

Val Cys Tyr His Asn Asp Tyr Lys Val His Thr Asn Ile Glu Ile Phe
145                 150                 155                 160

Cys Asn Val Ile Asn Leu Gln Tyr Asp Tyr Ile Thr Trp Tyr Lys Asn
                165                 170                 175

Asn Ser Glu Ile Ile Ile Asp Gly Tyr Lys Tyr Ser Asn Gln Ser Arg
                180                 185                 190

Arg Leu Leu Val Tyr Asn Thr Thr Tyr Asn Asp Ser Gly Ile Tyr Tyr
                195                 200                 205

Cys Asn Ala Tyr Thr Thr His Gly Lys Asn Thr Tyr Ile Ser Arg Arg
            210                 215                 220

Cys Ser Ser Val Ser Ile His Ser His Ser Tyr Tyr Asp Phe Tyr Ile
225                 230                 235                 240

Glu His Ile Asn Asn Ile Thr Tyr Ile Asp Pro Asp Ser Glu Asn Thr
                245                 250                 255

Gln Ile Tyr Cys Lys Ala Ile Ser Tyr Ser Asn Ser Ser Tyr Ile Leu
                260                 265                 270

Ile Tyr Trp Glu Asp Glu Tyr Gly Gly Tyr Ile Tyr Asp Asn Gly Ile
            275                 280                 285

Tyr Gln Tyr Asp Asn Ile Thr Leu Ile Gly Asn Glu Lys Val Tyr Met
    290                 295                 300

Ser Ile Leu Val Leu Glu Lys Ser Ala Tyr Tyr Arg Tyr Val Asn Asn
305                 310                 315                 320

Thr Phe Thr Cys Leu Ala Thr Ser Val Tyr Val Glu Lys Lys Thr Thr
                325                 330                 335

Thr Thr Leu Val Ile Lys Lys Thr
                340
```

```
<210> SEQ ID NO 9
<211> LENGTH: 351
<212> TYPE: PRT
<213> ORGANISM: Tanapox virus
<220> FEATURE:
<221> NAME/KEY: Accession No. A7XCS4:  Type-I IFN receptor
<222> LOCATION: (1)..(351)

<400> SEQUENCE: 9
```

```
Met Lys Ile Thr Tyr Ile Ile Leu Leu Ile Cys Lys Glu Ile Ile Cys
1               5                   10                  15

Asp Asn Ser Gly Asp Asp Met Tyr Asp Tyr Ile Ala Asn Gly Asn Ile
                20                  25                  30

Asp Tyr Leu Lys Thr Ile Asp Asn Asp Ile Ile Asn Leu Val Asn Lys
            35                  40                  45

Asn Cys Ser Phe Arg Glu Ile Lys Thr Thr Leu Ala Lys Glu Asn Glu
        50                  55                  60

Val Leu Met Leu Lys Cys Pro Gln Leu Asp Asn Tyr Ile Leu Pro Trp
65                  70                  75                  80
```

-continued

```
Lys Tyr Met Asn Arg Ser Glu Tyr Thr Val Thr Trp Lys Asn Ile Ser
                85                  90                  95

Asn Ser Thr Glu Tyr Asn Asn Thr Arg Ile Glu Asn Asn Met Leu Met
            100                 105                 110

Phe Phe Pro Phe Tyr Asn Leu Gln Ala Gly Ser Lys Tyr Leu Cys Thr
            115                 120                 125

Val Ser Thr Asn Lys Ser Cys Asp Gln Ser Val Val Ile Val Lys Lys
    130                 135                 140

Ser Phe Tyr Ser Asn Asn Cys Met Leu Ser Glu Ala Lys Glu Asn Asp
145                 150                 155                 160

Asn Phe Glu Ile Tyr Cys Gly Ile Leu His Ala Lys Tyr Asn Thr Ile
                165                 170                 175

Lys Trp Phe Lys Glu Glu Lys Glu Ile Thr Asn Asn Tyr Lys Tyr Tyr
            180                 185                 190

Thr Lys Leu Gly Gly Tyr Val Lys Gly Ile Asn Asn Val Thr Tyr Ser
            195                 200                 205

Asp Ser Gly Lys Tyr Val Cys Glu Gly Tyr Tyr Ile Asp Val Leu Lys
    210                 215                 220

Asn Ile Thr Tyr Thr Ala Lys Arg Cys Val Asn Leu Thr Val Ile Pro
225                 230                 235                 240

Asn Thr Tyr Tyr Asp Phe Phe Ile Val Asp Ile Pro Asn Val Thr Tyr
            245                 250                 255

Ala Lys Asn Asn Lys Lys Leu Glu Val Asn Cys Thr Ser Phe Val Asp
            260                 265                 270

Ile Asn Ser Tyr Asp Tyr Ile Leu Thr Ser Trp Leu Tyr Asn Gly Leu
            275                 280                 285

Tyr Leu Pro Leu Gly Val Arg Ile Tyr Gln Leu Tyr Ser Thr Asp Ile
    290                 295                 300

Phe Phe Glu Asn Phe Ile Tyr Arg Thr Ser Thr Leu Val Phe Glu Asn
305                 310                 315                 320

Val Asp Ile Ser Asp Asp Asn Lys Thr Phe Glu Cys Glu Ala Leu Ser
            325                 330                 335

Val Thr Leu Lys Lys Ile Lys Tyr Thr Thr Ile Lys Val Glu Lys
            340                 345                 350
```